United States Patent
Hundertmark et al.

(10) Patent No.: US 8,721,680 B2
(45) Date of Patent: May 13, 2014

(54) APPARATUS AND METHODS FOR SEALING A VASCULAR PUNCTURE

(71) Applicant: AccessClosure, Inc., Mountain View, CA (US)

(72) Inventors: Ronald Hundertmark, San Mateo, CA (US); Andy Uchida, Los Altos, CA (US); Moshe Zilversmit, Campbell, CA (US); David Fiscella, Dublin, CA (US); Brandon Fell, Dublin, CA (US); Vincent Ku, Palo Alto, CA (US)

(73) Assignee: AccessClosure, Inc., Mountain View, CA (US)

( * ) Notice: Subject to any disclaimer, the term of this patent is extended or adjusted under 35 U.S.C. 154(b) by 0 days.

(21) Appl. No.: 13/839,590

(22) Filed: Mar. 15, 2013

(65) Prior Publication Data

US 2013/0253579 A1 Sep. 26, 2013

Related U.S. Application Data

(60) Provisional application No. 61/615,202, filed on Mar. 23, 2012.

(51) Int. Cl.
*A61B 17/08* (2006.01)

(52) U.S. Cl.
USPC .................................................. 606/213

(58) Field of Classification Search
USPC ......... 606/151, 157, 191, 194, 198, 213, 214; 604/15–18
See application file for complete search history.

(56) References Cited

U.S. PATENT DOCUMENTS

| | | |
|---|---|---|
| 2,365,039 A | 12/1944 | Andresen |
| 3,765,419 A | 10/1973 | Usher |
| 4,002,173 A | 1/1977 | Manning |
| 4,472,542 A | 9/1984 | Nambu |
| 4,655,211 A | 4/1987 | Sakamoto |
| 4,664,857 A | 5/1987 | Nambu |
| 4,734,097 A | 3/1988 | Tanabe |
| 4,738,658 A | 4/1988 | Magro |
| 4,790,819 A | 12/1988 | Li et al. |

(Continued)

FOREIGN PATENT DOCUMENTS

| | | |
|---|---|---|
| EP | 476178 | 3/1992 |
| WO | WO 92/22252 | 12/1992 |

(Continued)

OTHER PUBLICATIONS

Chisholm, et al., *Fibrin Sealant as a Plug for the Post Liver Biopsy Needle Track*, 40(6) Clinical Radiology 627-28 (Nov. 1989).

(Continued)

*Primary Examiner* — Tuan V Nguyen
*Assistant Examiner* — David Eastwood
(74) *Attorney, Agent, or Firm* — Knobbe Martens Olson & Bear LLP

(57) ABSTRACT

An apparatus for sealing a puncture through a vessel wall including a positioning assembly, a sheath releasably engaged with the positioning assembly, and a support member axially advanceable through the sheath. The positioning assembly includes a positioning element positioned at a distal portion of the positioning assembly and a sealant disposed at a distal portion of the positioning assembly. The sheath guides the sealant and positioning assembly to the puncture in the vessel wall.

19 Claims, 34 Drawing Sheets

(56) References Cited

U.S. PATENT DOCUMENTS

| | | |
|---|---|---|
| 4,838,280 A | 6/1989 | Haaga |
| 4,852,568 A | 8/1989 | Kensey |
| 4,890,612 A | 1/1990 | Kensey |
| 5,021,059 A | 6/1991 | Kensey et al. |
| 5,061,274 A | 10/1991 | Kensey |
| 5,108,421 A | 4/1992 | Fowler |
| 5,192,302 A | 3/1993 | Kensey |
| 5,221,259 A | 6/1993 | Weldom |
| 5,228,851 A | 7/1993 | Burton |
| 5,258,042 A | 11/1993 | Mehta |
| 5,275,616 A | 1/1994 | Fowler |
| 5,290,310 A | 3/1994 | Makower |
| 5,292,332 A | 3/1994 | Lee |
| 5,310,407 A | 5/1994 | Casale |
| 5,320,639 A | 6/1994 | Rudnick |
| 5,324,306 A | 6/1994 | Makower |
| 5,334,216 A | 8/1994 | Vidal |
| 5,370,660 A | 12/1994 | Weinstein |
| 5,383,896 A | 1/1995 | Gershony |
| 5,391,183 A | 2/1995 | Janzen et al. |
| 5,409,703 A | 4/1995 | McAnalley |
| 5,413,571 A | 5/1995 | Katsaros |
| 5,419,765 A | 5/1995 | Weldon |
| 5,431,639 A | 7/1995 | Shaw |
| 5,437,292 A | 8/1995 | Kipshidze |
| 5,437,631 A | 8/1995 | Janzen |
| 5,441,517 A | 8/1995 | Kensey |
| 5,464,396 A | 11/1995 | Barta |
| 5,486,195 A | 1/1996 | Myers |
| 5,514,158 A | 5/1996 | Kanesaka |
| 5,529,577 A | 6/1996 | Hammerslag |
| 5,550,187 A | 8/1996 | Rhee |
| 5,571,181 A | 11/1996 | Li |
| 5,580,923 A | 12/1996 | Yeung |
| 5,591,205 A | 1/1997 | Fowler |
| 5,601,602 A | 2/1997 | Fowler |
| 5,626,601 A | 5/1997 | Gershony |
| 5,643,464 A | 7/1997 | Rhee |
| 5,700,477 A | 12/1997 | Rosenthal |
| 5,716,375 A | 2/1998 | Fowler |
| 5,718,916 A | 2/1998 | Scherr |
| 5,725,498 A | 3/1998 | Janzen |
| 5,725,551 A | 3/1998 | Myers |
| 5,744,153 A | 4/1998 | Yewey |
| 5,752,974 A | 5/1998 | Rhee |
| 5,780,044 A | 7/1998 | Yewey |
| 5,782,860 A | 7/1998 | Epstein |
| 5,836,970 A | 11/1998 | Pandit |
| 5,868,778 A | 2/1999 | Gershony |
| 5,916,236 A | 6/1999 | Muijs Van de Moer |
| 5,928,266 A | 7/1999 | Kontos |
| 5,948,429 A | 9/1999 | Bell |
| 5,948,829 A | 9/1999 | Wallajapet |
| 5,951,583 A | 9/1999 | Jensen |
| 5,957,952 A | 9/1999 | Gershony |
| 5,972,375 A | 10/1999 | Truter |
| 5,973,014 A | 10/1999 | Funk |
| 6,017,359 A | 1/2000 | Gershony |
| 6,022,361 A | 2/2000 | Epstein |
| 6,048,358 A | 4/2000 | Barak |
| 6,051,248 A | 4/2000 | Sawhney |
| 6,056,768 A | 5/2000 | Cates et al. |
| 6,056,769 A | 5/2000 | Epstein |
| 6,063,061 A | 5/2000 | Wallace |
| 6,083,522 A | 7/2000 | Chu |
| 6,152,943 A | 11/2000 | Sawhney |
| 6,162,240 A | 12/2000 | Cates |
| 6,162,241 A | 12/2000 | Coury |
| 6,165,201 A | 12/2000 | Sawhney |
| 6,179,862 B1 | 1/2001 | Sawhney |
| 6,238,412 B1 | 5/2001 | Dubrul |
| 6,271,278 B1 | 8/2001 | Park |
| 6,287,323 B1 | 9/2001 | Hammerslag |
| 6,302,898 B1 | 10/2001 | Edwards |
| 6,325,789 B1 | 12/2001 | Janzen |
| 6,350,274 B1 | 2/2002 | Li |
| 6,371,975 B2 | 4/2002 | Cruise |
| 6,458,147 B1 | 10/2002 | Cruise |
| 6,475,177 B1 | 11/2002 | Suzuki |
| 6,514,534 B1 | 2/2003 | Sawhney |
| 6,562,059 B2 | 5/2003 | Edwards |
| 6,566,406 B1 | 5/2003 | Pathak |
| 6,569,185 B2 | 5/2003 | Ungs |
| 6,605,294 B2 | 8/2003 | Sawhney |
| 6,608,117 B1 | 8/2003 | Gvozdic |
| 6,610,026 B2 | 8/2003 | Cragg |
| 6,613,070 B2 | 9/2003 | Redmond |
| 6,626,861 B1 | 9/2003 | Hart |
| 6,635,068 B1 | 10/2003 | Dubrul |
| 6,689,148 B2 | 2/2004 | Sawhney |
| 6,699,261 B1 | 3/2004 | Cates et al. |
| 6,703,047 B2 | 3/2004 | Sawhney |
| 6,774,151 B2 | 8/2004 | Malmgren |
| 6,818,008 B1 | 11/2004 | Cates |
| 6,818,018 B1 | 11/2004 | Sawhney |
| 6,860,895 B1 * | 3/2005 | Akerfeldt et al. ............. 606/215 |
| 6,863,924 B2 | 3/2005 | Ranganathan |
| 6,887,974 B2 | 5/2005 | Pathak |
| 6,960,617 B2 | 11/2005 | Omidian |
| 7,331,981 B2 * | 2/2008 | Cates et al. .................... 606/213 |
| 7,335,220 B2 | 2/2008 | Khosravi |
| 7,611,479 B2 | 11/2009 | Cragg et al. |
| 7,621,936 B2 | 11/2009 | Cragg et al. |
| 7,691,127 B2 | 4/2010 | Yassinzadeh et al. |
| 7,803,172 B2 | 9/2010 | Khosravi et al. |
| 7,850,710 B2 | 12/2010 | Huss |
| 7,955,353 B1 | 6/2011 | Ashby et al. |
| 8,382,797 B2 | 2/2013 | Khosravi et al. |
| 8,382,798 B2 | 2/2013 | Khosravi et al. |
| 2001/0031948 A1 | 10/2001 | Cruise |
| 2001/0046518 A1 | 11/2001 | Sawhney |
| 2001/0047187 A1 | 11/2001 | Milo |
| 2001/0051813 A1 | 12/2001 | Hnojewyj |
| 2002/0062104 A1 | 5/2002 | Ashby |
| 2002/0072767 A1 | 6/2002 | Zhu |
| 2002/0106409 A1 | 8/2002 | Sawhney |
| 2002/0188319 A1 | 12/2002 | Morris |
| 2004/0267193 A1 | 12/2004 | Bagaoisan |
| 2004/0267307 A1 | 12/2004 | Bagaoisan |
| 2004/0267308 A1 | 12/2004 | Bagaoisan |
| 2005/0085855 A1 * | 4/2005 | Forsberg ...................... 606/213 |
| 2005/0267522 A1 | 12/2005 | Yassinzadeh et al. |
| 2006/0034930 A1 | 2/2006 | Khosravi |
| 2006/0047313 A1 | 3/2006 | Khanna |
| 2006/0085029 A1 | 4/2006 | Brightbill |
| 2006/0100664 A1 | 5/2006 | Pai et al. |
| 2006/0229673 A1 * | 10/2006 | Forsberg ...................... 606/232 |
| 2006/0265006 A1 * | 11/2006 | White et al. .................. 606/232 |
| 2006/0265007 A1 * | 11/2006 | White et al. .................. 606/232 |
| 2007/0276435 A1 | 11/2007 | Yassinzadeh et al. |
| 2008/0082122 A1 | 4/2008 | Khosravi et al. |
| 2008/0097521 A1 | 4/2008 | Khosravi et al. |
| 2008/0161849 A1 | 7/2008 | Cates et al. |
| 2008/0243182 A1 * | 10/2008 | Bates et al. ................... 606/213 |
| 2009/0216266 A1 * | 8/2009 | Maruyama et al. ........... 606/213 |
| 2009/0270885 A1 * | 10/2009 | Maruyama et al. ........... 606/142 |
| 2010/0168767 A1 | 7/2010 | Yassinzadeh et al. |
| 2010/0168789 A1 | 7/2010 | Bagaoisan et al. |
| 2010/0211000 A1 | 8/2010 | Killion et al. |
| 2010/0286727 A1 * | 11/2010 | Terwey ........................ 606/213 |
| 2011/0046663 A1 * | 2/2011 | Zhou et al. ................... 606/213 |
| 2012/0209321 A1 | 8/2012 | Yassinzadeh et al. |

FOREIGN PATENT DOCUMENTS

| | | |
|---|---|---|
| WO | WO 98/38920 | 9/1998 |
| WO | WO 99/22646 | 5/1999 |
| WO | WO 00/14155 | 3/2000 |
| WO | WO 00/19912 | 4/2000 |
| WO | WO 03/015840 | 2/2003 |
| WO | WO 03/094749 | 11/2003 |
| WO | WO 2004/093690 | 11/2004 |

(56) References Cited

FOREIGN PATENT DOCUMENTS

| WO | WO 2006/052611 | 5/2006 |
|----|----------------|--------|
| WO | WO 2008/033964 | 3/2008 |
| WO | WO 2013/142515 | 9/2013 |

OTHER PUBLICATIONS

Clayman, et al. *Renal Vascular Complications Associated with the Percutaneous Removal of Renal Calculi*, 132, The Journal of Urology, 228-230 (Aug. 1984).

Feliciano, *Abstract: Use of Balloon Catheter Tamponade in Vascular Wounds*, 24(7) The Journal of Trauma 657 (Jul. 1984).

Feliciano, et al., *Balloon Catheter Tamponade in Cardiovascular Wounds*, 160 The American Journal of Surgery 583-87 (Dec. 1990).

Gazelle, et al., *Hemostatic Protein-Polymer Sheath: New Method to Enhance Hemostasis at Percutaneous Biopsy*, 175 Radiology 671-74 (Jun. 1990).

Gross, *A Manual of Military Surgery*, Chapter V: Wounds and other injuries, 53-55 (1861).

Kaye, et al. *Tamponade Nephrostomy Catheter for Percutaneous Nephrostolithotomy*, 27(5) Urology 441-45 (May 1986).

PCT International Search Report and Written Opinion for PCT/US2007/078328; Applicant: Accessclosure, Inc. et al; Forms PCT/ISA/210, PCT/ISA/237, and PCT/ISA/220; mailed Jul. 7, 2008, 15 pages.

Pfab, et al., *Animal Experiments on Hemostasis with a Collagen-Fibrin Tissue-Adhesive Sealant in the Nephrostomy Tract*, 42 Urology International 207-09 (1987).

Pfab, et al., *Local Hemostasis of Nephrostomy Tract with Fibrin Adhesive Sealing in Percutaneous Nephrolithotomy*, 13 European Urology 118-21 (1987).

Riley, et al., *Percutaneous Liver Biopsy with Plugging of Needle Track: A Safe Method for Use in Patients with Impaired Coagulation*, The Lancet 436 (Aug. 1984).

Smiley, et al. *Balloon Catheter Tamponade of Major Vascular Wounds*, 121 The American Journal of Surgery 326-27 (Mar. 1971).

Takayasu, et al., *A New Hemostatic Procedure for Percutaneous Transhepatic Portal Vein Catheterization*, 18(3) Japanese Journal of Clinical Oncology 227-30 (Sep. 1988).

International Search Report and Written Opinion for PCT/US2013/033006 mailed Jul. 18, 2013 in 15 pages.

\* cited by examiner

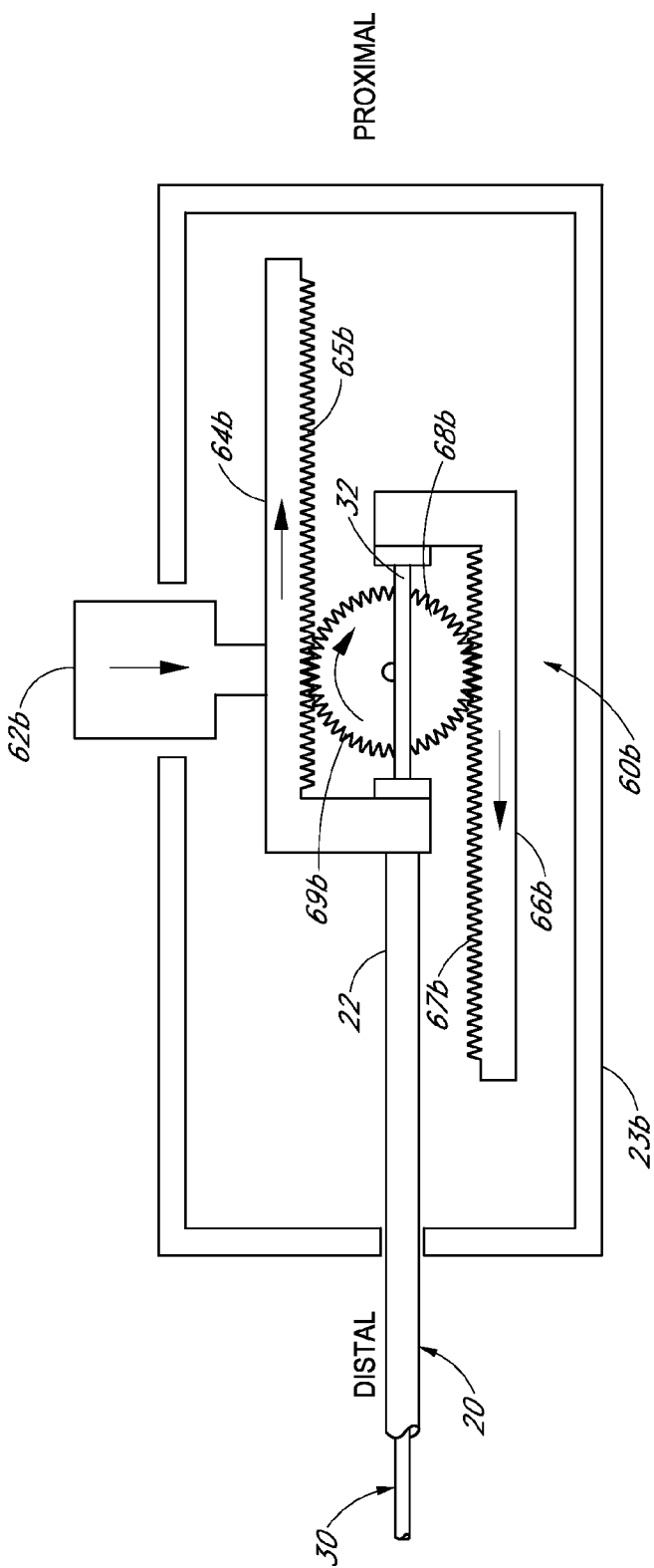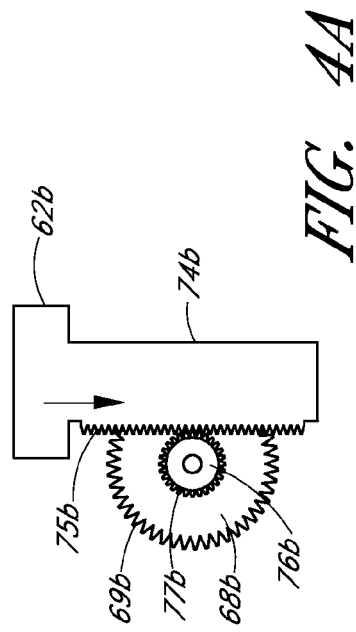
FIG. 4
FIG. 4A

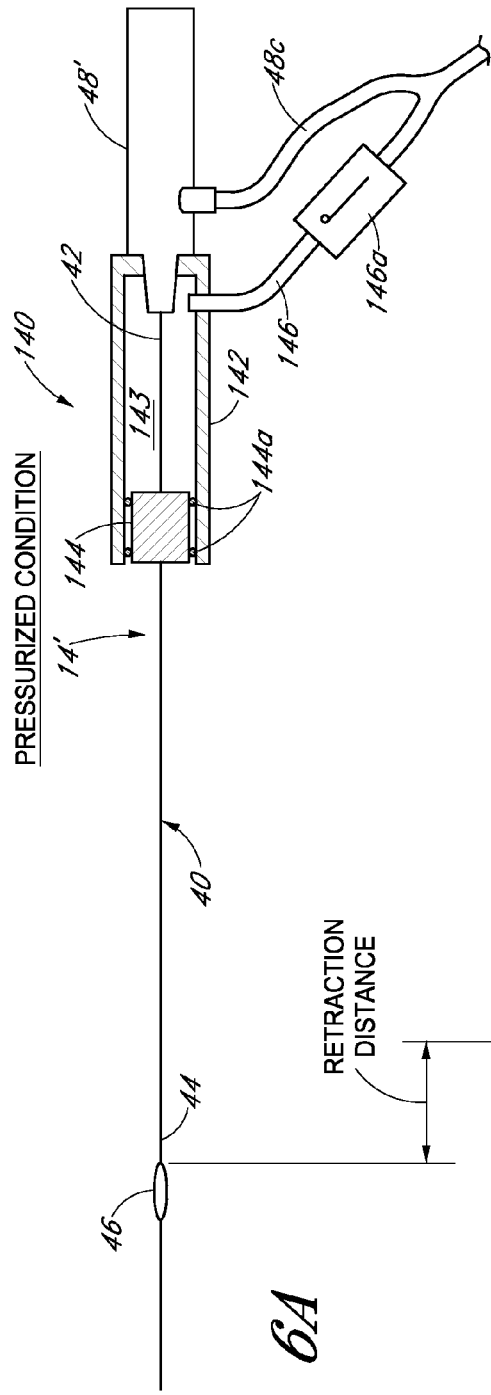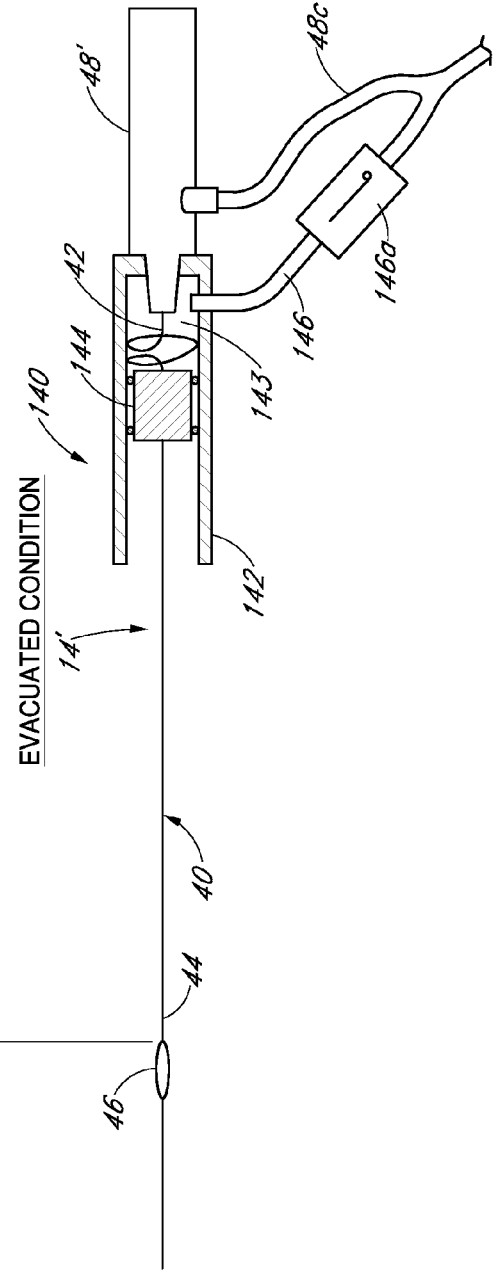

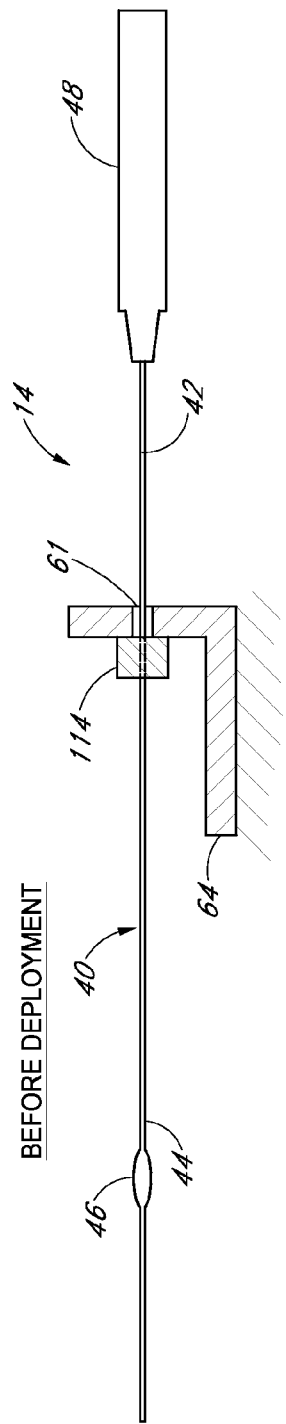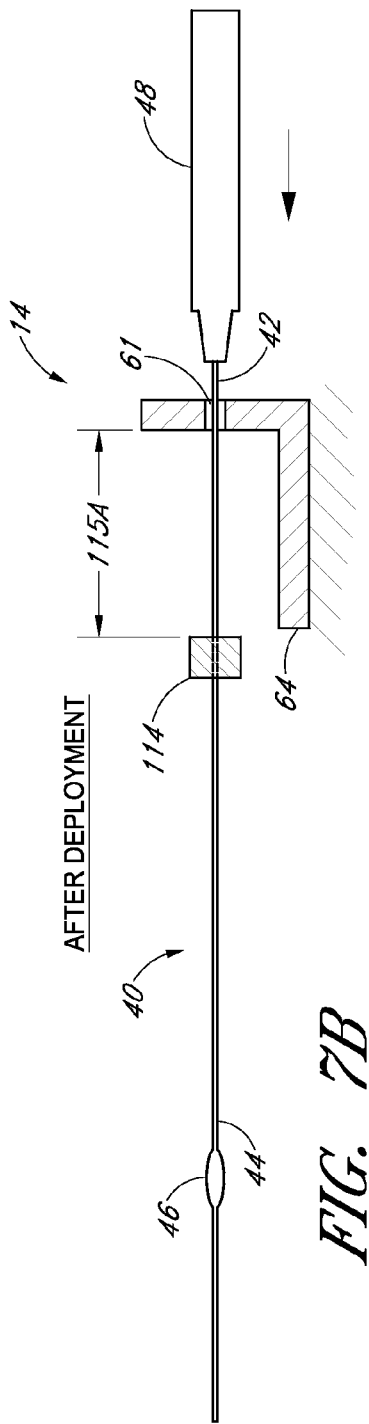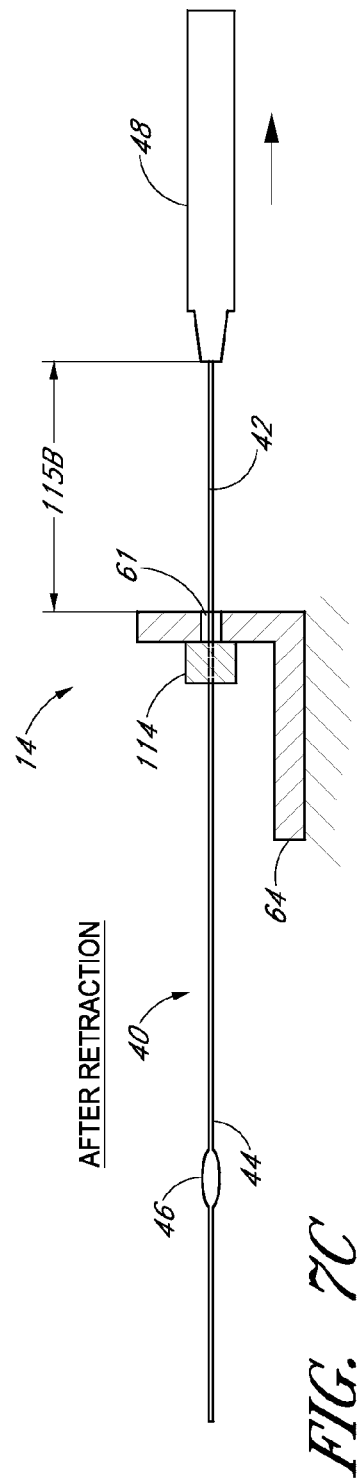

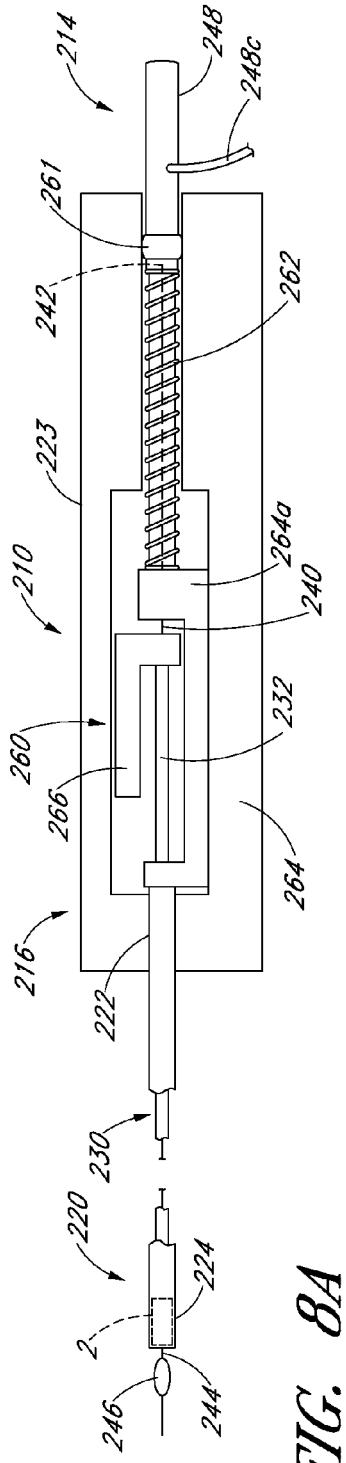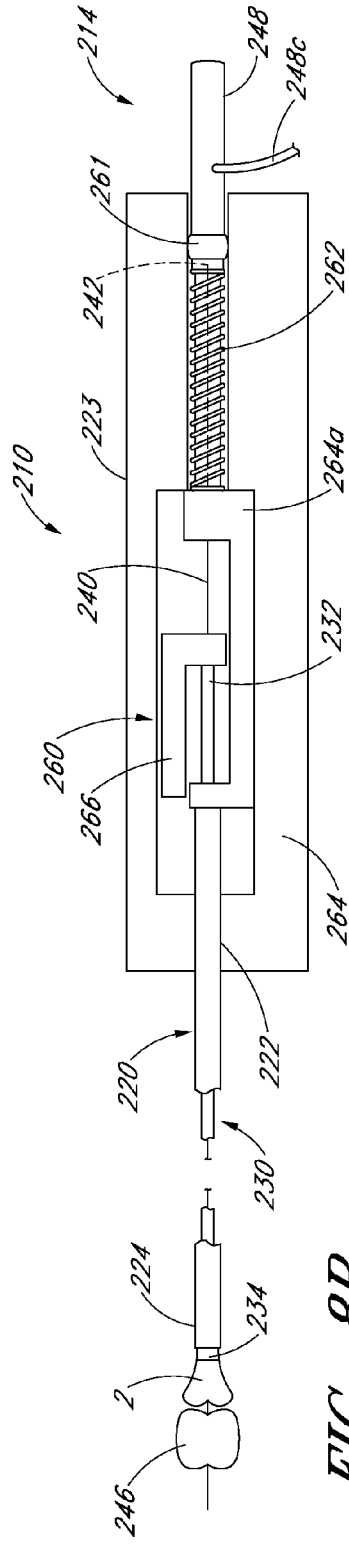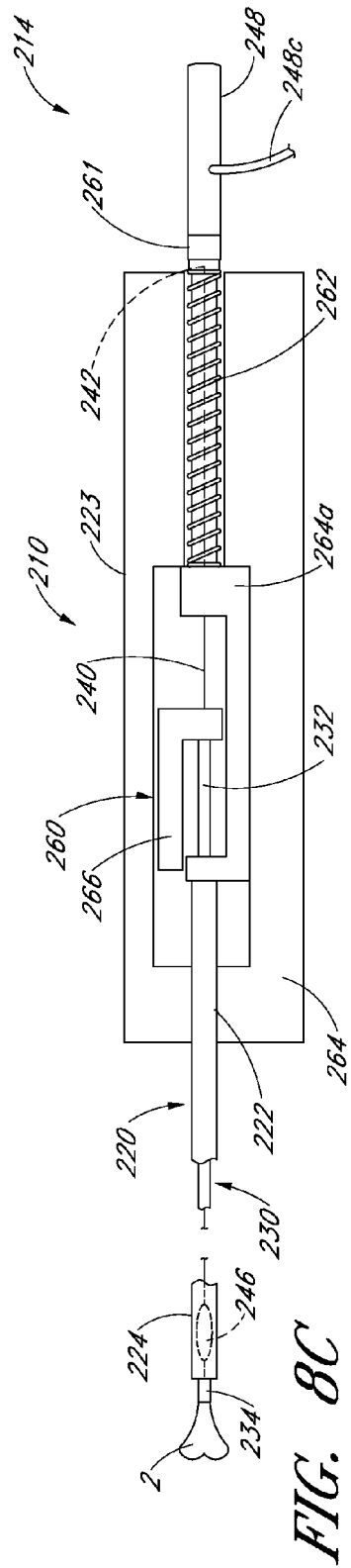

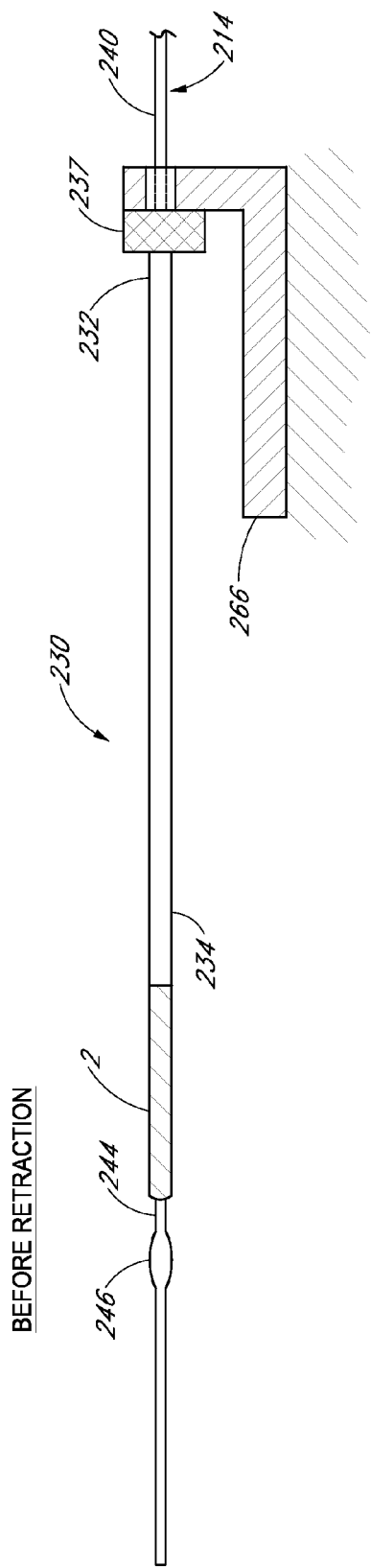
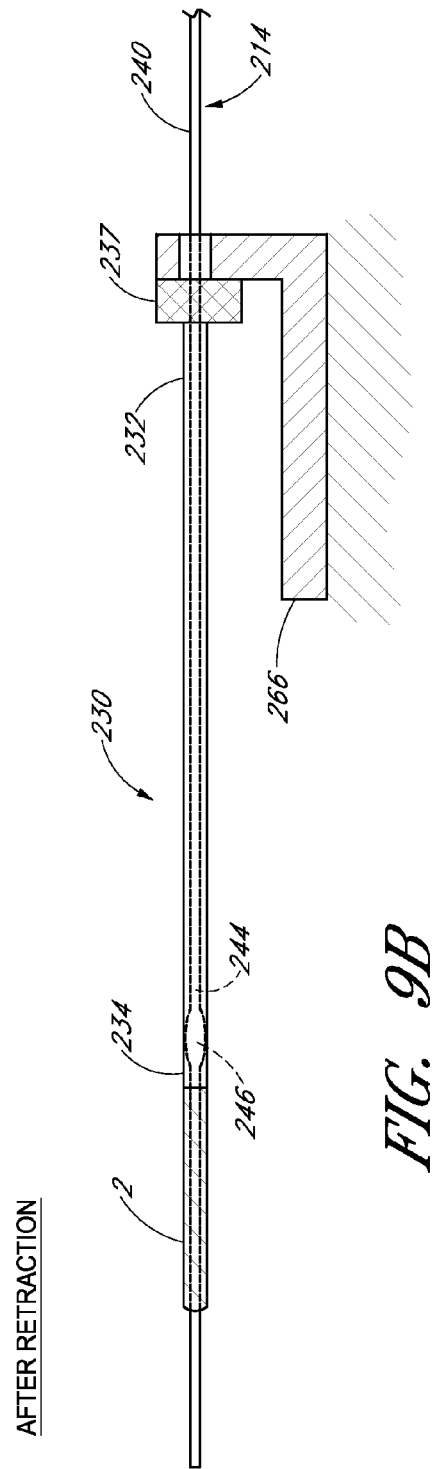

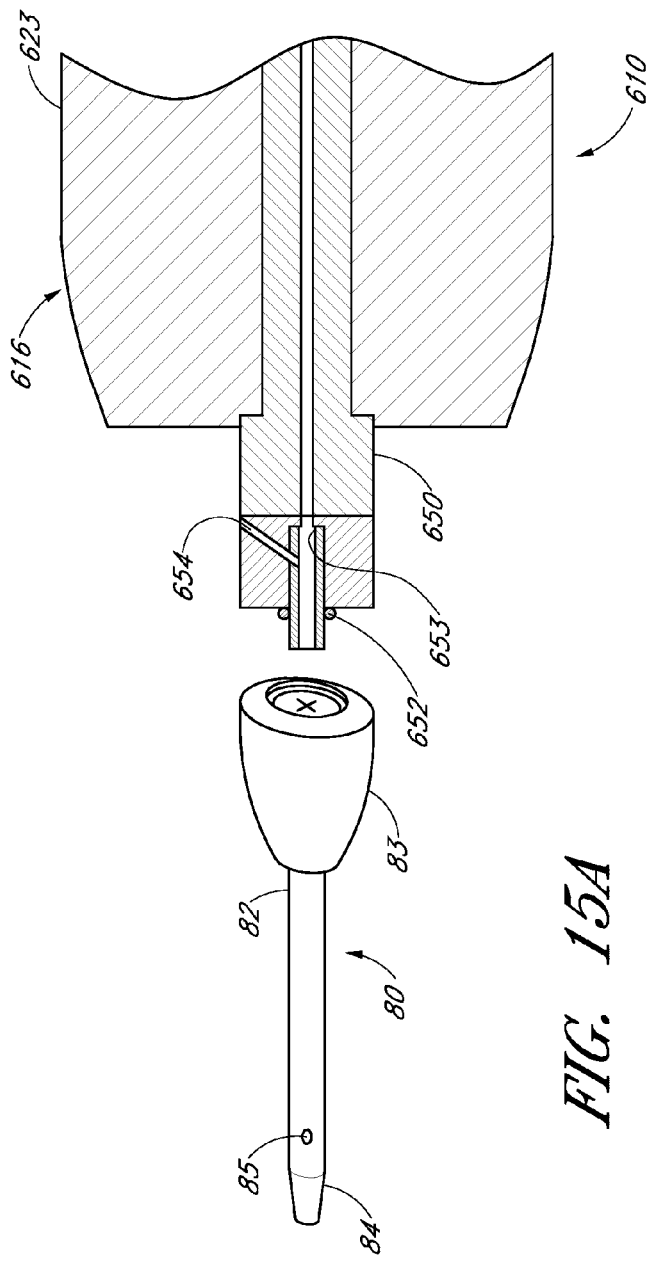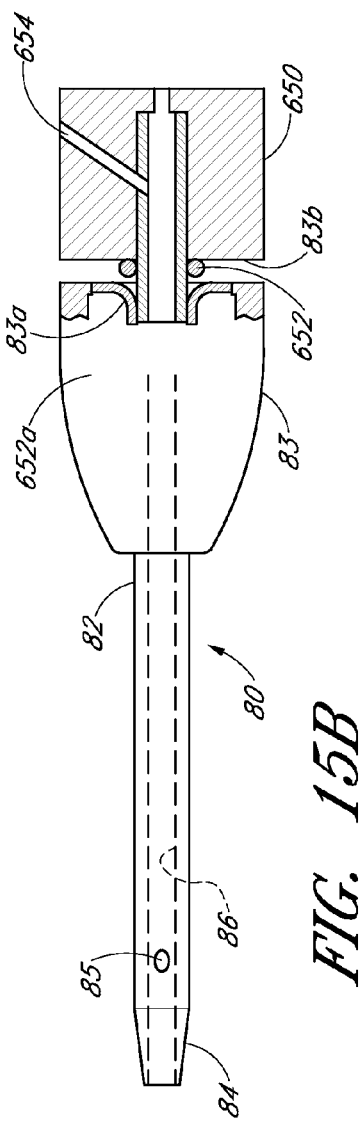
FIG. 15A
FIG. 15B

APPARATUS AND METHODS FOR SEALING A VASCULAR PUNCTURE

CROSS-REFERENCE TO RELATED APPLICATIONS

This present application claims priority benefit under 35 U.S.C. §119(e) to U.S. Provisional Application No. 61/615,202, filed Mar. 23, 2012, entitled "APPARATUS AND METHODS FOR SEALING A VASCULAR PUNCTURE," which is hereby incorporated by reference in its entirety.

BACKGROUND

1. Field

The present invention relates generally to apparatus and methods for sealing punctures in a body, and more particularly, to apparatus and methods for sealing a vascular puncture extending through tissue into a blood vessel, and to apparatus and methods for delivering a plug, sealant, and/or other material into a percutaneous puncture extending from a patient's skin to a blood vessel or other body lumen, e.g., to seal the puncture.

2. Description of the Related Art

Apparatus and methods are known for accessing a patient's vasculature percutaneously, e.g., to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer sheath may then be advanced over the guide wire into the vessel, e.g., in conjunction with or subsequent to one or more dilators.

A catheter or other device may be advanced through the introducer sheath and over the guide wire into a position for performing a medical procedure. Thus, the introducer sheath may facilitate accessing and/or introducing various devices into the vessel, while minimizing trauma to the vessel wall and/or minimizing blood loss. Upon completing the procedure, the device(s) and introducer sheath may be removed, leaving a puncture extending between the skin and the vessel wall.

To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient, and may require the patient to remain immobilized in the operating room, catheter lab, or holding area. In addition, a risk of hematoma exists from bleeding before hemostasis occurs.

Various apparatus and methods have been suggested for sealing vascular punctures resulting from such procedures, such as those disclosed in U.S. Pat. Nos. 7,316,704, 7,331,979, 7,335,220, and 7,806,856, and U.S. Publication Nos. 2007/0231366, 2008/0082122, 2009/0088793, 2009/0254110, 2010/0168789, 2010/0274280, and 2010/0280546. The entire disclosures of these references are expressly incorporated by reference herein.

For example, the MATRIX™ product included two synthetic polyethylene glycol ("PEG") polymer powders that were mixed with appropriate buffers and injected through a femoral sheath at an arteriotomy site, e.g., as disclosed in U.S. Pat. No. 7,316,704. The MYNX® Vascular Closure Device is another system for sealing vascular punctures, e.g., as disclosed in one or more of the references identified above, such as U.S. Pat. No. 7,335,220.

Accordingly, apparatus and methods for sealing a puncture through tissue would be useful.

SUMMARY

The present application is directed to apparatus and methods for sealing a puncture in a body. More particularly, the present application is directed to apparatus and methods for providing temporary or permanent hemostasis within a vascular puncture extending into a blood vessel, and/or to apparatus and methods for delivering a sealant and/or other material into a percutaneous puncture extending from a patient's skin to a blood vessel or other body lumen.

In accordance with an exemplary embodiment, an apparatus is provided for sealing a puncture extending through tissue having an introducer sheath therein that includes a proximal end including a hub, a distal end, and a lumen extending therebetween. Generally, the apparatus may include a positioning member including proximal and distal ends, and an expandable positioning element on the distal end; a sealant carried on the positioning element distal end adjacent the positioning element; a support member including proximal and distal ends, the support member distal end on the positioning member distal end adjacent the sealant; and a sealant sleeve slidably disposed over the support member distal end and covering the sealant. The sleeve may include a portion that abuts the introducer sheath hub when the positioning member distal end is introduced into the introducer sheath to prevent the entire sleeve from entering the introducer sheath lumen such that, when the positioning member is advanced into the introducer sheath lumen the sealant and support member are exposed within the introducer sheath lumen, and further advancement of the positioning member causes the support member to direct the sealant distally through the introducer sheath lumen.

In accordance with another embodiment, a system is provided for sealing a puncture extending through tissue that includes an introducer sheath comprising a proximal end including a hub, a distal end, and a lumen extending therebetween; and a positioning member comprising proximal and distal ends, and an expandable positioning element on the distal end, the positioning member distal end sized to be introduced into the sheath hub and lumen with the positioning element in a collapsed condition. A sealant may be carried on the positioning element distal end adjacent the positioning element, and a support member including proximal and distal ends may be carried on the positioning member such that the support member distal end is disposed on the positioning member distal end adjacent the sealant. A sealant sleeve may be slidably disposed over the support member distal end and covering the sealant. The sleeve may include a portion that abuts the introducer sheath hub when the positioning member distal end is introduced into the introducer sheath to prevent the entire sleeve from entering the introducer sheath lumen such that, when the positioning member is advanced into the introducer sheath lumen the sealant and support member are exposed within the introducer sheath lumen, and further advancement of the positioning member causes the support member to direct the sealant distally through the introducer sheath lumen.

In accordance with still another embodiment, a method is provided for sealing a puncture extending through tissue to a body lumen, the puncture having an introducer sheath therein. An elongate positioning member may be provided including proximal and distal ends, and a sleeve at least partially surrounding a sealant and a distal end of a support member, the sleeve and sealant disposed adjacent a positioning element on the positioning member distal end. The positioning member distal end may be advanced into a hub and lumen of the introducer sheath until the sleeve contacts the sheath hub. The positioning member may be advanced further through the sheath lumen until the positioning element is disposed within the body lumen beyond a distal end of the introducer sheath, thereby causing the sleeve to slide over the support member to expose the sealant within the sheath lumen and advancing the support member distal end into the introducer sheath lumen to direct the sealant through the introducer sheath lumen towards the sheath distal end. The introducer sheath may then be retracted to expose the sealant within the puncture.

In accordance with one embodiment, an apparatus is provided for sealing a puncture that includes an elongate positioning member including a proximal end and an expandable positioning element on a distal end thereof, and a cartridge advanceable along the positioning member from a proximal position adjacent the proximal end to a distal position. The cartridge may include a tubular member, a sealant disposed within a lumen of the tubular member, e.g., adjacent a distal end of the tubular member, a support member disposed within the tubular member lumen adjacent the sealant, and a housing on a proximal end of the tubular member.

A deployment mechanism within the housing that is coupled to the tubular member and support member, e.g., including one or more rack and pinion elements coupled to proximal ends of the tubular member and support member. An actuator is provided on the housing that is coupled to the deployment mechanism such that, when activated, the tubular member is directed proximally and/or the support member is directed distally in a predetermined sequence. For example, the actuator may be activated to direct one or more rack and pinions to sequentially a) withdraw the tubular member relative to the sealant for exposing the sealant from the tubular member lumen within a puncture and b) advance the support member to compress the sealant within the puncture. The timing of the retraction and advancement may be set based on the configuration of the deployment mechanism, e.g., to delay advancement of the support member until the sealant is substantially exposed from the tubular member.

In accordance with another embodiment, a system is provided for sealing a puncture through tissue that generally includes an introducer sheath, a positioning member, and a cartridge. The introducer sheath may include a proximal end including a hub, a distal end sized for introduction into a puncture, and a lumen extending therebetween. The positioning member may include an elongate member including a proximal end and an expandable positioning element on a distal end thereof. The cartridge may be advanceable along the positioning member from a proximal position to a distal position, and may include a tubular member including a sealant and a support member disposed within lumen of the tubular member. A locking mechanism may be provided on the cartridge for engaging the hub of the introducer sheath when the tubular member is advanced to the distal position and enters the introducer sheath, e.g., thereby coupling subsequent proximal movement of the tubular member and introducer sheath to one another.

In accordance with still another embodiment, an apparatus is provided for sealing a puncture extending through tissue having an introducer sheath therein that includes a proximal end including a hub, a distal end, and a lumen extending therebetween. The apparatus can include a positioning member including proximal and distal ends and an expandable positioning element on the distal end, and a cartridge advanceable along the positioning member from a proximal position adjacent the positioning member proximal end to a distal position. The cartridge may include a sealant, a support member including a distal end disposed adjacent the sealant, and a sealant sleeve slidably disposed over the support member distal end and covering the sealant.

The sleeve may include a distal portion sized to enter the introducer sheath hub when the cartridge is advanced towards the distal position and a proximal portion that abuts the introducer sheath hub to prevent the entire sleeve from entering the introducer sheath lumen such that, when the cartridge is advanced from the proximal position to the distal position, the sleeve distal portion enters the introducer sheath lumen while the sleeve is stopped by the introducer sheath hub and slides over the support member to expose the sealant within the introducer sheath lumen, and further advancement of the cartridge to the distal position causes the support member to direct the sealant distally through the introducer sheath lumen.

Certain aspects of this disclosure are directed toward an apparatus for sealing a puncture through a vessel wall. The apparatus can include a positioning assembly including a positioning element positioned at a distal portion of the positioning assembly and a sealant disposed at a distal portion of the positioning assembly. The apparatus can include a sheath releasably engaged with the positioning assembly. The apparatus can include a support member axially advanceable through the sheath.

Certain aspects of this disclosure are directed toward an apparatus for sealing a puncture through a vessel wall. The apparatus can include a positioning assembly including a sealant disposed at a distal portion of the positioning assembly. The apparatus can include a sheath through which the positioning assembly is axially advanceable. The apparatus can include a handle having an outer handle portion configured to move relative to an inner housing portion. The outer handle portion can be removably coupled to the sheath.

Any of the apparatus features, methods, or processes disclosed in the specification can be included in any of the embodiments. For example, the positioning assembly can include a sealant sleeve at least partially surrounding the sealant. The sheath can include a hub portion configured to receive the sealant sleeve. An inner diameter of the sheath can be smaller than an outer diameter of the sealant sleeve. The sealant can include a first sealant portion distal to a second sealant portion. The first sealant portion can be different from the second sealant portion.

In certain aspects, the apparatus can include a positioning element configured to move between an unexpanded state and an expanded state. The positioning element can be positioned at a distal portion of the positioning assembly.

In certain aspects, the handle can include a first actuator configured to prevent relative movement of the outer handle portion and the inner handle portion. The handle can include a second actuator configured to advance a support member. The handle can include third actuator configured to move the positioning element proximally.

Certain aspects of this disclosure are directed toward a method for sealing a puncture through a vessel wall. The method can include advancing a sheath over a guide wire. The method can include withdrawing the guide wire. The method can include advancing a positioning assembly through the sheath such that a positioning element enters the vessel. The positioning assembly can carry a sealant disposed at a distal portion of the positioning assembly. The method can include retracting the sheath to expose the sealant outside of the vessel.

Any of the apparatus features, methods, or processes disclosed in the specification can be included in any of the method embodiments. For example, the method can include expanding the positioning element inside the vessel. The method can include proximally retracting the positioning element to seat the positioning element against the vessel wall. The method can include releasably engaging the positioning assembly and the sheath. The method can include releasing the positioning assembly from the sheath. The method can include advancing a support member to tamp the sealant. The method can include retracting the positioning element through the sealant, leaving the sealant in place. In certain aspects, advancing the positioning assembly can include transferring the sealant from a sealant sleeve to the sheath. The method can include advancing a dilator through the sheath.

Other aspects and features of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments.

FIG. 4 is a cross-sectional view of still another alternative embodiment of a deployment mechanism, including a push button actuator.

FIG. 4A is a detail of an actuator-pinion arrangement that may be included in the deployment mechanism of FIG. 4.

FIGS. 6A and 6B are partial cross-sectional side views of another embodiment of a positioning member including an auto-retraction assembly for automatically retracting the positioning member when activated.

FIGS. 7A-7C are side views of an alternative embodiment of a positioning member including a retraction lock that limits movement of the positioning member relative to a cartridge (only a first rack of the cartridge is shown simply for clarity).

FIGS. 8A-8C are partial cross-sectional side views of yet another embodiment of an apparatus including a positioning member and a cartridge carrying a sealant that includes an auto-retraction mechanism for retracting the positioning member relative to the cartridge.

FIGS. 9A and 9B are details showing a collapsed positioning element being retracted through exposed sealant into a cartridge.

FIGS. 15A and 15B are partial cross-sectional side views of another exemplary embodiment of a sheath that may be provided on an apparatus including a bleed back port.

DETAILED DESCRIPTION

Figure 1A:
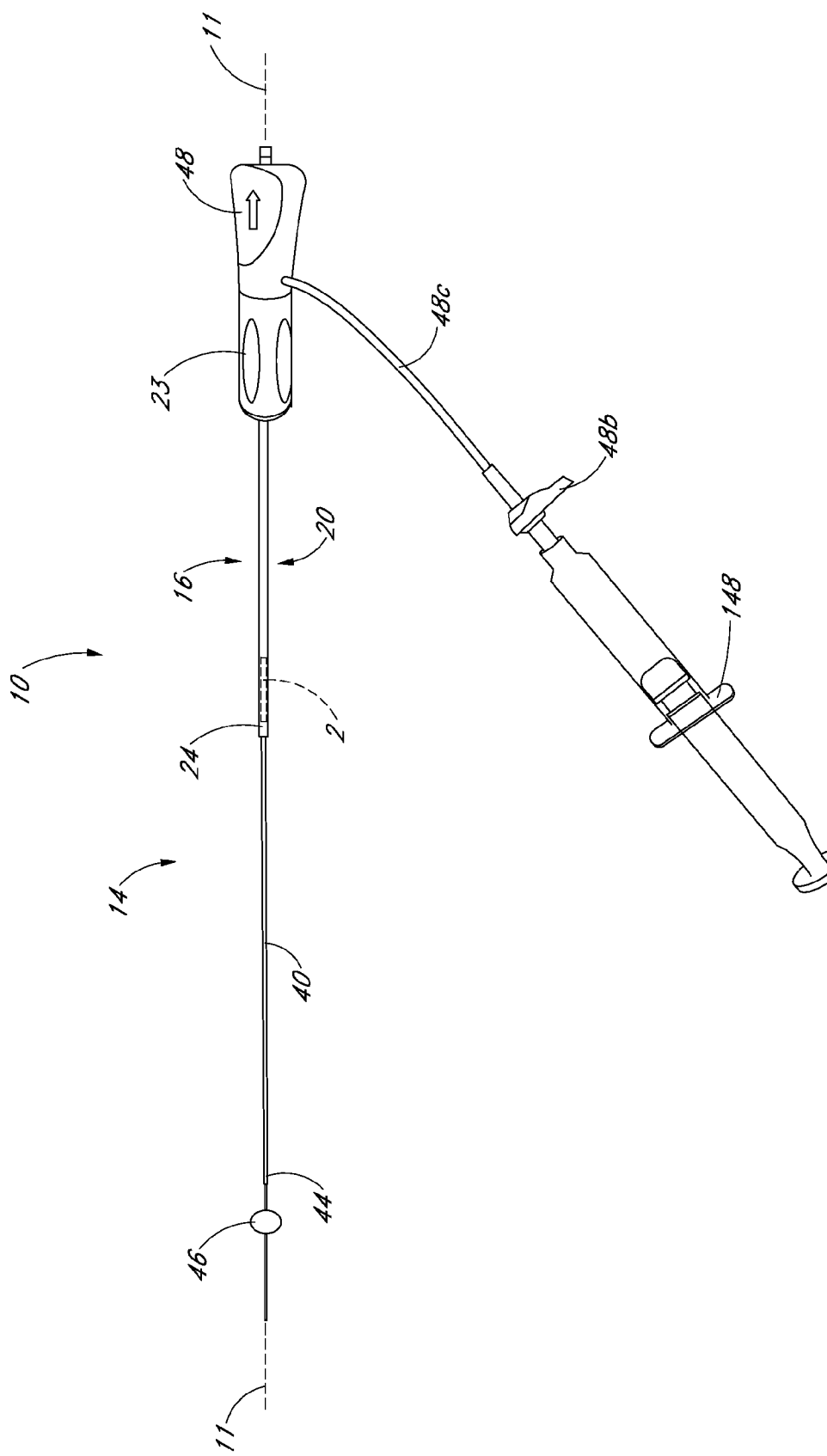
FIG. 1A is a side view of an exemplary embodiment of an apparatus for delivering a sealant into a puncture through tissue, including a positioning member, and a cartridge movable over the positioning member that includes the sealant.
Figure 1B:
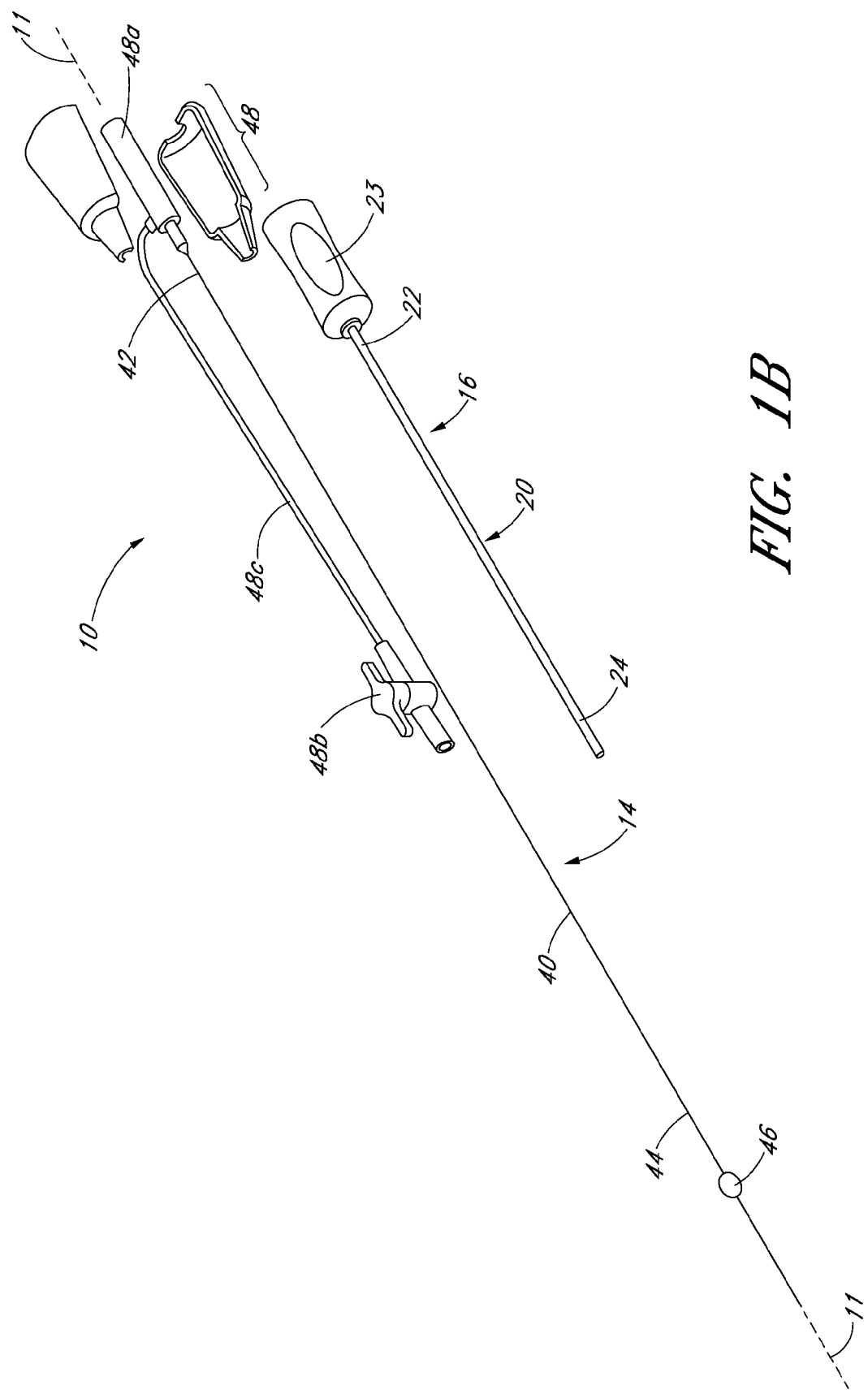
FIG. 1B is an exploded perspective view of the apparatus of FIG. 1A.

Turning to the drawings, FIGS. 1A-2B show an exemplary embodiment of an apparatus 10 for sealing a puncture through tissue that generally includes a positioning member 14 and a cartridge or shuttle 16 carried on the positioning member 14 for delivering a sealant 2 therein into a puncture (not shown). The cartridge 16 can include an elongate tubular member 20 carrying the sealant 2 therein, a support tube or member 30 adjacent the sealant 2 within the tubular member 20, and a handle or housing 23 coupled to and/or carried by the tubular member 20 and/or support member 30.

Figures 10A, 10B:
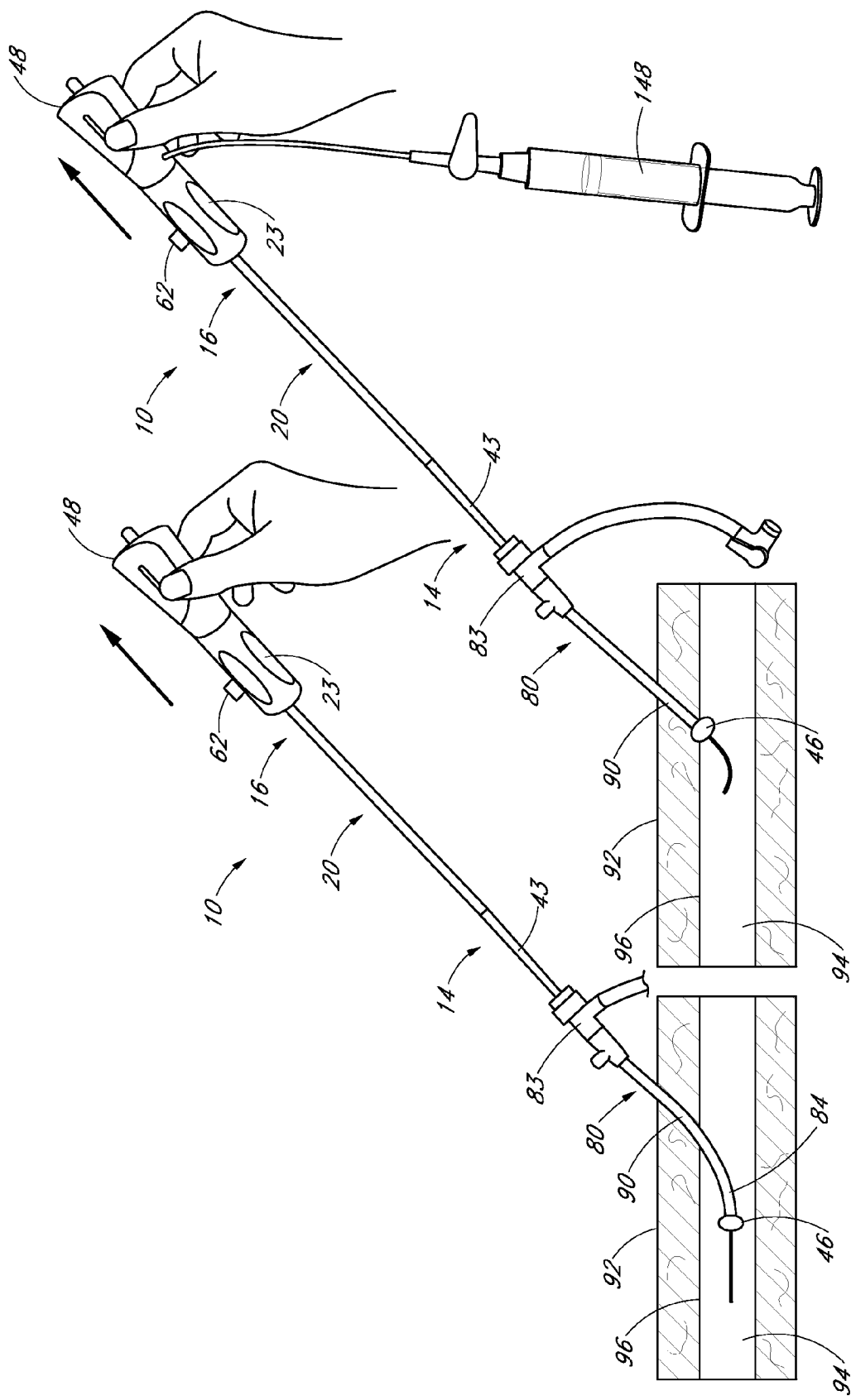
FIGS. 10A-10G are cross-sectional views of a patient's body showing a method for sealing a puncture using the apparatus of FIGS. 1A-2B.
Figure 10C:
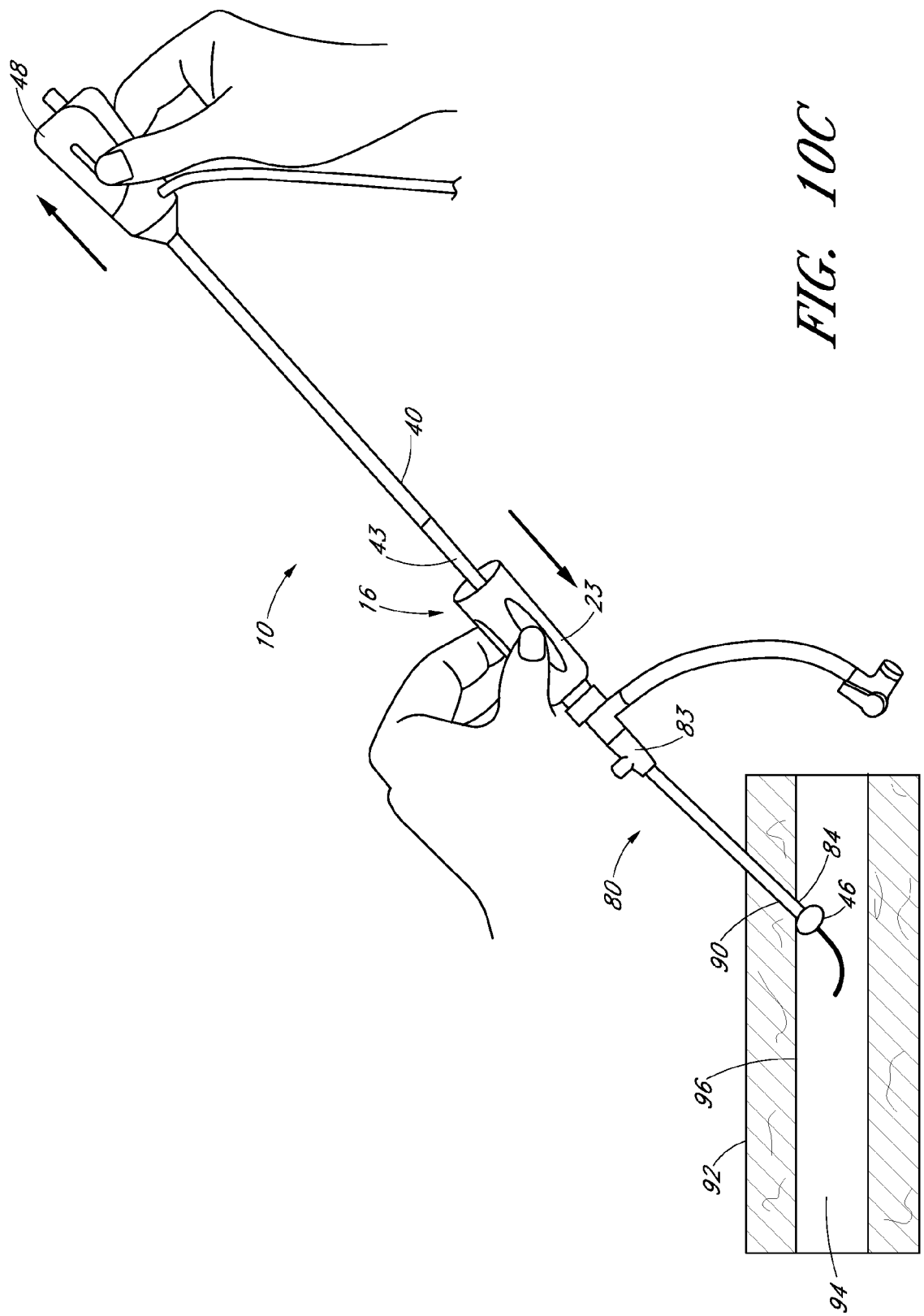

As shown in FIGS. 1A-2A, the cartridge 16 may be provided initially in a proximal position, e.g., where the sealant is spaced proximally away from an expandable positioning element 46 on the positioning member 14. The entire cartridge 16 may be advanceable from the proximal position to a distal position, e.g., as shown in FIGS. 10A-10C, to advance the sealant 2 into a puncture and/or towards the positioning element 46. In certain aspects, the relative lengths of the positioning member 14 and cartridge 16 may be such that the sealant 2 is disposed adjacent the positioning element 46 in an initial position, e.g., such that the entire cartridge 16 is not advanced from a proximal position to a distal position, e.g., similar to the apparatus 210 shown in FIGS. 8A-8C and/or the apparatus 710 shown in FIGS. 16A and 16B, and as described further elsewhere herein.

Figure 2A:
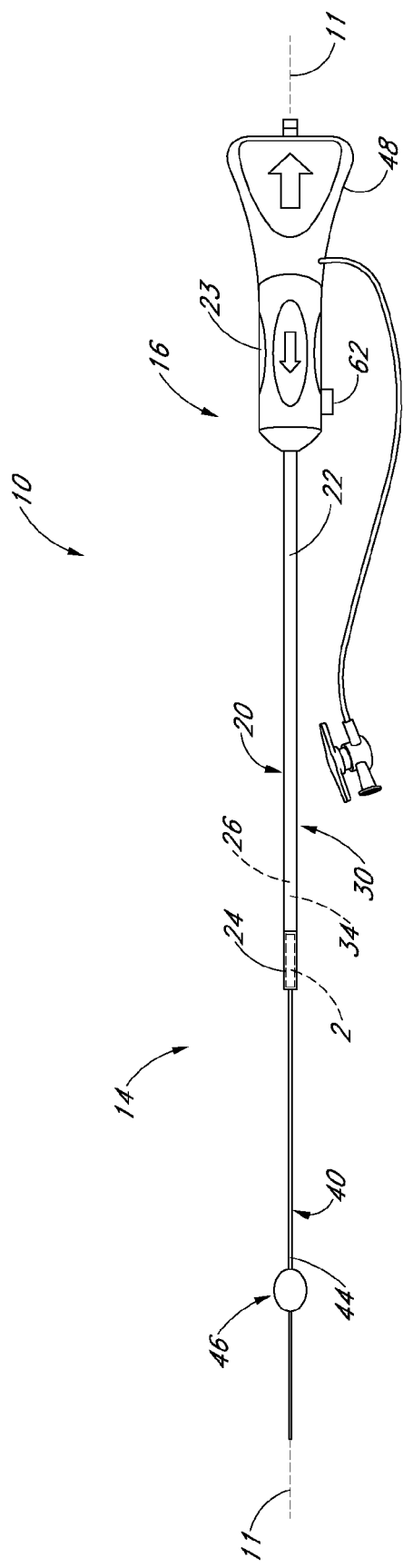
FIG. 2A is a side view of the apparatus of FIGS. 1A and 1B showing a sealant and support member (in phantom) within an outer tubular member of the cartridge.
Figure 2B:
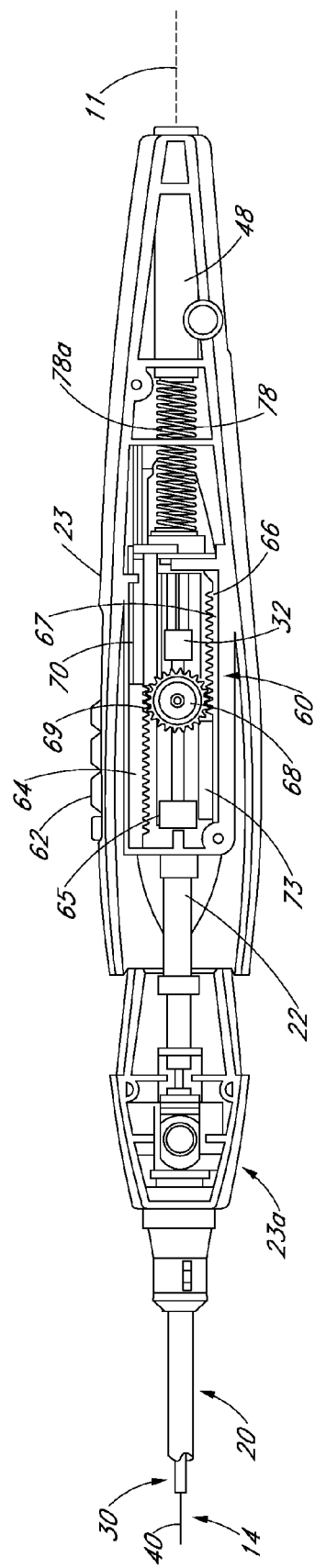
FIG. 2B is a cross-sectional view of an exemplary embodiment of a housing that may be provided on the proximal end of the cartridge of FIGS. 1A-2A, showing a deployment mechanism therein for deploying the sealant from the cartridge.

As shown in FIG. 2B, the cartridge 16 can include a deployment mechanism 60 within the housing 23 coupled to the tubular member 20 and support member 30. As described further below, the deployment mechanism 60 may be configured for directing the tubular member 20 and/or support member 30 axially relative to the housing 23, and consequently relative to the sealant 2 and/or positioning member 14, e.g., to deploy and/or compress the sealant 2.

Optionally, the apparatus 10 (or any of the other embodiments herein) may be part of a system, e.g., which may also include a delivery, access, procedure, introducer, or other sheath 80 (not shown, see, e.g., FIGS. 10A-10F). The introducer sheath 80 may be a conventional sheath 80, e.g., as shown in FIGS. 10A-10F, or may be a custom sheath, such as the sheath 780 shown in FIG. 16C, e.g., including bleed back and/or sheath lock features, as described further below. Optionally, the apparatus 10 and/or system may include one or more other components, e.g., a needle, guidewire, and/or other instrument for creating a puncture, a source of inflation media, and/or a source of additional sealing compound (not shown), for example, to provide a kit for a medical procedure.

Generally, as best seen in FIG. 2A, the tubular member 20 can include a proximal end 22 extending into and/or coupled to the housing 23 and/or deployment mechanism 60, a distal end 24 sized for introduction into an introducer sheath and/or puncture (not shown), and a lumen 26 extending between proximal and distal ends 22, 24. The tubular member 20 may be substantially rigid, semi-rigid, or flexible, e.g., such that the tubular member 20 may be advanced through an introducer sheath or otherwise into a puncture through tissue. The distal end 24 may terminate in a tapered, rounded, or blunt distal tip. Optionally, similar to other embodiments described further below, the distal end 24 may terminate in a collapsible, splittable, or crushable distal tip (not shown).

With additional reference to FIGS. 2A and 2B, the support member 30 may be an elongate tubular body sized to be slidably received within the lumen 26 of the tubular member 20. The support member 30 may include a proximal end 32 extending into and/or coupled to the housing 23 and/or the deployment mechanism 60, and a distal end 34 disposed proximal to the tubular member distal end 24 and/or adjacent the sealant 2, for example, to facilitate contacting and/or otherwise maintaining the sealant 2 within a puncture, e.g., when the tubular member 20 is retracted during use, as described further below. The support member 30 may also include a lumen (not shown) extending between the proximal and distal ends 32, 34, e.g., to accommodate slidably receiving the positioning member 14 therethrough.

The support member 30 may be substantially rigid, semi-rigid, and/or substantially flexible, e.g., having sufficient column strength to allow proximal movement of the tubular member 20 relative to the sealant 2 without buckling the support member 30 and/or to allow the distal end 34 of the support member 30 to be advanced to compress the sealant 2 within a puncture, e.g., by pushing from the proximal end 32 by the deployment mechanism 60, as described further below.

As shown in phantom in FIG. 2A, the sealant 2 may be disposed within the lumen 26 of the tubular member 20 proximate to the distal end 24, e.g., immediately adjacent and/or surrounded by the distal tip. The lumen 26 may be sized such that the tubular member 20 and sealant 2 are slidable relative to one another, e.g., to allow the tubular member 20 to be retracted proximally relative to the sealant 2 and/or support member 30, as described further below. In an exemplary embodiment, the sealant 2 may include a first, proximal, or main section 2a formed from freeze-dried hydrogel, and a second, distal, or tip section 2b (not shown, see, e.g., FIG. 11) formed from a plurality of non-freeze-dried and/or non-crosslinked precursors, e.g., formed as a solid mass or solid plug, fused or otherwise attached to and extending distally from the first section, e.g., as disclosed in U.S. application Ser. No. 13/354,278, filed Jan. 19, 2012, the entire disclosure of which is expressly incorporated by reference herein.

The sealant 2 may include one or more biocompatible, bioabsorbable, and/or expandable materials, such as a freeze-dried hydrogel. The sealant 2 may have a solid or hollow cylindrical shape, a rolled sheet shape, a disk shape, or other shapes or cross-sections, such as elliptical, triangular, square, conical, disk, polygonic shapes. For example, the sealant 2 may be formed from a solid material including a lumen (not shown) extending between proximal and distal ends thereof. The lumen may be created by rolling a sheet of material around a mandrel, by molding, by boring into or otherwise removing material from an already formed solid material, and the like. The lumen may be dimensioned such that the positioning member 14 or other instrument (not shown) may slide or otherwise pass through the sealant 2, as described in the references identified in Ser. No. 13/354,278, the entire disclosures of which are expressly incorporated by reference herein.

In some embodiments, the sealant 2 may be formed from a biocompatible and/or bioabsorbable hydrogel, e.g., polyethylene glycol ("PEG"). For example, the hydrogel may include a freeze-dried PEG polymer that includes hydrolytically degradable chemical groups, e.g., including a macroporous polymer network, which may uptake fluid and expand when exposed to an aqueous environment. The magnitude of expansion or swelling (pre to post hydration) may be significant, e.g., between about two and ten times (2×-10×) its freeze-dried size based on volume. In addition or alternatively, the sealant 2 may include pro-thrombotic material, e.g., including one or more biological pro-thrombotics, such as collagen, fibrin, carboxymethylcellulose, oxidized cellulose, alginates, gelatin, or other protein-based material, and/or synthetic materials, such as polyglycolic acids (PGA's), polylactides (PLA's), polyvinyl alcohol, and the like.

Optionally, the sealant 2 may include one or more therapeutic and/or pharmaceutical agents, e.g., to promote healing, prevent infection and/or other adverse medical events, and the like. Such agents may be embedded in the sealant material and/or applied as one or more coatings or layers. In addition or alternatively, the sealant 2 may be substantially homogeneous, or may include one or more different materials at one or more locations. For example, in some embodiments, the sealant 2 may include a carrier or core having first and second hydrogel precursors disposed thereon in an unreactive state, which may provide an adherent coating when the sealant 2 is exposed to an aqueous environment.

Turning to FIG. 2B, the housing 23 may include an actuator 62 coupled to the deployment mechanism 60 therein, e.g., for selectively directing the tubular member 20 and/or support member 30 to expose and/or compress the sealant 2. In an exemplary embodiment, the deployment mechanism 60 may include one or more rack and pinion elements coupled together in a desired arrangement to cause the tubular member 20 and support member 30 to retract and/or advance in a predetermined sequence.

For example, as shown in FIG. 2B, the deployment mechanism 60 can include a first rack 64 coupled to the proximal end 22 of the tubular member 20, a second rack 66 coupled to the proximal end 32 of the support member 30, and a pinion 68 coupled between the first and second racks 64, 66. In an exemplary embodiment, the proximal ends 22, 32, may be attached to the racks 64, 66, e.g., by providing stems (not shown) on the racks 64, 66 that are received within the proximal ends 22, 32, and/or by bonding, fusing, sonic welding the proximal ends 22, 32 to the stems or directly to the racks 64, 66.

The pinion 68 may be translationally fixed relative to the housing 23, e.g., such that the pinion 68 is free to rotate about an axle fixed to the housing 23 without substantial translational motion along or transverse to a longitudinal axis 11 of the apparatus 10. The racks 66, 68 may be slidably mounted within the housing 23, e.g., along tracks, rails, slots, and the like 70, 72, such that the racks 66, 68 may slide within the housing substantially parallel to the longitudinal axis 11. Motion of the racks 64, 66 may be limited by the tracks and/or by movement of the actuator 62 and/or interaction with the pinion 68, e.g., to limit the distance that the tubular member 20 and support move 30.

Generally, the racks 64, 66 and pinion 68 can include cooperating teeth that interact with one another such that movement of one of the elements causes desired movement in the other elements. For example, as shown, the pinion 68 includes a continuous, substantially uniformly sized and spaced teeth 69 around its outer circumference, and the racks 64, 66 include similar teeth 65, 67 extending substantially continuously along their lengths. In some embodiments, the deployment mechanism may include multiple pinions (not shown) coupled between the racks 64, 66, e.g., having different diameters or teeth configurations, e.g., to provide different rates of translation of the first and second racks 64, 66, if desired.

In the embodiment shown in FIG. 2B, the actuator 62 can be a slider button coupled directly to the first rack 64. The actuator 62 may be slidable within a slot (not shown) in the housing 23, thereby allowing the actuator 62 to be directed from a first or distal position, as shown, to a second or proximal position (not shown). Optionally, the slot or housing 23 may include pockets or other locking features (not shown) for releasably securing the actuator 62 (and consequently the deployment mechanism 60, tubular member 20, and/or support member 30) in one or more desired positions, e.g., the distal and proximal positions.

When the actuator 62 is activated, the deployment mechanism 60 can cause the first rack 64 to be directed proximally, thereby retracting the tubular member 20 proximally. Because of the cooperating teeth 65, 67, 69, movement of the first rack 64 can cause the pinion 68 to rotate, which, in turn, can cause the second rack 66 to advance distally and thereby advance the support member 30 distally. Thus, the actuator 62 and deployment mechanism 60 shown in FIG. 2B may substantially simultaneously cause the tubular member 20 to retract proximally and the support member 30 to advance distally to deploy the sealant 2, as described further below. In this arrangement, the relative motion of the tubular member 20 and support member 30 may be one-to-one, i.e., the tubular member 20 retracts the same distance that the support member 30 is advanced.

Figure 3:
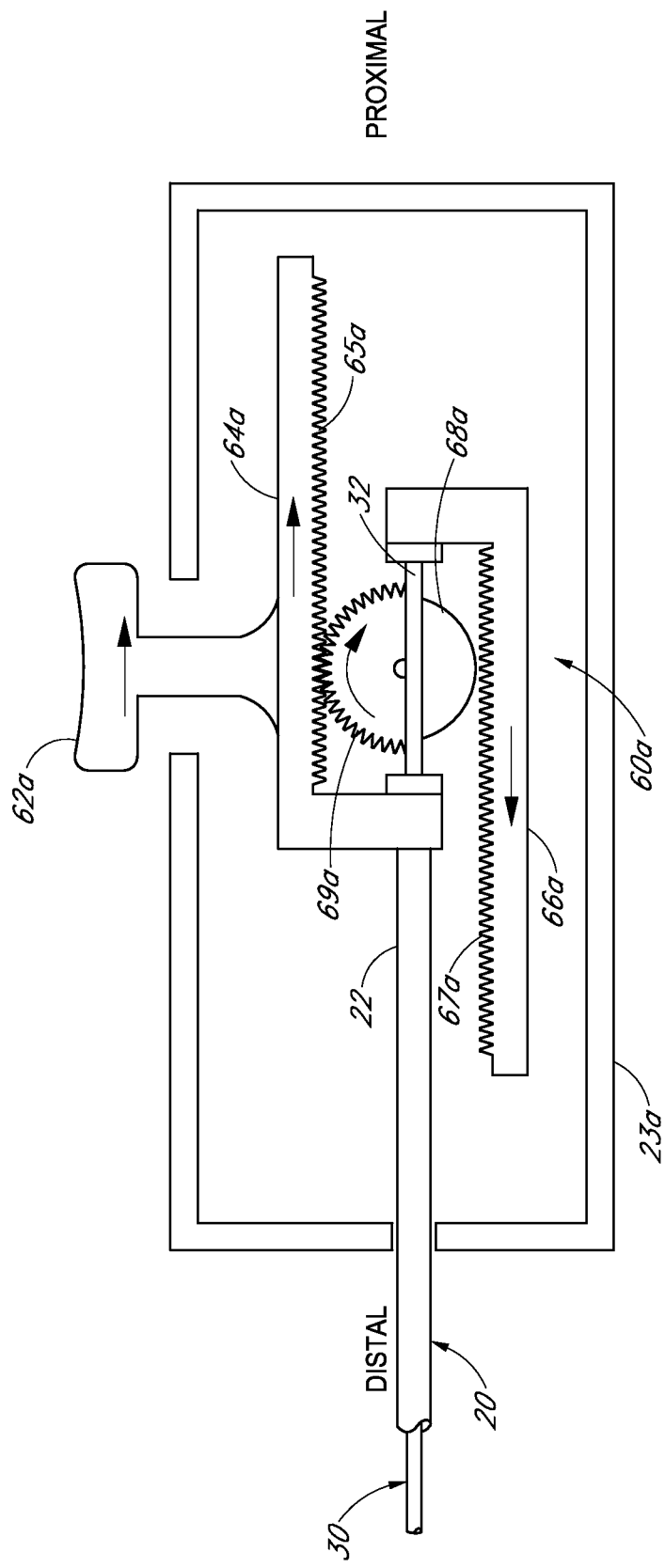
FIG. 3 is a cross-sectional view of an alternative embodiment of a deployment mechanism that may be provided within a housing of a cartridge, such as that shown in FIGS. 1A-2A, including a slider actuator and discontinuous teeth on a pinion of the deployment mechanism.

The teeth may be provided in discontinuous and/or non-uniform arrangements, if desired, e.g., to create predetermined delays in motion between the tubular member 20 and support member 30 and/or different rates of retraction and advancement. For example, FIG. 3 shows an alternative embodiment in which the racks 64a, 66a, and/or pinion 68a include teeth 65a, 67a, 69a that are not continuous. For example, the pinion 68a may be provided with teeth 69a that extend only partially around the outer surface or multiple sets of teeth 69a (only one set shown for simplicity) that are spaced apart from one another around the circumference of the pinion 68a.

In an exemplary embodiment, the racks 64a, 66a may include a substantially continuous set of teeth 65a, 67a, with the teeth 65a on the first rack 64a engaged with a corresponding first set of teeth 69a on the pinion 68a when the actuator 62a is provided in its initial distal position. In this position, the teeth 67a on the second rack 66a may not be engaged with any teeth on the pinion 68a. Thus, when the actuator 62a is initially activated, the first rack 64a may move immediately, thereby retracting the tubular member 20 immediately. As the actuator 62a and first rack 64a move, the pinion 68a may be rotated until a second set of teeth 69a (not shown) on the pinion 68a engage the teeth 67a on the second rack 66a. Further movement of the actuator 62a may consequently cause the second rack 66a to move, thereby advancing the support member 30 distally.

By providing one or more regions without teeth 69a on the pinion 68a, advancement of the support member 30 may be delayed for a desired time or distance after retraction of the tubular member 20 begins. For example, this delay may allow the sealant 2 to be partially or entirely exposed from the distal end 24 of the tubular member 20 before the support member 30 begins advancing to compress the sealant 2, which may reduce the risk of the sealant 2 being compressed and jamming within the tubular member 20.

If desired, the size and/or spacing of the teeth 65a, 67a on the racks 64a, 66a may be different than one another, e.g., to cause different translation distances as the actuator 62 is activated. For example, a second pinion (not shown) may be coupled between the pinion 68a and the second rack 66a that has a different diameter and/or teeth configuration corresponding to the teeth 67a on the second rack 66a, which may cause the support member 30 to advance a greater or lesser distance than the tubular member 20 is retracted as the actuator 62 is activated.

Figure 3A:
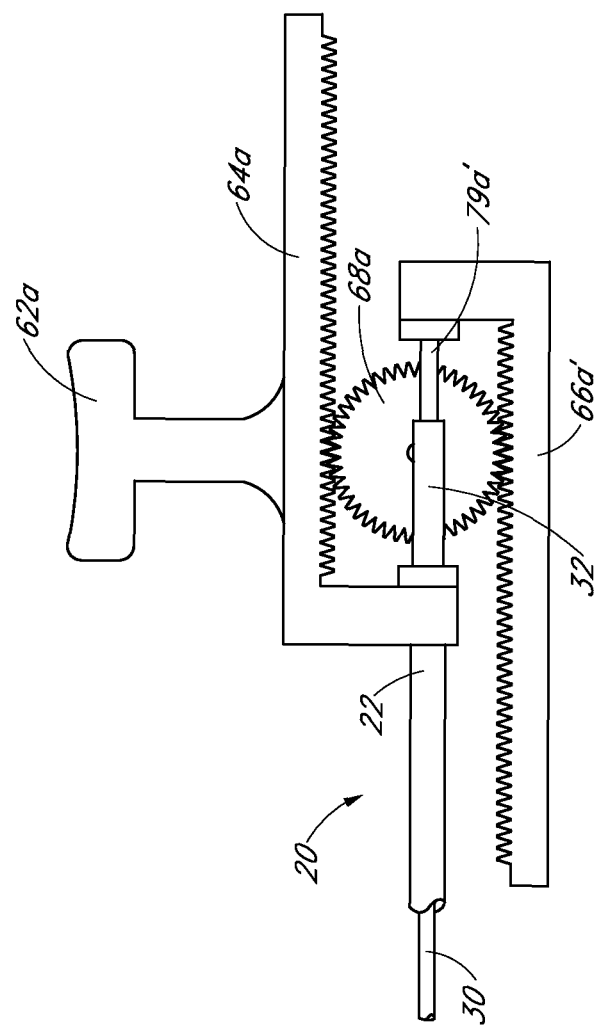
FIG. 3A is a cross-sectional view of another alternative embodiment of a deployment mechanism, including a support member that is indirectly coupled to the deployment mechanism.

In some embodiments, advancement of the support member 30 may be delayed by indirectly coupling the proximal end 32 of the support member 30 to the second rack 66. For example, as shown in FIG. 3A, the second rack 66a' may include a stem or other extension 79a' extending partially into the distal end 32 of the support member 30, e.g., to support the proximal end 32 from substantial lateral motion. The stem 79a' may be sized to slide into the support member 30 while still accommodating the positioning member (not shown) therethrough. Alternatively, another support (not shown) may be provided within the housing 23a' that supports the proximal end 32 of the support member 30 from moving laterally while allowing axial movement. Thus, in the initial position, the proximal end 32 of the support member 30 may be spaced distally away from the second rack 66a.'

The racks 64a, 66a,' and pinion 68a may include substantially continuous cooperating teeth (not shown), similar to the embodiment of FIG. 2B, such that, when the actuator 62a is activated, both racks 64a, 66a' may immediately move due to the pinion 68a. Because the proximal end 22 of the tubular member 20 is coupled directly to the first rack 64a, the first rack 64a may immediately begin retracting the tubular member 20. Although the second rack 66a' also begins advancing immediately, the support member 30 does not begin moving until the second rack 66a' contacts or otherwise engages the proximal end 32 of the support member 30. Thus, movement of the support member 30 may be delayed until the tubular member 20 has been retracted, e.g., by the offset distance of the proximal end 32 of the support member 30 from the second rack 66a.'

Although a slider button is shown in FIGS. 2B and 3 for the actuator 62, 62a, it will be appreciated that other actuators may be provided on the housing 23, 23a.' For example, turning to FIG. 4, another embodiment of a housing 23b is shown that includes a deployment mechanism 60b including first and second racks 64b, 66b coupled to one or more pinions (one pinion 68b shown) and to the proximal ends 22, 32 of a tubular member 20 and support member 30, generally similar to that of FIG. 3. Unlike the embodiment of FIG. 3, the actuator 62b includes a push button actuator that may be depressed at least partially into the housing 23b to activate the deployment mechanism 60b. As best seen in FIG. 4A, the actuator 62b includes a shaft 74b that is slidably mounted to the housing 23b, e.g., along a track, slot, or other guide (not shown).

The actuator 62b may be directed from a first or outer position, as shown, to a second or inner position (not shown) further into the housing 23b. The pinion 68b includes an axle 76b and the shaft 74b and axle 76b include cooperating teeth 75b, 77b that interact to cause rotation of the pinion 68b when the actuator 62b is activated. The relative size of the outer diameter of the teeth 77b on the axle 76b and the teeth 69b on the pinion 68b may be set to provide a desired advantage, e.g., such that a relatively small displacement of the actuator 62b may cause a greater displacement of the tubular member 20 and/or support member 30 (or vice versa).

For example, similar to the previous embodiments, the first rack 64b may be coupled to the pinion 68b such that the first rack 64b (and tubular member 20) is retracted immediately when the actuator 62b is initially activated. The second rack 66b may not be coupled to the pinion 68b until a predetermined delay, such that advancement of the support member 30 is delayed for a desired time or distance after retraction of the tubular member 20. Alternatively, if desired, other delays or arrangements may be provided using the deployment mechanism 60b, e.g., delaying retraction of the tubular member 20 for a predetermined time and/or causing advancement of the support member 30 before retraction of the tubular member 20 begins, e.g., by providing a discontinuous region of teeth 69b on the pinion 68b that do not engage the teeth 65b on the first rack 64b until the actuator 62b is partially depressed.

Figure 5:
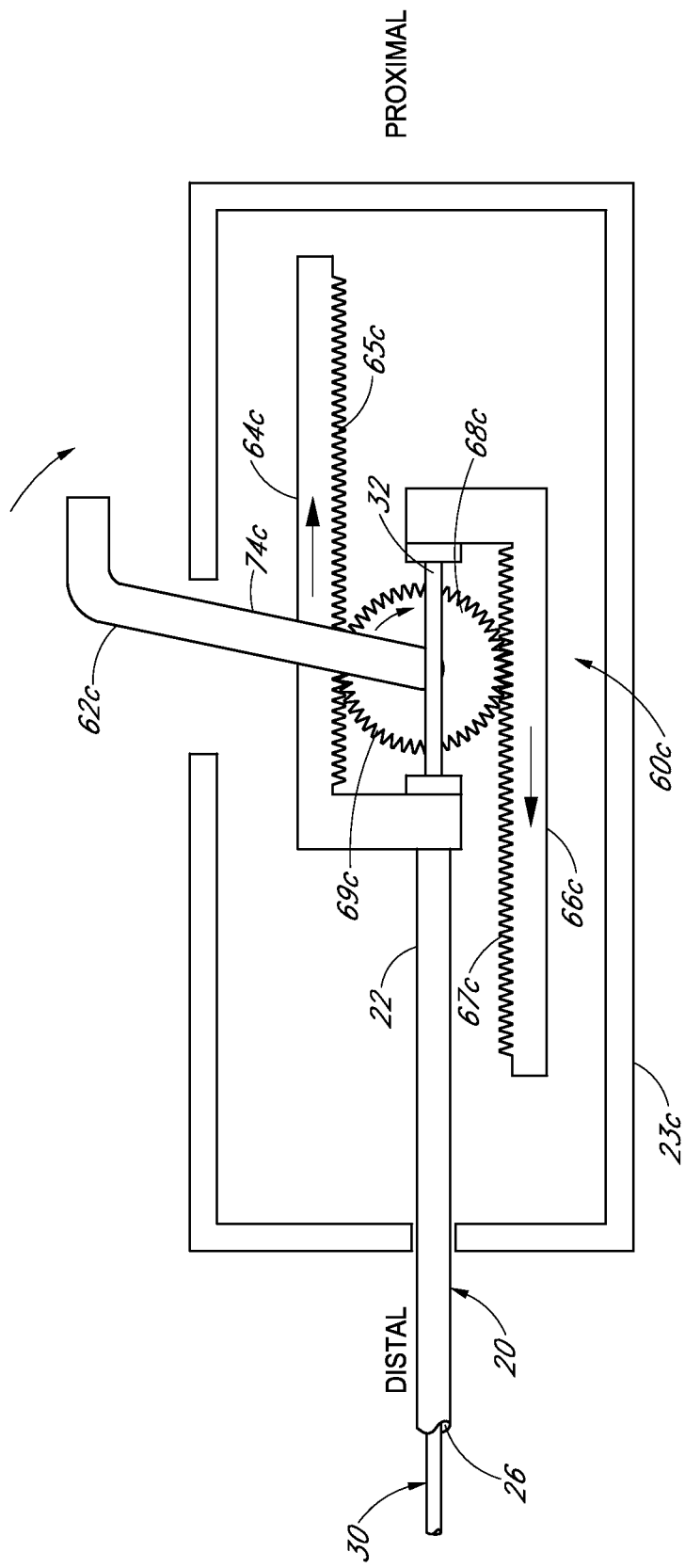
FIG. 5 is a cross-sectional view of yet another alternative embodiment of a deployment mechanism, including a lever actuator.

Turning to FIG. 5, another exemplary embodiment of a housing 23c is shown that includes a deployment mechanism 60c including first and second racks 64c, 66c coupled to a pinion 68c and to the proximal ends 22, 32 of a tubular member 20 and support member 30, generally similar to the previous embodiments. The actuator 62c can include a lever that may rotated or otherwise directed from a first or distal position to a second or proximal position (not shown). The actuator 62c can include a shaft 74c that is coupled to the pinion 68c such that rotation of the actuator 62c causes rotation of the pinion 68c. In certain aspects, one or more additional pinions may be coupled between the pinion 68c and the racks 64c, 66c, e.g., to provide a mechanical advantage and/or increased translation of the racks 64c, 66c based on the distance that the lever 62c is translated.

Similar to the previous embodiments, the first rack 64c may be coupled to the pinion 68c such that the first rack 64c (and tubular member 20) is retracted immediately when the actuator 62c is initially activated. The second rack 66c may not be coupled to the pinion 68c until a predetermined delay, such that advancement of the support member 30 is delayed after retraction of the tubular member 20. If desired, other delays or arrangements may be provided using the deployment mechanism 60c, similar to the other embodiments herein.

Optionally, any of these deployment mechanisms 60-60c may include features that limit the movement of the actuator 62-62c and/or racks 64-64c, 66-66c. For example, with reference to the embodiment of FIG. 2B (merely as an example), the first rack 64 and/or track 70 may include one or more ratchets or other unidirectional features (not shown) that allows the first rack 64 to move freely proximally from the distal position towards the proximal position, but prevent distal movement. Similar features may be coupled to the actuator 62 and/or to the pinion 68 that allow the actuator 62 and/or pinion 68 to move in only one direction, e.g., to allow retraction of the tubular member 20 but not allow the tubular member 20 to be subsequently advanced distally. Thus, once the tubular member 20 is being retracted to at least partially expose the sealant 2, the tubular member 20 may not be advanced distally back over the sealant 2, which may otherwise jam and/or damage the sealant 2. In addition or alternatively, one or more locking features (not shown) may be provided on the positioning member 14, e.g., to limit movement of the tubular member 20 and/or support member 30, as described further below.

Optionally, any of the embodiments herein may include other desired features on the housing 23. For example, as shown in FIG. 2B, a guide member 78 may be provided that is sized to slidably receive the positioning member 14 therethrough. The guide member 78 may be aligned with the second rack 66 and/or the proximal end 32 of the support tube 30 to accommodate sliding the cartridge 10 over the positioning member 14, as described elsewhere herein. In addition or alternatively, a spring mechanism 78a may be provided around the guide member 78 and/or otherwise coupled between the deployment mechanism 60 and the positioning member 14. For example, a compression spring 78a may be provided between a stop on the first rack 64 and a hub 48 on the positioning member 14 to facilitate and/or automatically retract the positioning member 14 during a procedure, as described elsewhere herein.

In addition or alternatively, the housing 23 may include a sheath catch assembly within a shroud 23a, similar to other embodiments herein. Optionally, the housing 23 may also include one or more detents or other features (not shown) for coupling the cartridge 16 to the positioning member 14, e.g., to releasably couple the housing 23 to the hub 48 shown in FIGS. 1A-2A, as described further below and in the references incorporated by reference herein. In addition or alternatively, the housing 23 may include a trigger lock (not shown), which may be coupled to the deployment mechanism 60, e.g., to prevent movement of the actuator 62 and/or deployment mechanism 60 until the lock is released, as described further below.

Returning to FIGS. 1A-2A, the positioning member 14 generally can include an elongate member 40 including a proximal end 42, a distal end 44, and an occlusion or positioning element 46 on the distal end 44. The positioning element 46 may be an expandable member, such as a balloon, a wire mesh structure, an expandable frame, and the like, e.g., sized to be advanced through an introducer sheath when collapsed, as disclosed in the references incorporated by reference herein. The positioning element 46 may be selectively expandable, e.g., using a source of inflation media, such as syringe, a pull wire, and/or other actuator (not shown), operable from the proximal end 42 of the positioning member 14.

For example, as shown, the positioning element may be a balloon 46, and the positioning member 14 may include a tubular body 40 including a lumen (not shown) extending between the proximal and distal ends 42, 44 and communicating with an interior of the balloon 46. In some embodiments, the positioning member 14 may include a source of inflation media, such as syringe 148, that may communicate with an interior of the hub 48 via an inflation line 48c or otherwise coupled to the hub 48 on the proximal end 42 of the positioning member 14. Optionally, the positioning member 14 may include an internal pull wire (not shown) that causes the balloon 46 to shorten during expansion and extend during collapse. Exemplary embodiments of positioning members 14 including balloons that may be used are disclosed in U.S. Publication Nos. 2004/0249342, 2004/0267308, 2006/0253072, and 2008/0009794. The entire disclosures of these references are expressly incorporated by reference herein.

In some embodiments, the positioning element may be biased to an enlarged condition, but may be compressed to a contracted condition, e.g., by an overlying sleeve or other constraint (not shown). The constraint may be removed to expose the positioning element, allowing the expandable element to automatically expand to the enlarged condition. Additional information on expandable structures that may be provided on the positioning member 14 may be found in U.S. Pat. Nos. 6,238,412, 6,635,068, and 6,890.343, and in co-pending application Ser. No. 10/975,205, filed Oct. 27, 2004. The entire disclosures of these references are expressly incorporated herein by reference.

In addition or alternatively, the positioning member 14 may include one or more additional features for limiting or facilitating movement of the positioning member 14, e.g., relative to the cartridge 16 and/or other components of the apparatus 10. For example, as shown in FIGS. 7A-7C, the positioning member 14 may include a retraction lock 114 within the housing 23 (not shown for simplicity), which may limit movement of the positioning member 14 relative to the first rack 64. The retraction lock 114 may be fixed axially relative to the tubular body 40 of the positioning member 14 and may have an outer dimension greater than an opening 61 in the first rack 64 (which may otherwise accommodate the positioning member 14 and/or support member 30 (not shown) moving axially relative to the first rack 64. For example, the retraction lock 114 may be an annular member attached to the outer surface of the tubular body 40, e.g., by one or more of an interference fit, bonding with adhesive, fusing, sonic welding, and the like.

The apparatus 10 may be provided with the retraction lock 114 located as shown in FIG. 7A, e.g., with the cartridge 16 in the position shown in FIGS. 1A-2A. In some embodiments, the relative lengths of the tubular body 40 of the positioning member 14 and the tubular member 20 of the cartridge 16 may be such that the sealant 2 (not shown, see, e.g., FIG. 2A) is disposed immediately adjacent the expandable member 46, i.e., such that advancement of the cartridge 16 is not necessary during the procedure, as described elsewhere herein and in the references incorporated by reference herein.

In some embodiments, the positioning member 14 cannot be retracted proximally relative to the cartridge 16 due to the retraction lock 114 abutting the first rack 64 within the housing 23. Thus, the retraction lock 114 may prevent undesired proximal movement of the positioning member 14, e.g., during preparation or other handling before the apparatus 10 is used to seal a puncture.

As shown in FIG. 7B, when the actuator 62 of the deployment mechanism 60 (not shown) is activated to retract the first rack 64 (and tubular member 20, also not shown), the retraction lock 114 can become spaced a corresponding distance 115A from the first rack 64. Thereafter, if the positioning member 14 is retracted, e.g., manually or automatically during a sealing procedure, as described elsewhere herein, the distance that the positioning member 14 may be retracted is limited by the distance 115B, i.e., until the retraction lock 114 again abuts the first rack 64, as shown in FIG. 7C.

In addition or alternatively, the positioning member 14 may include an auto-retraction assembly 140 that may be used to automatically retract the positioning member 14 during use. For example, FIGS. 6A and 6B show an exemplary embodiment of an auto-retraction assembly 140 attached or otherwise coupled to a positioning member 14,' which is generally similar to other positioning members described elsewhere herein and in the applications incorporated by reference herein. Alternatively, the features of the auto-retraction assembly 114 may be incorporated directly into the hub 48' of the positioning member 14' (not shown).

Generally, the auto-retraction assembly 140 includes a housing 142 including a chamber 143 within which a piston 144 may be slidably disposed. The chamber 143 may be substantially sealed between the piston 144 and the hub 48,' e.g., by the piston 144 itself and/or other seals 144a, such that fluid and/or pressure may be introduced into or evacuated from the chamber 143 without substantial leakage. The piston 144 may be coupled to the tubular body 40' of the positioning member 14,' e.g., adjacent the proximal end 42' of the tubular body 40,' e.g., by one or more of an interference fit, bonding with adhesive, fusing, sonic welding, and the like.

In addition, a fluid/pressure line 146 communicates with the chamber 143, e.g., coupled to the inflation line 48c' communicating with a syringe (not shown), similar to that shown in FIG. 1A, which may be the same syringe used to inflate and collapse the expandable member 46' of the positioning member 14.' The fluid/pressure line 146 may include a flow control switch 146a to selectively open and close the fluid/pressure line 146 during use, e.g., such that the chamber 144 communicates with the syringe only when the switch 146a is open.

Before use, the positioning member 14' may be provided with the piston 144 in the distal position shown in FIG. 6A. As shown, in this position, the proximal end 42 of tubular body 40 is generally extended and/or straight. To secure the piston 144 and proximal end 42 in this position, the switch 146a may be opened and fluid introduced into the chamber 143, whereupon the switch 146a may be closed.

When it is desired to retract the positioning member 14,' e.g., after deploying or exposing the sealant 2, the expandable member 46 may be collapsed, e.g., by evacuating fluid via the inflation line 48c' similar to other embodiments, with the switch 146a in the closed position. Once the expandable member 46 is collapsed, the switch 146a may be opened, and fluid evacuated from the chamber 143 via the fluid/pressure line 146, e.g., using the same syringe or a different syringe than that used to collapse the expandable member 46. This evacuation can cause the piston 144 to slide proximally within the housing 142 towards the hub 48,' as shown in FIG. 26B, thereby pulling the expandable member 46 proximally, e.g., through the sealant 2 and/or into the tubular member 20 (not shown), similar to the process shown in FIGS. 9A and 9B. As the piston 144 moves proximally within the housing 142, it can cause the proximal end 42 of the tubular body 40 to bunch and/or otherwise collapse within the chamber 143, also as shown in FIG. 6B.

In some embodiments, other auto-retraction features may be provided on the positioning member 14, e.g., similar to the spring mechanism 78a shown in FIG. 2B. For example, FIGS. 8A-8C shows another exemplary embodiment of an apparatus 210 that includes a positioning member 214 and cartridge 216 generally similar to other embodiments herein. As shown, the positioning member 214 can include a tubular body 240 including a hub 248 on its proximal end 242 and a balloon 246 on its distal end 244. The cartridge 216 can include a tubular member 220 including a sealant 2 and support member 230 therein, and a housing 223, which may include a deployment mechanism 260 therein, similar to any of the other embodiments herein. In some embodiments, the relative lengths of the tubular body 240 and tubular member 220 may be such that a distal end 224 of the tubular member 220, and consequently the sealant 2, may be located adjacent the balloon 246, thereby eliminating the need to advance the entire cartridge 216 during use.

The positioning member 214 can include a lock to selectively prevent the positioning member 214 from moving relative to the housing 223 and/or a biasing mechanism for automatically retracting the positioning member 214. For example, the lock may include a hydraulic lock, e.g., an expandable balloon or membrane 261, surrounding a distal portion of the hub 248 that is located within the housing 223. An interior of the membrane 261 may communicate with the inflation line 248c that communicates with the interior of the balloon 246 or alternatively, may communicate with a separate inflation line (not shown), if desired. In certain aspects, a bellows structure (not shown) may be provided on the hub 248 that expands and/or retracts when activated by fluid. In certain aspects, a mechanical lock (not shown) may be provided that may be manually activated to lock and/or release the hub 248 from the housing 223 or the membrane 261 may be configured for directing expandable detents or other features to engage between the hub 248 and housing 223, if desired.

Initially, as shown in FIG. 8A, the membrane 261 may be collapsed similar to the balloon 246. When the balloon 246 is expanded, fluid may also expand the membrane 261, as shown in FIG. 8B, thereby engaging the housing 223 and preventing subsequent axial movement of the positioning member 214 relative to the housing 223. When the balloon 246 is subsequently deflated, as shown in FIG. 8C, the fluid may also be evacuated from the interior of the membrane 261, thereby disengaging the positioning member 214 from the housing 223, and allowing the positioning member 214 to be subsequently retracted relative to the housing 223, e.g., to retract the collapsed balloon 246 through the sealant 2 and/or into the tubular member 220, similar to other embodiments herein. In certain aspects, a bellows lock may expand and/or retract and engage detents or other features between the hub 248 and housing 223. In certain aspects, a mechanical lock may be separately engaged, e.g., before or after expanding the balloon 246.

The housing 223 and hub 248 may include cooperating features that automatically retract the positioning member 214 when the balloon 246 is deflated or when the lock is otherwise disengaged. For example, as shown in FIGS. 8A-8C, a biasing mechanism may be provided that includes a spring 262 coupled between a first rack 264 (coupled to the tubular member 220) of the deployment mechanism 260 and the hub 248 of the positioning member 214. For example, a compression spring 262 may be positioned around the proximal end 242 of the tubular body 240 of the positioning member 214 within the housing 223 of the cartridge 216. As shown, a first end of the spring 262 may be coupled to or abut a proximal extension 264a of the first rack 264, and a second end of the spring 262 may be coupled to or abut a distal end of the hub 248. In the initial configuration shown in FIG. 8A, the spring 262 may be in a relaxed state, or in a slightly compressed state, e.g., if desired to bias the first rack 264 distally within the housing 223.

During use, an actuator (not shown) of the deployment mechanism 260 may be activated to direct the first rack 264 proximally, consequently retracting the distal end 224 of the tubular member 220 to expose the sealant 2, which may also advance the second rack 266 and the distal end 234 of the support member 230, similar to other embodiments herein, as shown in FIG. 8B. As the first rack 264 translates proximally within the housing 223, the first end of the spring 262 may be directed proximally towards the second end. However with the hydraulic lock 261 activated, the hub 248 of the positioning member 214 may be restrained from moving proximally, thereby compressing the spring 262 into a higher potential energy state, also as shown in FIG. 8B.

Subsequently, when it is desired to collapse and remove the balloon 246, fluid may be evacuated through the inflation line 248c, thereby causing both the balloon 246 and the membrane 261 to collapse. Due to the potential energy stored in the spring 262, the hub 248 of the positioning member 214 may automatically be directed proximally, thereby retracting the collapsed balloon 246 proximally, e.g., through the sealant 2 and into the distal end 224 of the tubular member 220, as shown in FIG. 8C. The support member 230 may remain substantially stationary during this action, thereby preventing the sealant 2 from moving proximally as the balloon 246 is retracted. Optionally, as shown in FIGS. 9A and 9B, the support tube 230 may include a stop or other feature 237 that may engage the second rack 266 to prevent retraction of the support member 230 when the positioning member 214 is retracted. In addition or alternatively, the second rack 266 and/or other components of the deployment mechanism (not shown) may include a brake or other features that prevent proximal movement of the second rack 266, e.g., to prevent inadvertent retraction of the support member 230.

Optionally, a delay may be provided in the biasing mechanism to delay collapse of the membrane 261 for a predetermined time relative to the balloon 246, e.g., to allow the balloon to collapse begin or complete collapsing before the membrane 261 is collapsed. Thus, the delay may ensure that the balloon 246 is substantially collapsed before the positioning member 214 is released and the spring 262 automatically retracts the balloon 246 through the sealant 2. For example, in some embodiments, a restriction (not shown) may be provided in the hydraulic circuit communicating from the inflation line 248c to the interior of the membrane 261. Thus, when fluid is initially evacuated via the inflation line 248c, fluid may be evacuated more quickly from the balloon 246 than the membrane 261.

In some embodiments, the inflation fluid delivered into the balloon 246 and membrane 261 may be selected to facilitate the desired timing or delay in collapse. For example, different sized orifices or other flow restrictors may be provided in the branches of the fluid path from the inflation line 248c to the interiors of the balloon 246 and membrane 261 and fluid with a desired viscosity may be provided to cause a delay in fluid flow between the branches. The flow restrictors internal diameters may be selected to allow for the balloon 246 to completely deflate before the membrane 261 is collapsed and the positioning member 214 is retracted through the sealant 2 and into the support tube 230.

In an exemplary embodiment, the viscosity of the fluid may be relatively higher than water, e.g., by including a mix of radiopaque contrast, which may also facilitate monitoring the balloon 246 under fluoroscopy or other external imaging. In certain embodiments, a mechanical lock may simply be disengaged at any time, e.g., after ensuring the balloon 246 is substantially collapsed, to retract the positioning member 214 and direct the collapsed balloon 246 through the sealant 2 into the support member 230, as shown in FIGS. 8C and 9B.

With additional reference to FIGS. 10A-10C, the apparatus 10 of FIGS. 1A-2B (or any of the other embodiments herein) may be used to position and deliver the sealant 2 within a puncture, e.g., extravascularly just above or otherwise adjacent to an arteriotomy in a blood vessel or other body lumen communicating with a puncture, as described further elsewhere herein. In the embodiment shown in FIGS. 1A-2A, the cartridge 16 (along with the sealant 2 within the tubular member 20) may be initially provided on the proximal end 42 of the positioning member 14. For example, the hub 48 on the positioning member 14 and the housing 23 on the cartridge 16 may be initially connected to one another, e.g., using one or more releasable detents (not shown). In some embodiments, as shown in the embodiment of FIGS. 8A-8C (or the apparatus 710 of FIGS. 16A-16D), the cartridge 216 may be initially provided such that the distal 224 of the tubular member 220 is disposed adjacent the balloon 246, e.g., as disclosed in U.S. Pat. No. 7,335,220 and U.S. Publication No. 2008/0082122, incorporated by reference elsewhere herein.

As shown in FIGS. 10B and 10C, the cartridge 16 may be slidable distally along the positioning member 14, e.g., by disconnecting the housing 23 from the hub 48, and then advancing the cartridge 16, e.g., until the distal end 24 of the tubular member 20 is disposed adjacent the positioning element 46. For example, detents on the housing 23 and hub 48 may simply separate from one another when the housing 23 is advanced away from the hub 48 with sufficient force. In some embodiments, one of the housing 23 and hub 48 may include an actuator or lock that may be activated (not shown) to separate the detents and/or otherwise allow the cartridge 16 to be advanced relative to the positioning member 14.

Optionally, the cartridge 16 and/or positioning member 14 may include cooperating features that limit distal movement of the cartridge 16 relative to the positioning member 14. For example, the housing 23 of the cartridge 16 may include a pocket and the positioning member 14 may include a detent or other feature (both not shown) that may be received within the pocket when the cartridge 16 is advanced to a distal position.

In addition or alternatively, one or more markers may be provided on the apparatus 10, e.g., to identify when components are located at one or more desired positions or otherwise to facilitate use of the apparatus 10. For example, the positioning member 14 may include one or more markers 43 at predetermined locations on the elongate member 40. Such markers may provide visual confirmation when the cartridge 16 has been advanced to a desired distal position, e.g., when the marker(s) 43 emerge from the housing 23 as the cartridge 16 is advanced over the positioning member 14.

Turning to FIGS. 10A-10G, an exemplary method is shown for sealing a puncture 90, e.g., using the apparatus 10 of FIGS. 1A-2B (or again any of the other embodiments herein) to deliver a sealant 2, e.g., to achieve hemostasis within the puncture 90. Generally, the puncture 90 extends from a patient's skin 92 through intervening tissue, e.g., to a body lumen 94. In an exemplary embodiment, the puncture 90 may be a percutaneous puncture communicating with a blood vessel 94, such as a femoral artery, carotid artery, and the like.

In an exemplary method, the puncture 90 may be created using known procedures, e.g., using a needle, guidewire, one or more dilators, and the like (not shown). An introducer sheath 80 may be advanced through the puncture 90 into the vessel 94, e.g., over a guidewire (not shown) placed through the puncture 90 into the vessel 94. The introducer sheath 80 may provide access into the vessel 92 for one or more instruments (not shown), e.g., to allow one or more diagnostic and/or interventional procedures to be performed via the vessel 94. Upon completing the procedure(s) via the vessel 94, any such instrument(s) may be removed from the puncture 90, leaving the introducer sheath 80 extending through the puncture 90 into the vessel 94.

With reference to FIG. 10A, the positioning member 14 may be introduced into and/or through the lumen of the introducer sheath 80, e.g., with the expandable positioning element 46 in a collapsed condition. The cartridge 16, along with the sealant 2, may be provided initially on the proximal end 42 of the positioning member 40 with the actuator 62 in the first or distal position, e.g., as shown in FIG. 2A. Thus, the distal end 24 of the tubular member 20 may initially be located outside the puncture 90 when the positioning member 14 is advanced into the puncture 90.

Still referring to FIG. 10A, the distal end 44 of the positioning member 14 may be inserted through the puncture 90 (via the introducer sheath 80) and into the vessel 94. If the cartridge is configured such that the sealant 2 is disposed immediately adjacent the positioning element, similar to the cartridge 216 of FIGS. 8A-8C, the distal end 224 of the tubular member 220 may also pass through the introducer sheath 80 and enter the vessel 94. Otherwise, as shown in FIGS. 10A and 10B, the distal end 24 of the tubular member 20 may remain outside the puncture 90.

Once the positioning element 46 is disposed within the vessel 94, i.e., beyond a distal end 84 of the introducer sheath 80, the positioning element 46 may be expanded to an enlarged condition, as shown. After expanding the positioning element 46, the positioning member 40 may be at least partially withdrawn until the positioning element 46 contacts the wall 96 of the vessel 94, e.g., to substantially seal the vessel 94 from the puncture 90. In an exemplary method, shown in FIGS. 10A and 10B, this may involve a two-step process (although it may be completed in a single substantially continuous action). First, with the positioning element 46 expanded within the vessel 94, the positioning member 14 may be withdrawn until the positioning element 46 contacts the distal end 84 of the introducer sheath 80, which may provide a first tactile feedback to the user (i.e., that the positioning element 46 has contacted the introducer sheath 80, e.g., based upon the increased resistance to proximal movement). The positioning member 14 may be withdrawn further until the positioning element 46 contacts the vessel wall 96 and resists further withdrawal, thereby providing a second tactile feedback. The introducer sheath 80 may be pulled proximally by the positioning element 46 as the positioning member 14 is withdrawn, e.g., until the distal end 84 of the introducer sheath 80 is withdrawn from the vessel 94 into the puncture 90, as shown in FIG. 10B.

Proximal tension may be applied and/or maintained on the positioning member 14 to hold the positioning element 46 against the vessel wall 96, e.g., to seal the puncture 90 from the vessel 94 and/or prevent further removal of the positioning member 14. The proximal tension may be maintained manually or using a tensioner device (not shown) to provide temporary hemostasis, e.g., during the subsequent steps. Exemplary tension devices are disclosed in U.S. Publication No. 2004/0267308, incorporated by reference elsewhere herein.

Turning to FIG. 10C, the cartridge 16 (carrying the sealant 2) may then be advanced distally over the positioning member 14 into the puncture 90. As shown, the distal end 24 of the tubular member 20 may enter the introducer sheath 80 and be advanced towards the positioning element 46. The cartridge 16 may be advanced until a component of the cartridge 16 encounters a stop on the positioning member 14, thereby preventing further advancement of the cartridge 16 and/or spacing the sealant 2 a predetermined distance from the positioning element 46. Alternatively, the cartridge 16 may be advanced into the introducer sheath 80 until the distal end 24 contacts the expanded positioning element 46, which may provide tactile feedback that the cartridge 16 has been advanced sufficiently, or the sealant 2 is otherwise positioned within the puncture 90.

Optionally, a sleeve or locking device (not shown) may be provided on the cartridge 16 that may couple the introducer sheath 80 to the tubular member 20 when the cartridge 16 is advanced, similar to other embodiments herein or embodiments disclosed in U.S. Publication No. 2009/0088793, the entire disclosure of which is expressly incorporated by reference herein. In some embodiments, the housing 23 of the cartridge 16 may include one or more features (not shown) that may engage mating features (also not shown) on the sheath hub 83, e.g., to couple movement of the tubular member 20 and/or other components of the cartridge 16 to the introducer sheath 80, similar to other embodiments herein.

Figure 11:
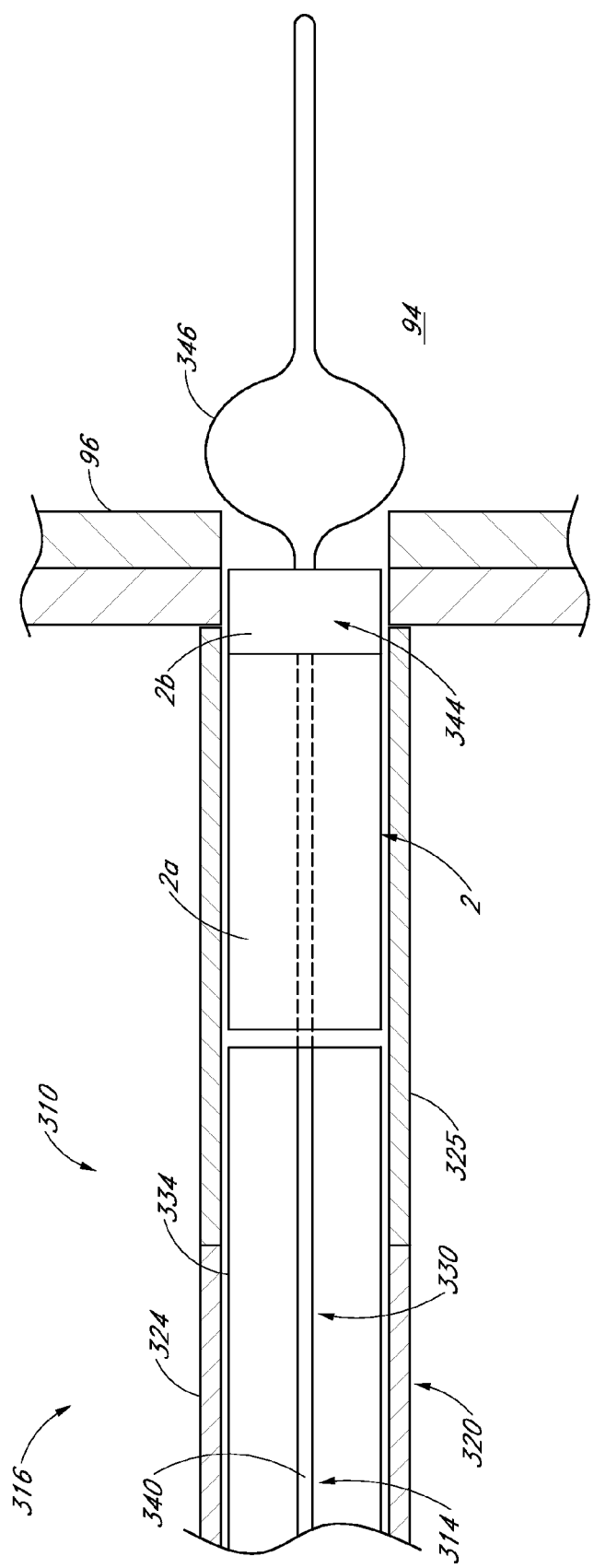
FIG. 11 is a cross-section view of a patient's body showing another embodiment of a cartridge for delivering a sealant into a puncture that includes a collapsible distal region.

In certain scenarios, if a cartridge, such as the cartridge 216 of FIGS. 8A-8C, is provided that includes the distal end 224 of the tubular member 220 and sealant 2 immediately adjacent the positioning element 246, the cartridge 216 is not advanced and is simply introduced into the sheath 80 along with the positioning member 214. Thus, the distal end 224 of the tubular member 220 may be exposed briefly within the vessel 94 before the positioning element 246 is expanded and the entire apparatus 210 withdrawn to direct the positioning element 246 against the vessel wall 96. In certain aspects, the sealant 2 may be recessed slightly within the distal end 224, e.g., if desired to minimize exposure of the sealant 2 to fluid, may be flush, or may extend slightly from the distal end 24, e.g., as shown in FIG. 11 and described further elsewhere herein.

Optionally, for the embodiment of FIGS. 8A-8C, the positioning member 214 and cartridge 216 may be advanced into the introducer sheath 80 until a marker (not shown) on the proximal end 222 of the tubular member 220 is aligned with the hub 83 of the introducer sheath 80, which may provide a visual indication that the positioning element 246 is disposed distally beyond the distal end 84 of the sheath 80, i.e., within the vessel 94. After the positioning element 246 has been expanded and the positioning member 214 and cartridge 216 retracted to position the positioning element 246 against the vessel wall 94, the sheath 80 may be retracted a desired distance to expose the distal end 224 of the tubular member 220 within the puncture 90 adjacent the positioning element 246, if desired. Optionally, the tubular member 20 may include another marker (not shown), which may be aligned with the hub 83 of the introducer sheath 80 when the sheath 80 has been sufficiently retracted.

If desired, the cartridge 216 may include a trigger lock (not shown), e.g., on the distal end of the housing 223, and the sheath 80 may be retracted until the hub 83 engages the trigger lock. Without the sheath 80 engaged to the trigger lock, the trigger lock may prevent the actuator 262 of the deployment mechanism 260 from being activated, thereby preventing unintentional deployment of the sealant 2.

In some embodiments, the sheath 80 may be coupled to the cartridge 216 when the apparatus 210 has been advanced sufficiently into the sheath 80, e.g., such that movement of the sheath 80 is coupled to movement of the tubular member 220. It may be desirable for the introducer sheath 80 to have a predetermined length relative to the tubular member 220 such that the distal ends 84, 224 of the sheath 80 and tubular member 220 are aligned with one another, e.g., substantially coextensive with one another. Thus, when the tubular member 220 (and consequently the sheath 80) are retracted, the sealant 2 may be exposed beyond the distal end 84 of the sheath 80.

Figure 10D:
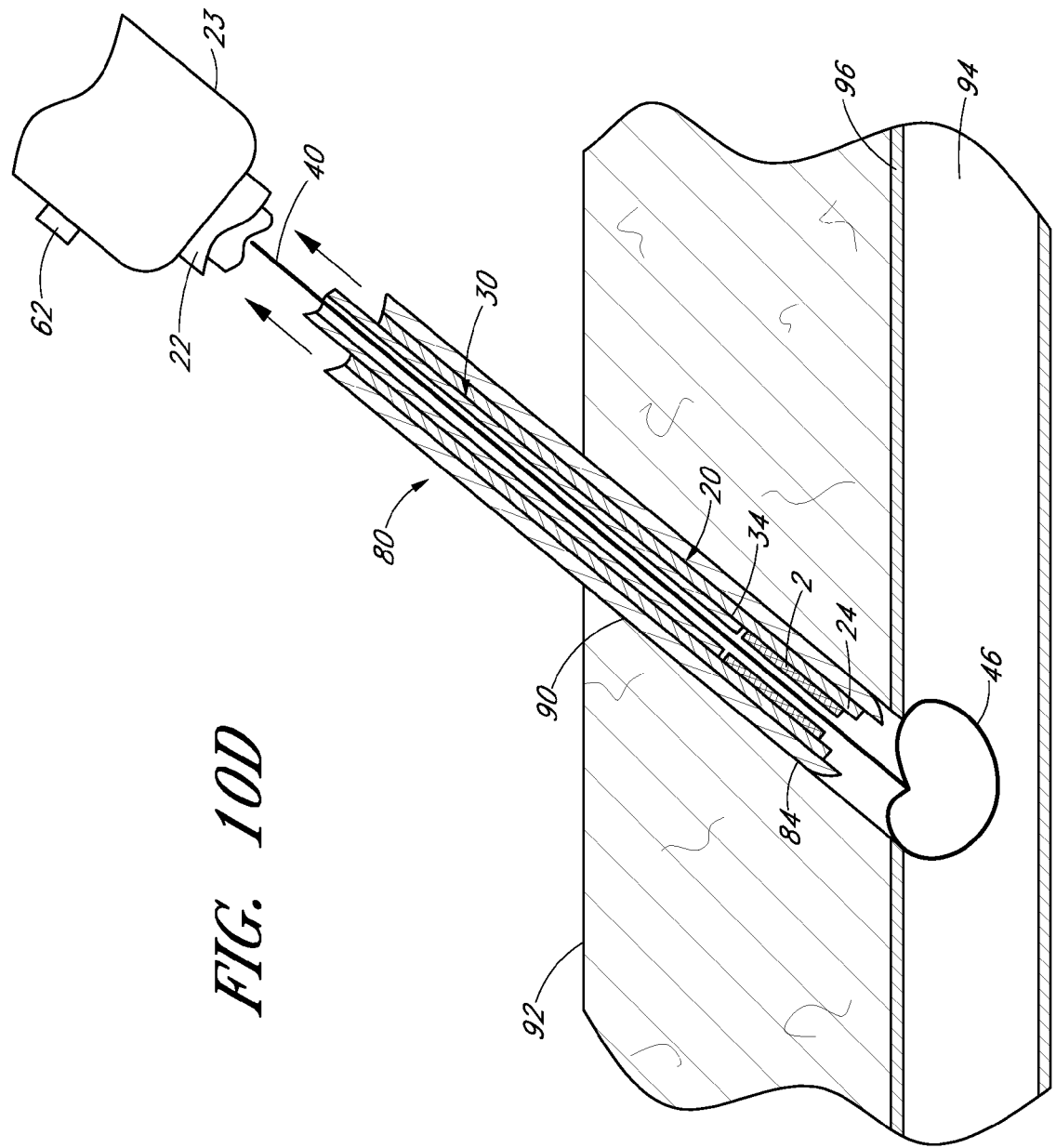
Figure 10E:
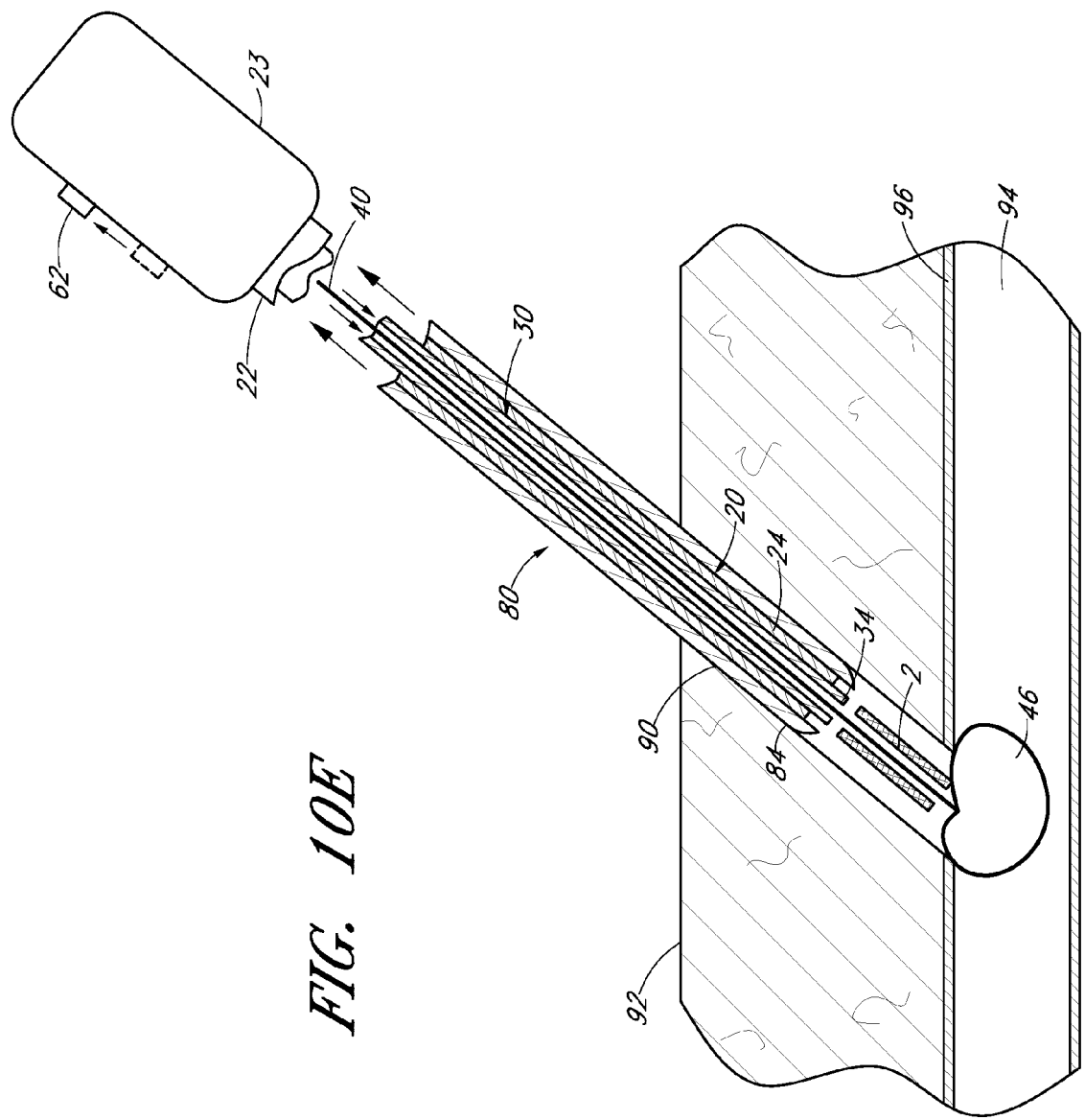
Figure 10F:
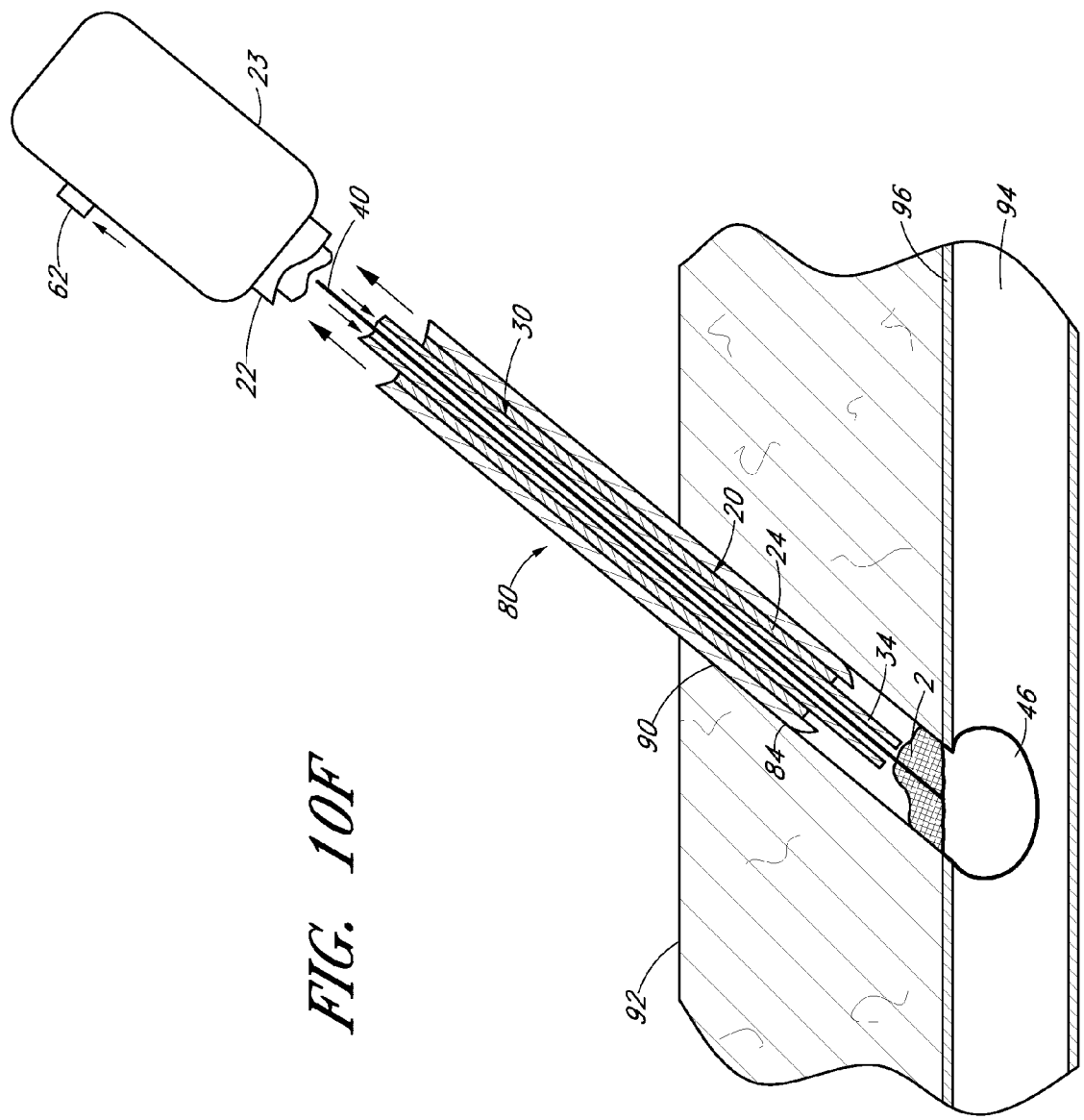

Thereafter, turning to FIG. 10D with continued reference to the apparatus 10 of FIGS. 1A-2B, the actuator 62 may be activated, e.g. by directing the actuator 62 to the second or proximal position, thereby causing the tubular member 20 (and introducer sheath 80, if coupled to the tubular member 20 or not already withdrawn) to begin retracting relative to the positioning member 14, sealant 2, and support member 30. For example, the delay provided in the deployment mechanism 60 (not shown, see, e.g., FIG. 2B) may allow the tubular member 20 to be retracted, with the support member 30 preventing substantial proximal movement of the sealant 2, until the sealant 2 is substantially exposed within the puncture 90 beyond the introducer sheath distal end 84, as shown in FIGS. 10D and 10E. As the actuator 62 continues to be directed towards the second position, the support member 30 may begin to advance, as shown in FIGS. 10E and 10F, thereby compressing the sealant 2 against the expanded positioning element 46 and/or the arteriotomy and vessel wall 96.

When the sealant 2 is exposed within the puncture 90, the sealant 2 may be exposed to blood and/or other body fluids within the puncture 90. This exposure may cause the sealant 2 to absorb fluid and activate to provide hemostasis, as described further elsewhere herein. If the sealant 2 includes distal section formed from non-crosslinked precursors, the precursors may crosslink and bond the sealant 2 relative to surrounding tissues, e.g., bonding to the outer surface of the vessel wall 96 and/or other tissue adjacent the arteriotomy, or may fill or otherwise penetrate into the arteriotomy, e.g., optionally extending into the interior of the vessel 94, which may enhance the resulting seal and/or prevent migration of the proximal section 4 of the sealant 2, e.g., away from the arteriotomy and vessel wall 96.

Figure 10G:
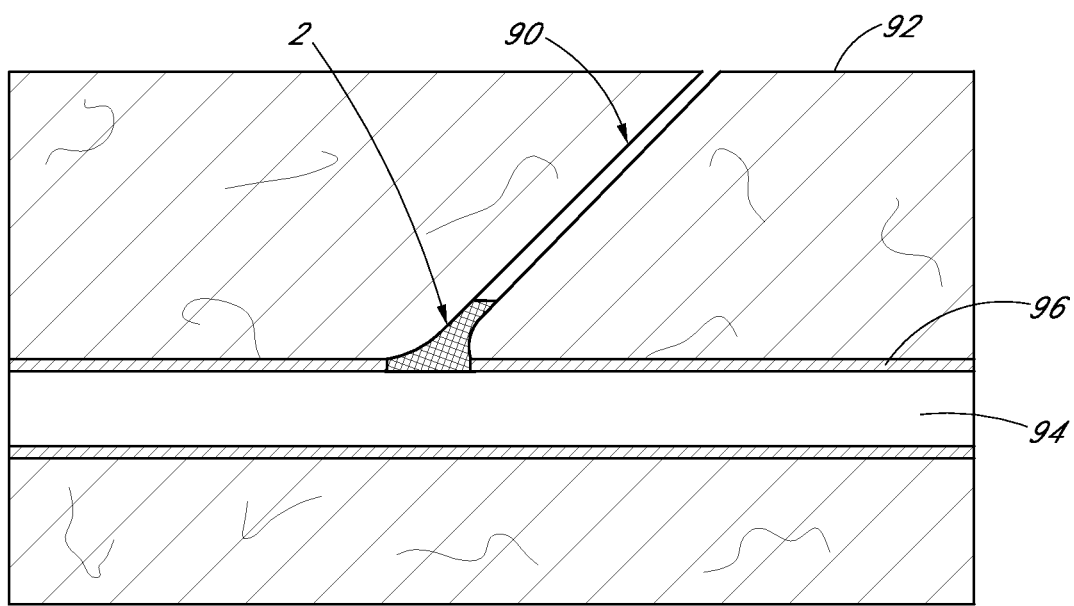

After sufficient time, the positioning element 46 may be collapsed, and the apparatus 10 may be withdrawn from the puncture 90, leaving the sealant 2 within the puncture 90 and/or against the vessel wall 96, as shown in FIG. 10G. Initially, the positioning member 14 may be retracted through the sealant 2, e.g., into the support member 30, e.g., as shown in FIGS. 9A and 9B. Optionally, the positioning member 14 may be automatically retracted, e.g., using an auto-retraction assembly (not shown), such as those described elsewhere herein.

In some embodiments, an actuator, e.g., a single button, or a pair of opposing buttons (not shown), may be provided on the positioning member 14. The button(s) may be located on the hub 48, which may be secured to the table on which the patient is placed or other fixed surface during the procedure. The squeeze design may retract the deflated balloon 46 through the compressed sealant 2 as the positioning member 14 is removed from the vessel 94 and puncture 90.

With continued reference to FIGS. 9A and 9B, the support member 30 may remain substantially stationary when the positioning member 214 is retracted, as described elsewhere herein, thereby preventing the sealant 2 from being directed proximally away from the vessel wall 96 when the positioning element 46 is pulled through the sealant 2. If desired, the support member 30 may be advanced further, e.g., to compress the sealant 2 within the puncture 90. The support member 30 and any other components of the apparatus 10 still extending into the puncture 90 may then be removed, leaving the sealant 2 within the puncture and/or against the vessel wall 94.

Turning to FIG. 11, another exemplary embodiment of an apparatus 310 is shown for sealing a puncture through tissue.

Generally similar to the previous embodiments, the apparatus 310 can include a positioning member 314 and a cartridge 316 carried on the positioning member 314 for delivering a sealant 2 therein into a puncture (not shown). The positioning member 314 can include a tubular body 340 including a hub on its proximal end (not shown) and a balloon 346 on its distal end 344. The cartridge 316 can include a tubular member 320 including a sealant 2 and support member 330 therein. Similar to the embodiment of FIGS. 8A-8C, the relative lengths of the tubular body 340 and tubular member 320 may be such that a distal end 324 of the tubular member 320, and consequently the sealant 2, may be located immediately adjacent the balloon 346. Thus, there is no need to advance the entire cartridge 316 during use.

The tubular member 320 can include a composite distal end 324 including a distal tip segment 325 formed differently than the adjacent distal end portion. For example, the distal segment 325 may include a plurality of slits or other weakened regions (not shown), e.g., extending axially, helically, or otherwise along at least a portion of the distal segment 325. In addition or alternatively, the distal segment 325 may be have a relatively thinner wall thickness than the adjacent distal end 324 and/or may be formed from weaker material that may be easily split, folded, collapsed, expanded, or otherwise crushed to expose the sealant 2 therein.

As shown, the sealant 2 can include a proximal or main section 2a and a distal or tip section 2b that is formed from non-crosslinked precursors. The distal section 2b may extend at least partially from the distal segment 325 of the tubular member 320, e.g., as shown in FIG. 11. For example, the apparatus 310 may be furnished to the user with the distal section 2b exposed, or the user may advance the support member 330 a predetermined distance, e.g., using an actuator on a handle (both not shown) of the cartridge 316. If the distal section 2b extends at least partially from the distal segment 325, the distal section 2b may optionally have a rounded or other shape, e.g., to provide a substantially atraumatic and/or tapered shape (not shown) to facilitate introduction into an introducer sheath and/or puncture.

The apparatus 310 may be introduced into a puncture, e.g. through a previously placed introducer sheath (not shown) with the positioning element 346 collapsed such that the positioning element 346 and distal segment 325 may be exposed beyond the introducer sheath within the puncture and/or vessel 94. The positioning element 346 may be expanded and directed against the vessel wall 96, as shown in FIG. 11, and the introducer sheath may be withdrawn, if necessary to expose the distal segment 325, similar to other embodiments herein.

With the distal section 2b of the sealant 2 at least partially exposed, crosslinking may be initiated, thereby bonding the sealant 2 to the arteriotomy, vessel wall 94, and/or surrounding tissue, similar to other embodiments herein. The support member 330 may then be advanced to press the sealant 2 against the vessel wall 96 and/or positioning element 346, thereby applying an outward expansive force on the distal segment 325 of the tubular member 320 as the sealant 2 is compressed. This can cause the distal segment 325 to split, fold, collapse, or otherwise crush to expose the sealant 2 within the puncture. The positioning element 346 may be collapsed (e.g., using any of the apparatus and methods herein), and the apparatus 310 removed from the puncture, similar to other embodiments herein. The bonding of the distal section 2b to the vessel wall 96 may prevent jamming of the sealant 2 and/or disengagement of the sealant 2 when the apparatus 310 is removed.

Thus, the distal segment 325 may provide a skirt or cover over the sealant 2 to minimize premature exposure of the sealant 2 to fluid, yet may open to expose the sealant 2 without having to retract the tubular member 320 relative to the support member 330, positioning element 346, and/or vessel wall 96.

Figure 12:
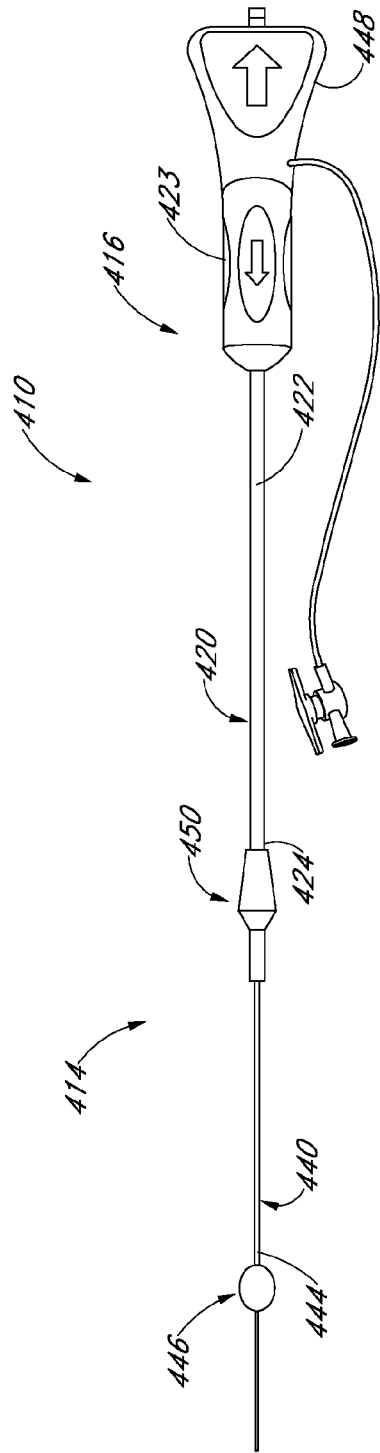
FIG. 12 is a side view of another embodiment of an apparatus for sealing a puncture through tissue that including a positioning member, and a cartridge movable over the positioning member that includes a slidable sealant sleeve over a sealant and support member.

Turning to FIG. 12, another exemplary embodiment of an apparatus 410 is shown for sealing a puncture through tissue. Generally similar to the previous embodiments, the apparatus 410 can include a positioning member 414 and a cartridge 416 carried on the positioning member 414 for delivering a sealant 2 therein into a puncture (not shown). The cartridge 416 may not include a tubular member carrying sealant and a support member therein. Instead, the cartridge 416 can include a sealant sleeve 450 carrying sealant 2 therein, and surrounding a distal end 434 of a support member 430 adjacent the sealant 2, and a handle or hub 423 on the proximal end 432 of the support member 430. As shown, the cartridge 416 may be provided initially adjacent a hub 448 of the positioning member 414, although, alternatively, the cartridge 416 may be initially provided such that the sealant sleeve 450 and sealant 2 are located immediately adjacent a positioning element 446 of the positioning member 414, e.g., similar to the apparatus 710 shown in FIGS. 16A-16D and described further elsewhere herein.

Figure 12A:
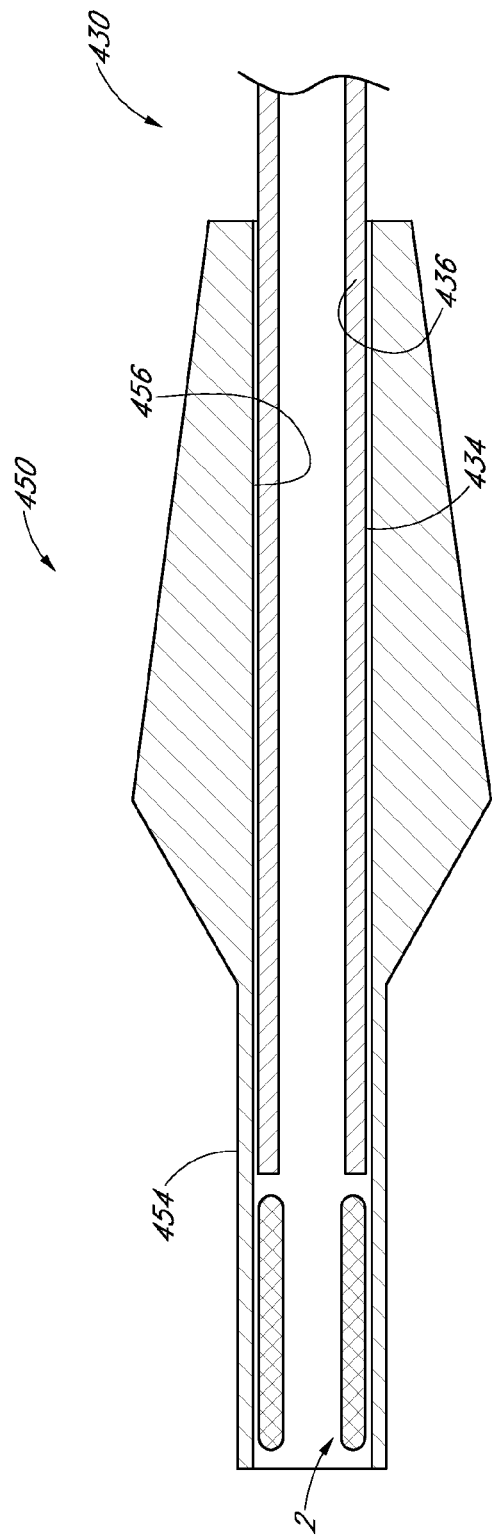
FIG. 12A is a cross-section detail of the distal end of the cartridge of FIG. 12.

As best seen in FIG. 12A, the sleeve 450 may include a relatively large diameter proximal portion 452, e.g., sized to abut or otherwise contact a hub or proximal end 83 of an introducer sheath 80 (not shown, see, e.g., FIGS. 13A-13C), and a relatively small diameter distal portion 454, e.g., sized to enter the hub 83 and/or lumen of the introducer sheath 80. For example, the introducer sheath hub 83 may include one or more valves, e.g., a hemostatic valve therein, and the sleeve distal portion 454 may be sized to enter the hub 83 and at least partially open the valve when the cartridge 416 is advanced, e.g., to facilitate the sealant 2 and/or support member 430 entering the introducer sheath lumen, as described further below.

The sleeve 450 may have a relatively short length compared to the support member 430, e.g., such that the sleeve 450 may slide proximally over the support member 430 a desired distance. For example, the sleeve 450 may have an overall length between about five and forty millimeters (5-40 mm), between about ten and twenty four millimeters (10-24 mm), and the like, and the distal portion 454 may have a length, e.g., between about three and twenty millimeters (3-20 mm), between about twelve and twenty four millimeters (12-24), between about fifteen and eighteen millimeters (15-18 mm), and the like, e.g., sufficient to substantially cover the sealant 2.

Optionally, the sleeve 450 may include an inner lumen 456 configured to provide preferential and/or different frictional interference with an outer surface of the support member 430. For example, the inner lumen 456 may allow the sleeve 450 to slide freely proximally relative to the support member 430, while providing enhanced friction that resists distal movement of the sleeve 450 over the support member 430. In addition or alternatively, the sleeve 450 may be releasably attached to the distal end 434 of the support member 430, e.g., using a low bond adhesive, and the like, which may be released or otherwise overcome when the cartridge 416 is advanced into an introducer sheath, as described further below.

In an exemplary embodiment, the sleeve 450 may be formed from an outer annular body and a section of tubing at least partially received within the annular body (not shown). In certain aspects, the sleeve 450 may be integrally formed as a single piece, e.g., by molding, machining, casting, and the like. The components of the sleeve 450 may be made from the same or different materials, e.g., plastic, metal, or composite materials. Exemplary materials and methods for making the sleeve 450 are disclosed in U.S. Pat. No. 7,993,367, the entire disclosure of which is expressly incorporated by reference herein.

Figure 13A:
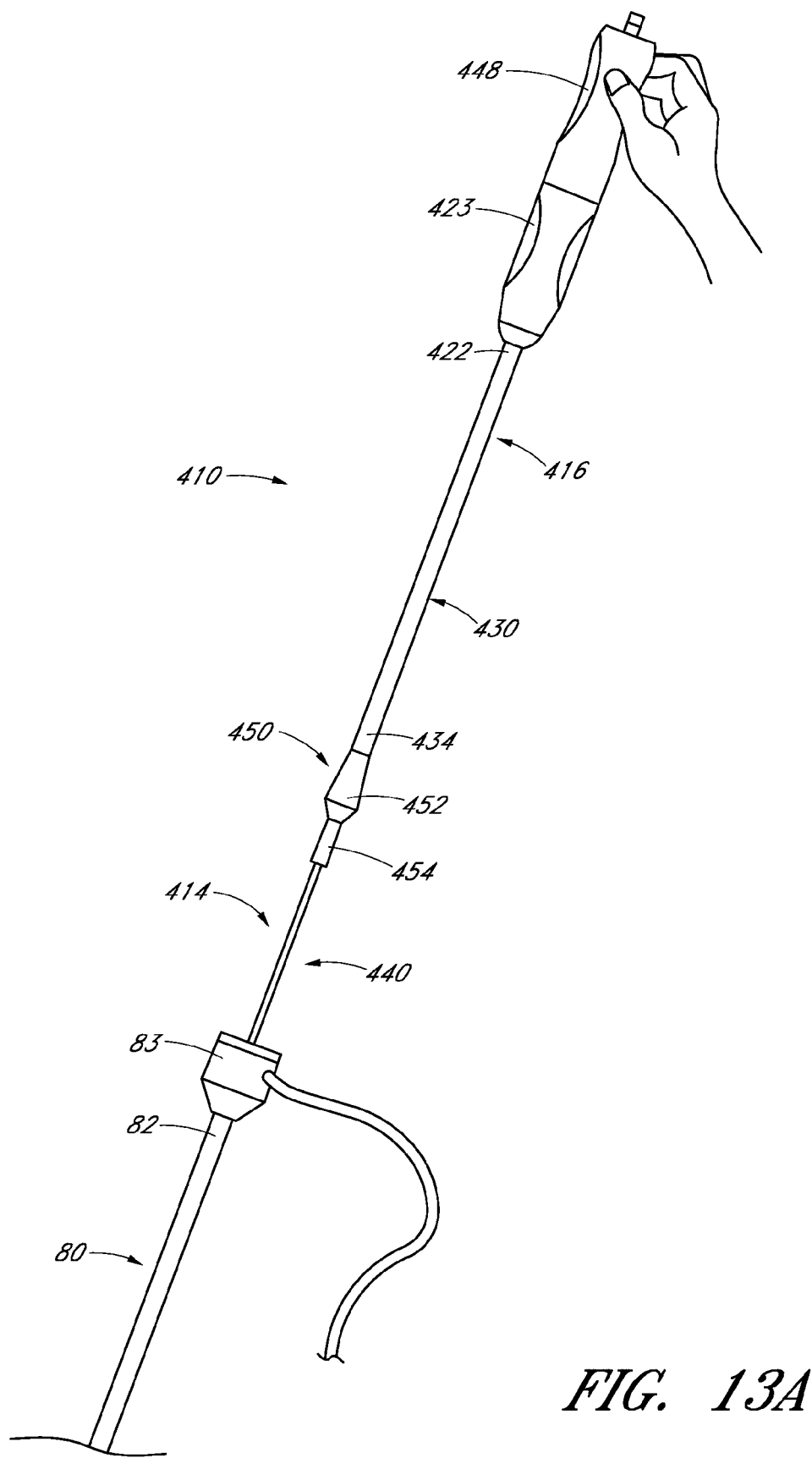
FIGS. 13A-13C are cross-sectional views of a patient's body showing a method for sealing a puncture using the apparatus of FIG. 12.
Figure 13B:
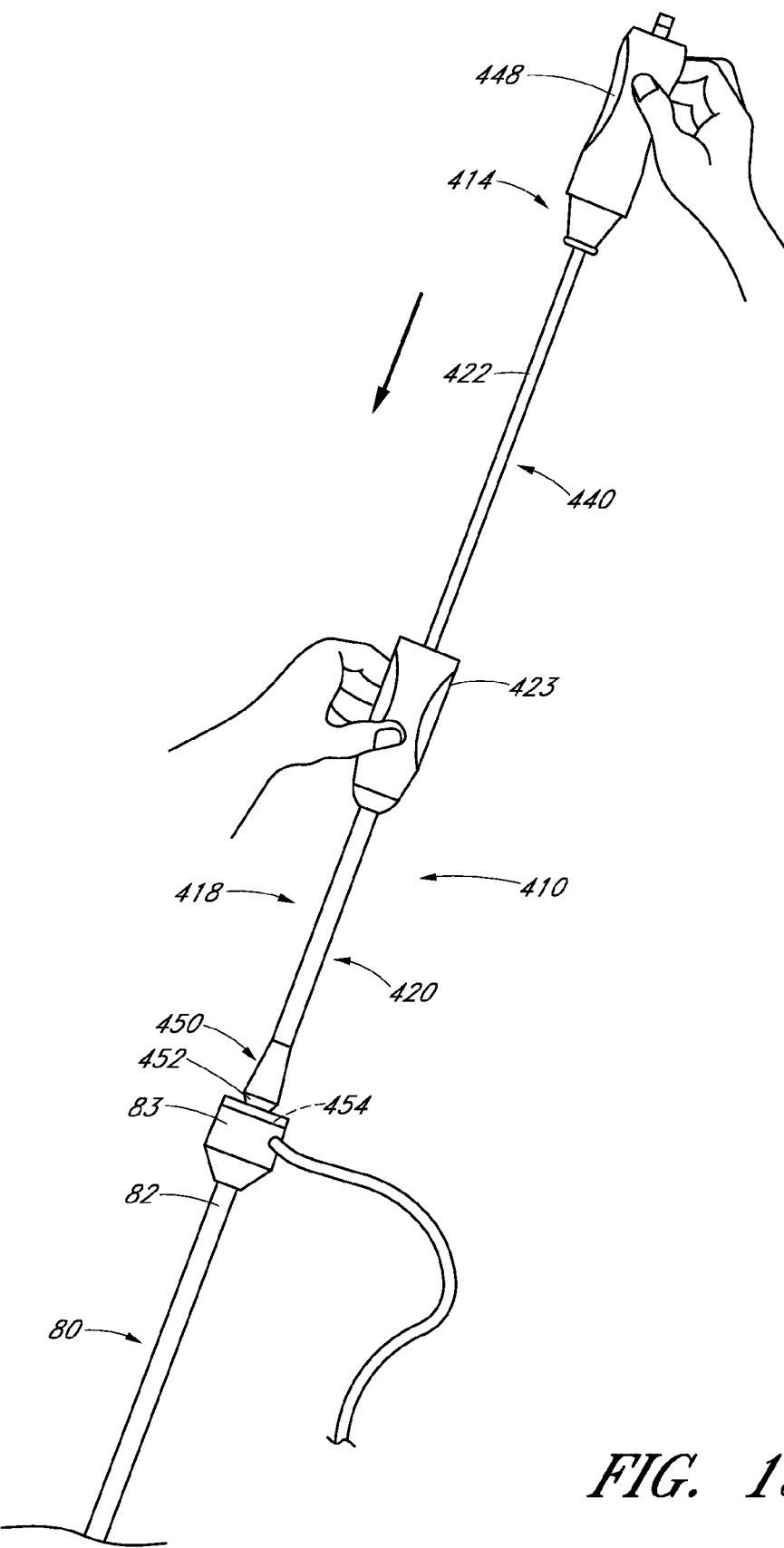
Figure 13C:
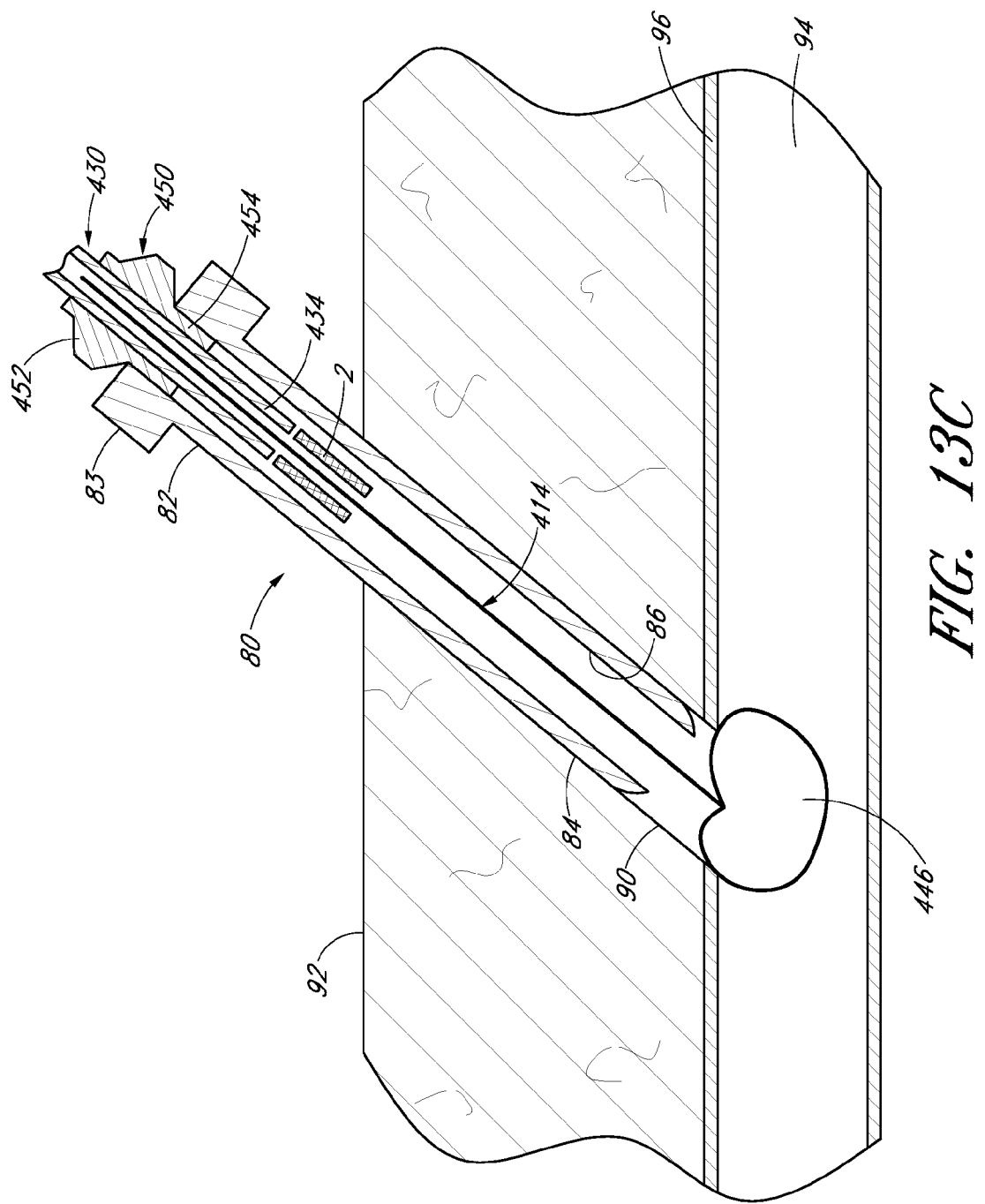

Turning to FIGS. 13A-13C, the apparatus 410 may be used to position and deliver the sealant 2 within a puncture 90, e.g., extravascularly just above or otherwise adjacent to an arteriotomy in a blood vessel or other body lumen 94 communicating with a puncture 90, as described further elsewhere herein. As shown in FIG. 13A, the cartridge 416, with the sleeve 450 located over the sealant 2 and the distal end 434 of the support member 430, may be initially provided on the proximal end 442 of the positioning member 414. For example, the hub 448 on the positioning member 414 and the housing 423 on the cartridge 416 may be initially connected to one another, e.g., using one or more releasable detents (not shown). As shown in FIG. 13B, the cartridge 416 may be slidable distally along the positioning member 414, e.g., by disconnecting the housing 423 from the hub 448, and then advancing the cartridge 416 towards the positioning element 446.

With continued reference to FIGS. 13A-13C, the apparatus 40 can generally be used in cooperation with an introducer sheath 80 to deliver the sealant 2 into a puncture 90. The introducer sheath 80 may part of a system or kit including the apparatus 410 or may be an independent device. Generally, the introducer sheath 80 includes a proximal end 82, a distal end 84 sized for insertion into a puncture 90 through tissue, and a lumen 86 extending between the proximal and distal ends 82, 84. The introducer sheath 80 may be formed from a substantially rigid, semi-rigid, and/or flexible tubular body including a hub 83 on the proximal end 82. The introducer sheath 80 may have sufficient length to extend from a patient's skin through any intervening tissue into a blood vessel or other body lumen, e.g., having a length between about ten centimeters and twenty centimeters (10-20 cm), and may have an outer diameter between about 1.6 millimeters and five millimeters (1.6-5 mm). The distal end 84 may be tapered and/or may include a substantially atraumatic distal tip for facilitating advancement through a puncture.

The introducer sheath 80 may be formed using known materials and/or methods, e.g., plastic with the tubular body and hub 83 substantially permanently connected together, e.g., using an interference fit, one or more mating connectors (not shown), bonding with adhesive, ultrasonic welding, and the like. The hub 83 can generally include one or more seals, e.g., one or more hemostatic seals (not shown) therein, which may prevent flow of blood or other fluids out of the hub 83 from the lumen 86, yet accommodate insertion of one or more instruments into the lumen 86, such as the positioning member 414 and/or cartridge 416. Optionally, as shown, the hub 83 may include a side port 89 communicating with the lumen 86, e.g., for coupling a source of saline or other fluid (not shown) to the hub 83.

Initially, as shown in FIG. 13A, the positioning member 414 may be introduced into and/or through the lumen 86 of the introducer sheath 80, e.g., with the expandable positioning element 446 in a collapsed condition. The cartridge 416, along with the sealant 2 and support member 430, may be provided initially on the proximal end 442 of the positioning member 440, e.g., as shown in FIG. 12. Thus, the distal end 454 of the sleeve 450 may initially be located outside the puncture 90 and spaced apart from the hub 83 when the positioning member 414 is advanced into the puncture 90.

Still referring to FIG. 13A, the distal end 444 of the positioning member 414 may be inserted through the puncture 90 (via the introducer sheath 80) and into the vessel 94. Once the positioning element 446 is disposed within the vessel 94, i.e., beyond the distal end 84 of the introducer sheath 80, the positioning element 446 may be expanded to an enlarged condition, and the positioning member 414 may be at least partially withdrawn until the positioning element 446 contacts the vessel wall 96, e.g., similar to other embodiments herein.

Turning to FIGS. 13B and 13C, the cartridge 416 (carrying the sealant 2) may be advanced distally over the positioning member 414 towards the introducer sheath 80. As the cartridge 416 is advanced, the sleeve 450 may contact the introducer sheath 80, which may prevent further advancement of the sleeve 450. For example, the distal portion 454 of the sleeve 450 may at least partially enter the hub 83 of the introducer sheath 80 and the proximal portion 452 of the sleeve 450 may abut the hub 83, as best seen in FIG. 13C, thereby preventing further advancement of the sleeve 450. If the sleeve 450 is releasably attached to the support member 430, advancement of the cartridge 416 to this point may release the sleeve 450 from the distal end 434 of the support member 430.

The cartridge 416 may be further advanced distally toward the positioning element 446, whereupon the sleeve 450 may remain substantially stationary relative to the introducer sheath 80 and, consequently, slide proximally over the support member 430. Thus, the distal end 434 of the support member 430 may exit the distal portion 454 of the sleeve 450 and enter the introducer sheath lumen 86, thereby ejecting the sealant 2 from the sleeve 450 and into the sheath lumen 86, as shown in FIG. 13C. The distal portion 454 of the sleeve 450 may have sufficient length and/or other features to at least partially open the valve(s) (not shown) within the introducer sheath hub 83, e.g., to facilitate the sealant 2 and distal end 434 of the support member 430 being advanced into the introducer sheath lumen 86. Thus, the sleeve 450 may protect the sealant 2 until the sealant 2 passes through the hub 83 and any valves therein, into the lumen 86 of the introducer sheath 80.

The cartridge 416 may then be advanced to direct the sealant 2 through the sheath lumen 86 until the sealant 2 is disposed adjacent the positioning element 446 and/or the vessel wall 94. Optionally, the cartridge 416 may be advanced until a component of the cartridge 416 encounters a stop on the positioning member 414, thereby preventing further advancement of the cartridge 416 and/or spacing the sealant 2 a predetermined distance from the positioning element 446, e.g., about zero to five millimeters (0-5 mm) from the positioning element 4. In some embodiments, the cartridge 416 may be advanced until the sealant 2 contacts the positioning element 446 and/or vessel wall 94 and resistance is detected.

Thereafter, the introducer sheath 80 may be at least partially retracted, to expose the sealant 2 within the puncture 90 beyond the introducer sheath distal end 84. Optionally, the sleeve 450 may include one or more locking elements (not shown) that may couple the introducer sheath 80 to the sleeve 450. Thus, if the user pulls proximally on the sleeve 450 rather than the introducer sheath 80, the introducer sheath 80 and sleeve 450 may be withdrawn together to retract the distal end 84 of the introducer sheath 80.

As the introducer sheath 80 is retracted, the support member 430 may prevent substantial proximal movement of the sealant 2, thereby exposing the sealant 2 within the puncture 90. When the sealant 2 is exposed within the puncture 90, the sealant 2 may be exposed to blood and/or other body fluids within the puncture 90. This exposure may cause the sealant 2 to absorb fluid and/or otherwise expand within the puncture 90, e.g., to provide hemostasis.

If desired, once the sealant 2 is exposed within the puncture 90, the support member 430 may be advanced to compress or tamp the sealant 2, e.g., against the positioning element 446. Optionally, the support member 430 may include one or more markers (not shown), e.g., on or adjacent the proximal end 432, and the support member 430 may be advanced into the puncture 90 a desired distance, which may be confirmed by monitoring the markers. In addition or alternatively, the positioning member 414 may include a detent or other feature over which the support member 430 may pass when advanced a predetermined distance. The detent may provide an audible confirmation that the support member 430 has been advanced the predetermined distance (in addition or instead of the visible confirmation provided by the markers).

Once the sealant 2 has been exposed for sufficient time and/or tamped by the support member 430, the positioning element 446 may be collapsed, and the positioning member 414 withdrawn from the vessel 94 and puncture 90, e.g., pulling the collapsed positioning element 446 through the sealant 2 and support member 430. The support member 430 may be maintained substantially stationary during withdrawal of the positioning member 414, e.g., to prevent migration and/or dislodgment of the sealant 2 within the puncture 90. Optionally, the cartridge 416 may include an auto-retraction assembly, similar to other embodiments herein, that may retract the positioning member 414 automatically. Once the positioning member 414 is completely removed, the support member 430 may be removed from the puncture 90, leaving the sealant 2 within the puncture 90.

Turning to FIGS. 16A-16D, another embodiment of an apparatus 710 is shown that generally includes a positioning member 714 and a cartridge 716 carried on the positioning member 714 for delivering a sealant 2 therein into a puncture (not shown). Similar to the apparatus 410 of FIG. 12, the cartridge 716 can include a sealant sleeve 750 carrying sealant 2 therein, and surrounding a distal end 734 of a support member 730 adjacent the sealant 2, and a handle or hub 723 on the proximal end 732 of the support member 730. The sealant sleeve 750 can include a relatively large diameter proximal portion 752 surrounding a portion of the distal end 734 of the support member 730, e.g., sized to abut or otherwise contact a hub or proximal end 783 of an introducer sheath 780, such as that shown in FIG. 16D, and a relatively small diameter distal portion 754 surrounding the sealant 2, e.g., sized to enter the hub 783 and/or lumen 786 of the introducer sheath 780. The hub 783 can include a cavity adapted to releasably receive the small diameter portion of the sealant sleeve. Unlike the apparatus 410, the cartridge 716 can be initially provided such that the sealant sleeve 750 and sealant 2 are located immediately adjacent a positioning element 746 of the positioning member 714.

The handle 723 can include an outer housing or shroud 772 surrounding an inner housing or frame 774 and one or more actuators 760-764 for allowing and/or causing movement of one or more components of the apparatus 710 relative to one another, as described further below. As shown, the outer housing 772 includes a first opening or slot 773 within which first and second actuators 760 and 762 are provided, and a second slot 775 within which third actuator 764 is provided. The opening 773 may include one or more features for interacting with first and/or second actuators 760, 762, as described further below.

The inner housing 774 may be slidable axially relative the outer housing 772, e.g., between an initial, proximal position and a distal position. For example, the outer housing 772 may include clam-shell halves or other components that may be attached around the inner housing 774 such that cooperating rails and grooves (not shown) allow the inner housing 774 to slide axially without substantial lateral motion. In an exemplary embodiment, one or more elongate ribs or rails (not shown) may be molded or otherwise provided on the inner surfaces of the outer housing 772 that may be slidably received between rails or grooves (also not shown) in the inner housing 774.

The handle 723 can include a distal shroud 776 integrally formed with or otherwise extending from the outer housing 772. One or more detents or other features, e.g., a pair of tines 778, may be provided on the shroud 776 for engaging the hub 723 to an introducer sheath, such as the sheath 780 shown in FIG. 16D. For example, the sheath 780 may include a hub 783 that includes a pair of pockets 783a that extend axially along opposite sides of the hub 783. The tines 778 include tabs or detents 778a that may be slidably received within the pockets 783a, e.g., when the apparatus 710 is introduced into the sheath 780 during use, as described below. The relative length of the tines 778 and pockets 783a are configured such that the detents 783a pass through the pockets 783a and extend out the distal ends thereof. The detents 783a may include ramped or tapered distal edges that facilitate insertion, and blunt proximal edges that may engage distal ends of the pockets 783a to prevent the tines 778 from being withdrawn back through the pockets 783a, thereby coupling movement of the sheath 780 and outer housing 772 of the hub 723, also as described further below.

Figure 16A:
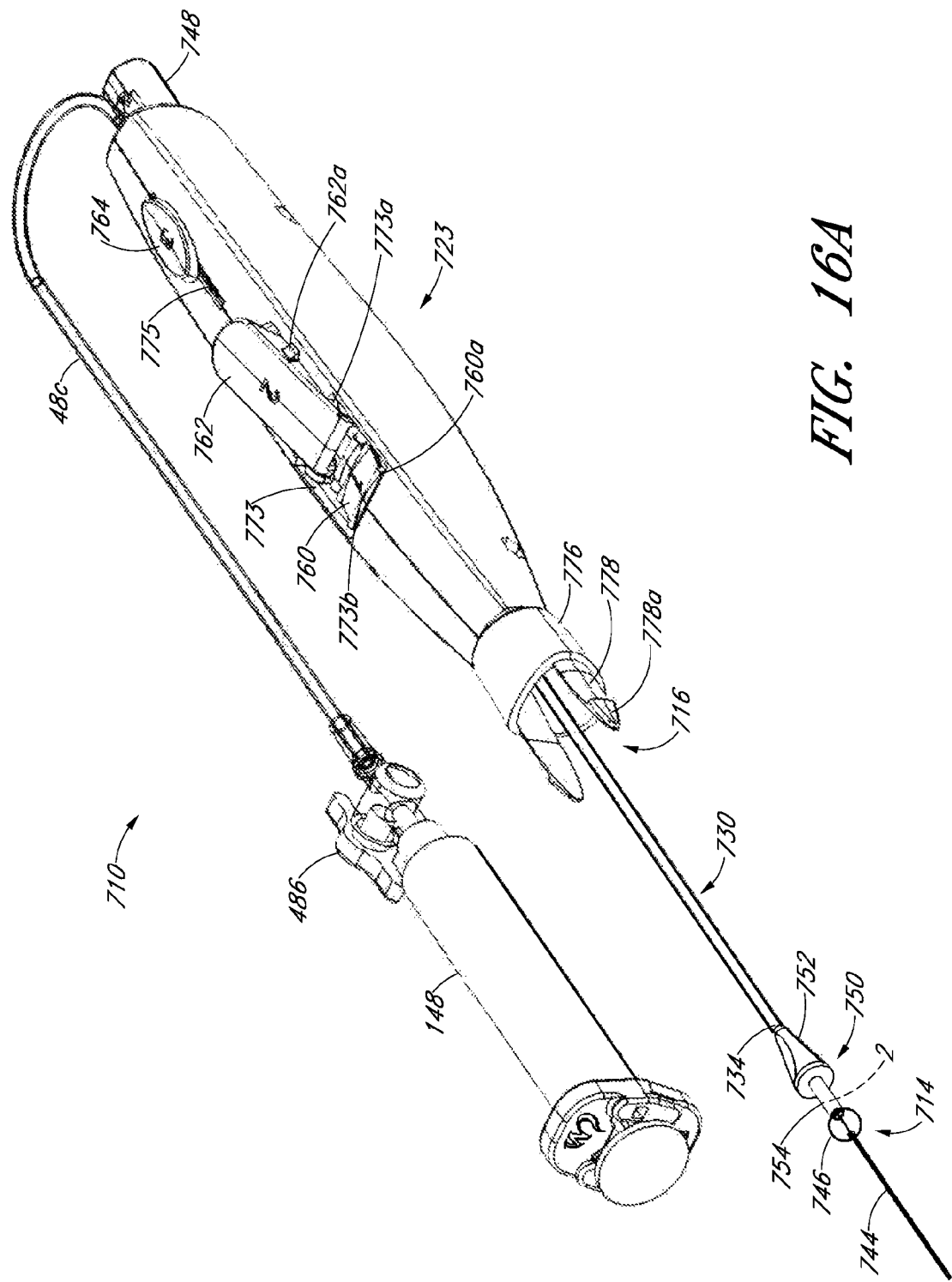
FIGS. 16A and 16B are perspective and side views, respectively, of another embodiment of an apparatus for delivering a sealant into a puncture through tissue.
Figure 16B:
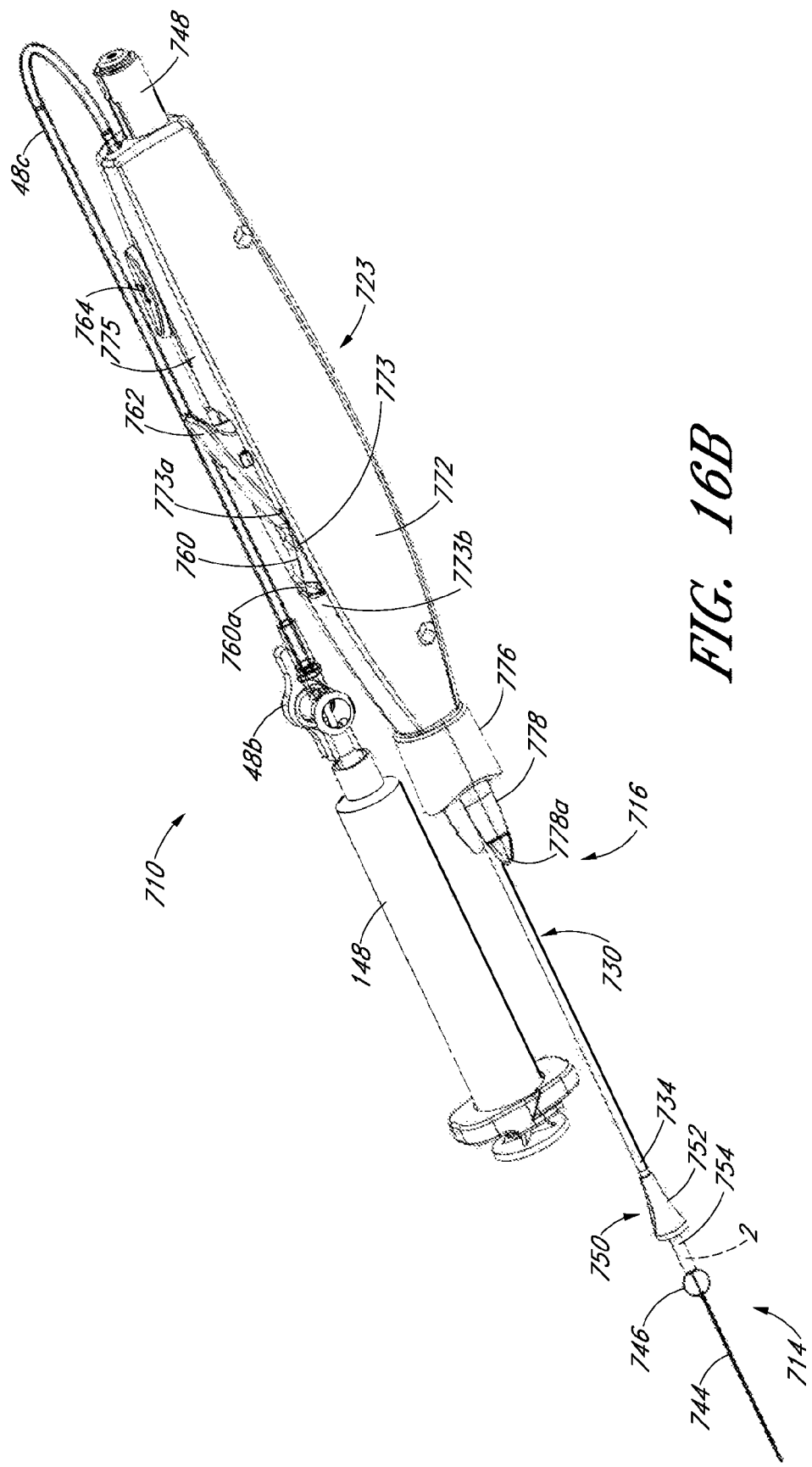
Figure 16C:
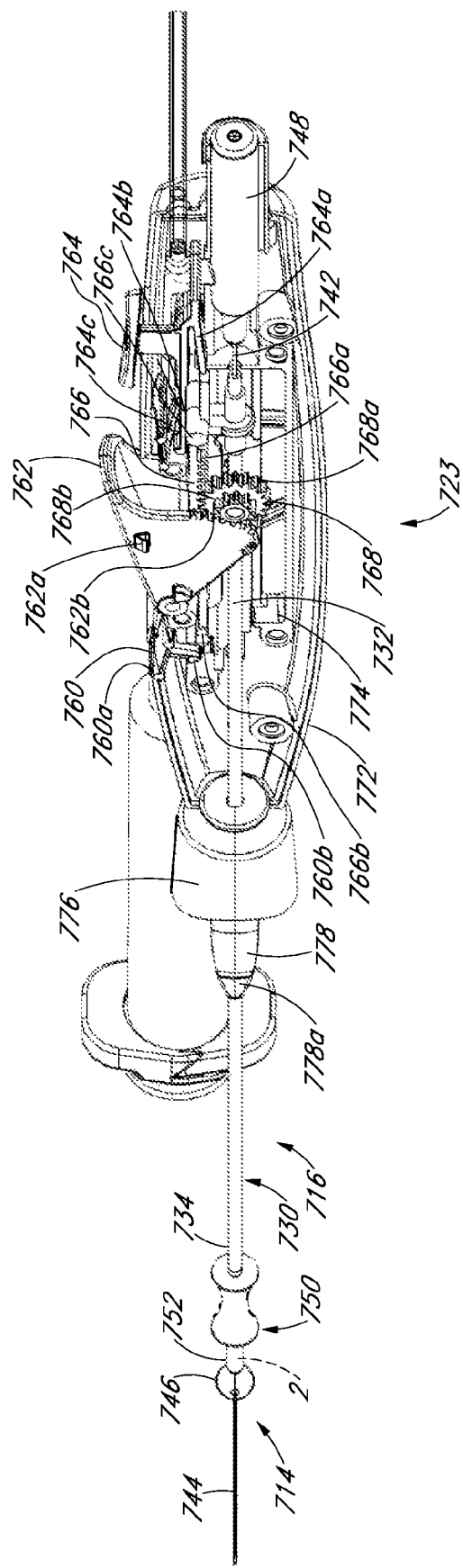
FIG. 16C is a side view of the apparatus of FIGS. 16A and 16B with a portion of an outer housing removed to show internal components of the apparatus.
Figure 16D:
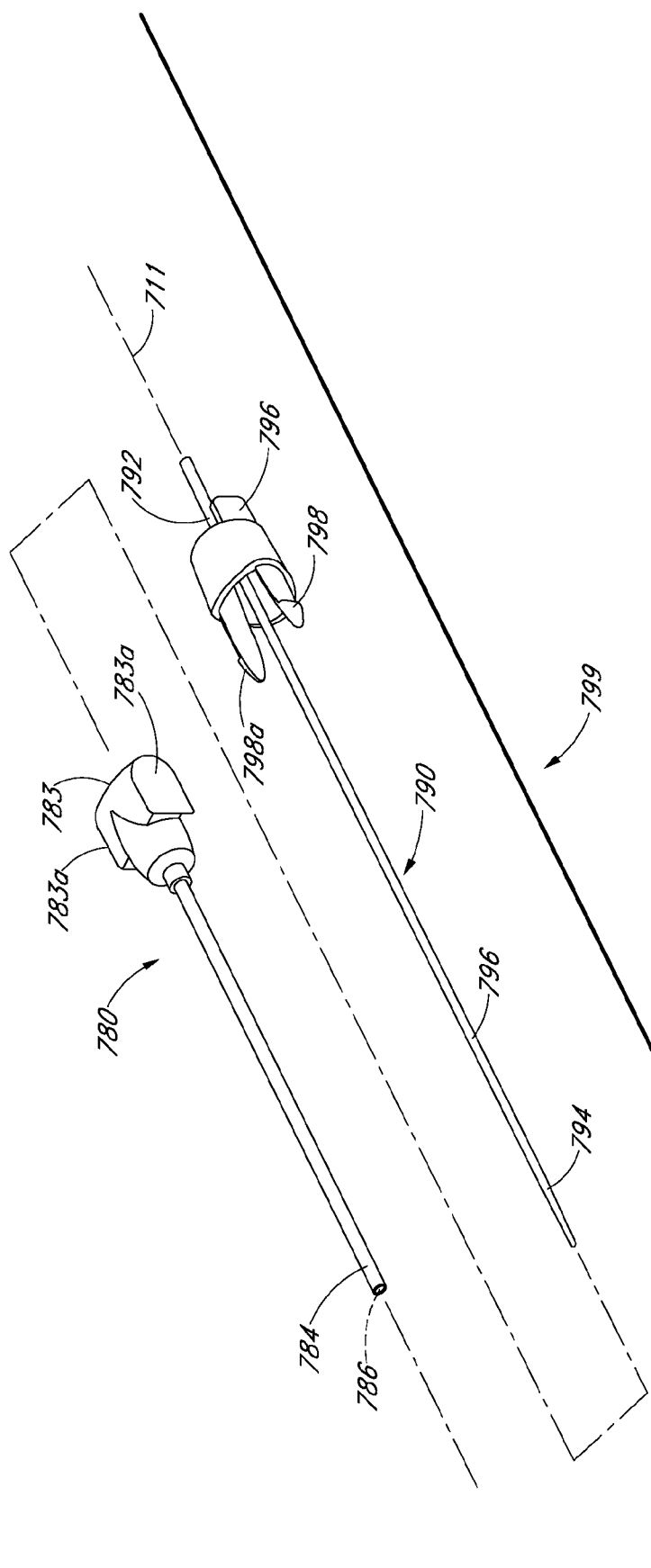
FIG. 16D is a perspective view of an introducer sheath and dilator assembly that may be used in cooperation with the apparatus of FIGS. 16A-16C.

As can be seen in FIG. 16C, the apparatus 710 can include a rack and pinion arrangement that may be similar to any of the other embodiments herein. For example, as shown, a rack 766 may be coupled to a proximal end 732 of the support member 730 and slidably received within the outer and/or inner housings 772, 774. A pinion 768 may be rotatably mounted to the inner housing 774 that is coupled to the rack 766 by a plurality of interlocking teeth 766a, 768a, e.g., similar to other embodiments herein. The second or support actuator 762, e.g., a button pivotably coupled to the inner housing 774, is coupled to the pinion 768, e.g., by interlocking teeth 762b, 768b, for selectively rotating the pinion 768. For example, as described further below, the second actuator 762 may be depressed to cause the pinion 768 to rotate, thereby causing the rack 766 to advance distally, thereby advancing the support member 730.

Optionally, as shown, a first or locking actuator 760 may be provided on the hub 723 for preventing relative movement of the outer and inner/or housings 772, 774 until activated and/or limiting movement of the support member 730. For example, as best seen in FIG. 16C, the locking actuator 760 may be pivotably mounted to the inner housing 774 and include a distal end 760a that abuts or otherwise engages a distal edge 773b of the opening 773 in the outer housing 772. As a result, the inner housing 774 may be substantially secured in the proximal position and cannot be directed towards the distal position until the locking actuator 760 is activated to disengage the distal end 760a of the actuator 760 from the distal edge 773b of the opening 773.

In addition or alternatively, the first actuator 760 may include a detent or other locking feature 760b for selectively locking the support member 730 relative to the inner housing 774. For example, as shown in FIG. 16C, a detent 760b extends inwardly from the first actuator 760 that is not engaged with any other features. When the first actuator 760 is activated, i.e., directed inwardly to disengage the distal end 760a of the actuator 760 from the distal edge 773b of the outer housing 772, the detent 760b may drop downwardly into the inner housing 774. As discussed herein, once the inner and outer housing portions 774, 772 are movable relative to one another, the handle 723 can be moved proximally causing the outer sheath 780 to retract and uncover the sealant.

Subsequently, when the support actuator 762 is subsequently activated, the rack 766 may advance, causing the support member 730 to tamp the sealant toward the arteriotomy, as described herein, until a distal end 766b of the rack 766 passes under the detent 760b and the detent 760b is captured in a pocket (not shown) therein. With detent 760b captured in the pocket, the rack 766 cannot be directed proximally, thereby preventing proximal movement of the support member 730 coupled to the rack 766.

The apparatus 710 may also include a third or balloon retraction actuator 764, e.g., for selectively retracting the positioning element 746 through the sealant 2 after deployment, similar to other embodiments herein. For example, as shown in FIG. 16C, the third actuator 764 may be slidably mounted to the inner housing 774 and may be selectively coupled to the hub 748 of the positioning member 714. The hub 748 may be constructed and/or operate similar to any of the other embodiments herein or in the references incorporated by reference herein.

Initially, the third actuator 764 may be coupled with the inner housing 774 but may be decoupled from the inner housing 774 once the sealant 2 has been deployed and/or tamped. For example, as best seen in FIG. 16C, the third actuator 764 may include a third arm 764c that may be decoupled from the inner housing 774 such that proximal movement of the third actuator 764 relative to the outer and/or inner housings 772, 774 causes similar proximal movement of the hub 748, thereby directing the positioning element 746 proximally, similar to other embodiments herein.

In addition, the third actuator 764 can include a second arm 764b that may be slidably positioned adjacent a proximal end 766c of the rack 766. With the second arm 764b positioned in this manner, the third arm 764c may remain coupled with the hub 748. When the rack 766 is directed distally, e.g., by activating the second actuator 762, the second arm 764b may slide off the proximal end 766c of the rack 766, thereby decoupling the third arm 764c from the inner housing 774. For example, as shown, a spring or other biasing mechanism 764a may be provided on the third actuator 764 (or optionally, the outer housing 772) for biasing the second arm 764b outwardly when the rack 766 is directed distally to clear the second arm 764b from the proximal end 766c of the rack 766. In addition, the spring or biasing mechanism 764a may require that the actuator be depressed in order to decouple the third arm 764c from the inner housing thereby preventing inadvertent movement of the positioning element 746. Thereafter, the third actuator 764 may be directed proximally to retract the hub 748 and the positioning element 746.

The apparatus 710 may be used to deliver the sealant 2 into a puncture, e.g., communicating with a body lumen within a patient's body, similar to other embodiments herein. Initially, the introducer sheath 780 shown in FIG. 16D may be positioned through the puncture into the body lumen, e.g., as described elsewhere herein.

Optionally, the introducer sheath 780 may be provided as part of an introducer kit, .e.g., including a dilator 790 and a guidewire 799, and/or a system also including the apparatus 710. The dilator 790 may include a proximal end 792 and a distal end 794 sized to be slidably received through the lumen 786 of the introducer sheath 780, e.g., terminating a tapered, atraumatic and/or other distal tip to facilitate introduction of the dilator 790 and introducer sheath 780 into a puncture (not shown), e.g., over the guidewire 799. As shown, the dilator 790 can include a proximal housing 796 include tines 798 and detents 798a configured similar to the distal shroud 776 of the apparatus 710. The dilator 790 may be directed into the hub 783 and lumen 786 of the introducer sheath 780 until the tines 798 enter and the detents 798a exit the passages 783a in the hub 783.

Thus, the dilator 790 and introducer sheath 780 may be coupled together such that the guidewire 799 (already placed through a puncture into a body lumen, not shown, as described elsewhere herein) may be backloaded into the distal end 794 and lumen 796 of the dilator 790 to introduce the dilator 790 and introducer sheath 780 into the puncture. Once the introducer sheath 780 is positioned as desired, the tines 798 may be squeezed inwardly to disengage the detents 798a from the pockets 783a and allow the dilator 790 to be withdrawn from the lumen 796 of the introducer sheath 790. The introducer sheath 780 may then be used to access the body lumen and perform one or more procedures, as described elsewhere herein.

When it is desired to seal the puncture, any instruments introduced through the introducer sheath 780 may be removed and the apparatus 710 may be prepared, e.g., as shown in FIGS. 16A and 16B. With the positioning element 746 collapsed, the distal end 744 of the positioning member 714 may be directed into the hub 783 of the introducer sheath 780, through the lumen 786, and into the body lumen. Because the sealant sleeve 750 and sealant 2 are located immediately adjacent the positioning element 746, as the distal end 744 enters the introducer sheath 780, the sleeve 750 may contact the introducer sheath 780, which may prevent further advancement of the sleeve 750. For example, the distal portion 754 of the sleeve 750 may at least partially enter the hub 783 of the introducer sheath 780 and the proximal portion 752 of the sleeve 750 may abut the hub 783, thereby preventing further advancement of the sleeve 750. If the sleeve 450 is releasably attached to the support member 730, advancement of the positioning member 714 may release the sleeve 750 from the distal end 734 of the support member 730.

The positioning member 714 may be advanced further into the introducer sheath 780, whereupon the sleeve 750 may remain substantially stationary relative to the introducer sheath 780 and, consequently, slide proximally over the support member 730. Thus, the distal end 734 of the support member 730 may exit the distal portion 754 of the sleeve 750 and enter the introducer sheath lumen 786, thereby ejecting the sealant 2 from the sleeve 750 and into the sheath lumen 786, similar to other embodiments herein. Optionally, the distal portion 754 of the sleeve 750 may have sufficient length and/or other features to at least partially open the valve(s) (not shown) within the introducer sheath hub 783, e.g., to facilitate the sealant 2 and distal end 734 of the support member 730 being advanced into the introducer sheath lumen 786. Thus, the sleeve 750 may protect the sealant 2 until the sealant 2 passes through the hub 783 and any valves therein, into the lumen 786 of the introducer sheath 780.

The positioning member 714 may then be advanced until the positioning element 746 is disposed beyond the distal end 784 of the introducer sheath 780, i.e., within the body lumen. As this occurs, the tines 778 on the housing shroud 776 may be aligned with and enter the pockets 783a on the sheath hub 783, e.g., until the detents 778a engage the distal ends of the pockets 783a, as described above. With the detents 778a engaged with the pockets 783a, the introducer sheath 780 and outer housing 772 may be coupled together such that they move together, similar to other embodiments herein.

The relative length of the positioning member 714 and the introducer sheath 780 may be configured such that the sealant 2 remains within the sheath lumen 786, e.g., proximal to the distal end 784 of the introducer sheath 780, while the positioning element 746 is exposed beyond the distal end 784. The positioning element 746 may then be expanded, e.g., by inflating the positioning element 746 using fluid from the syringe 148 and/or otherwise similar to other embodiments herein. The entire apparatus 710 and introducer sheath 780 may then be retracted (regardless of whether the apparatus hub 723 or the sheath hub 783 is manipulated) until the expanded positioning element 746 contacts the wall of the body lumen adjacent the puncture.

Once properly positioned, the first actuator 760 may be activated to decouple movement of the outer and inner members 772, 774. For example, while holding the outer housing 772, the first actuator 760 may be pressed inwardly to disengage the distal end 760a of the first actuator 760 from the distal end 773b of the outer housing 772, and then the outer housing 772 may be retracted proximally, i.e., away from the patient and puncture.

With the inner housing 774 coupled to the positioning member 714 and support member 730, this action causes the inner housing 774 to slide within the outer housing 772, i.e., from the proximal position (shown in FIGS. 16A-16C) to the distal position, thereby retracting the introducer sheath 780 relative to the support member 730 and exposing the sealant 2 within the puncture adjacent the positioning element 746.

With the inner housing 774 in the distal position, the second actuator 762 may be activated to advance the support member 730, e.g., to tamp or compress the sealant 2 against the expanded positioning element 746 and/or outer wall of the body lumen, e.g., over an arteriotomy, similar to other embodiments herein. For example, with particular reference to FIG. 16C, the second actuator 762 may be pressed inwardly, thereby rotating the pinion 768, advancing the rack 766, and consequently advancing the support member 730 to direct the distal end 734 towards the positioning element 746 and compress the sealant 2 therebetween.

Optionally, the second actuator 762 may include one or more features, e.g., tabs or detents 762a that may be engaged with the outer housing 772 when the second actuator 762 is fully depressed. For example, as shown in FIGS. 16A and 16B, the opening 773 in the outer housing 772 may include one or more pockets or recesses 773a that may be aligned with the tabs 762a on the second actuator 762 when the inner housing 774 has been directed fully to the distal position. With the tabs 762a received within the pockets 773a, the inner housing 774 cannot be moved proximally relative to the outer housing 772, thereby securing the outer and inner housings 772, 774 relative to one another.

Once the sealant 2 has been exposed for sufficient time and/or tamped by the support member 730, the positioning element 746 may be collapsed, and the positioning member 714 withdrawn from the body lumen, e.g., pulling the collapsed positioning element 746 through the sealant 2 and support member 730. For example, the positioning element 746 may be deflated using the syringe 148, and then the third actuator 764 may be activated to withdraw the collapsed positioning element 746 through the sealant 2 and into the distal end 734 of the support member 730, similar to other embodiments herein.

Optionally, as described above, the third actuator 764 may remain coupled with the inner housing 774 until the rack 766 is advanced sufficiently to release the third arm 764c of the third actuator. Thereafter, proximal movement of the third actuator 764 relative to the outer and inner housings 772, 774 causes the hub 748 and the entire positioning member 714 to also move proximally, thereby withdrawing the positioning element 746 through the sealant 2 into the distal end 734 of the support member 730. The length of the slot 775 in the outer housing 772 may be configured to withdraw the positioning element 746 a desired distance into the distal end 734.

Once the positioning element 746 is withdrawn through the sealant 2, the entire apparatus 710 may be withdrawn to remove the support member 730 from the puncture, leaving the sealant 2 within the puncture.

Figure 14:
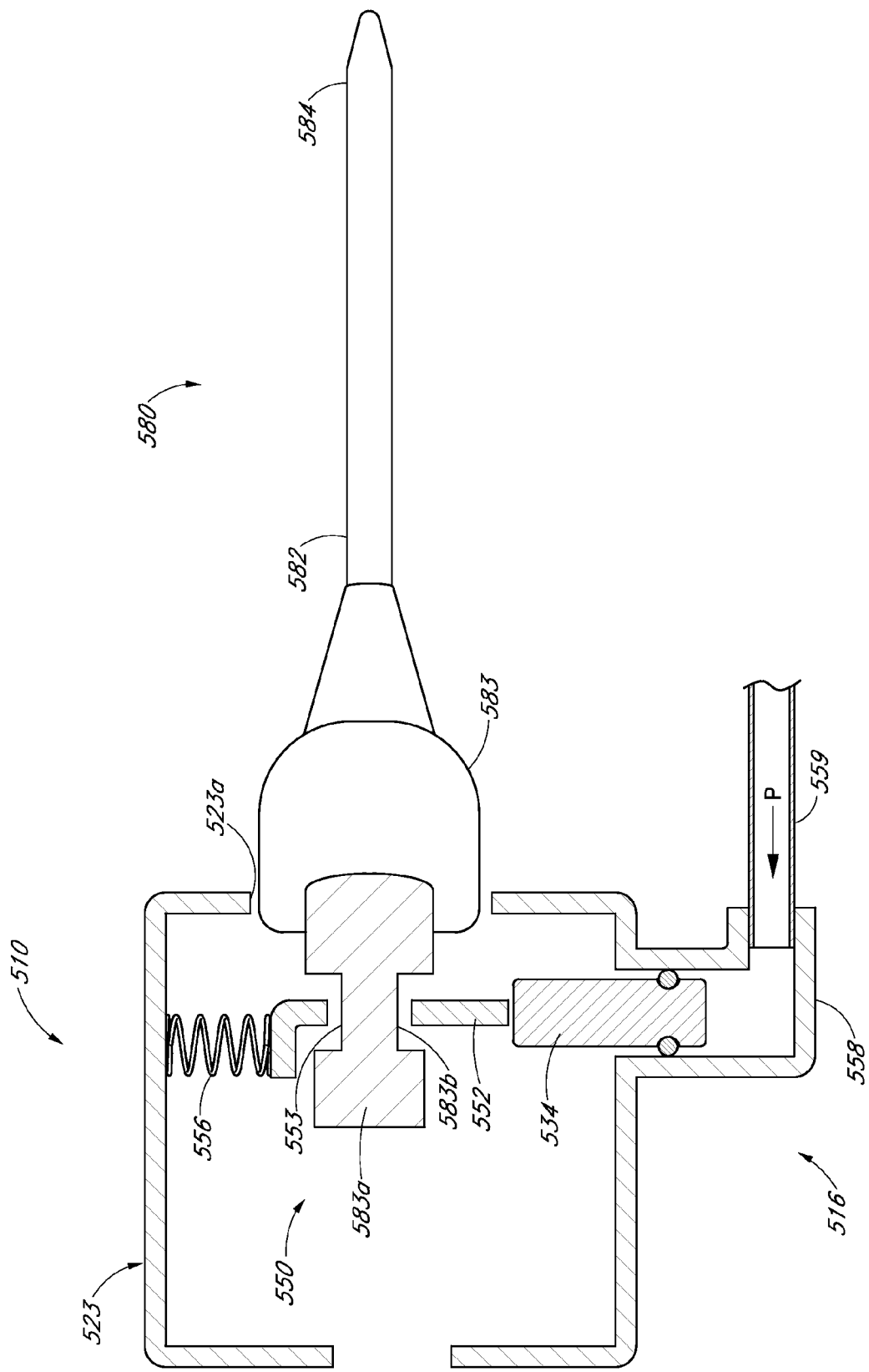
FIG. 14 is a partial cross-sectional side view of an exemplary embodiment of a sheath catch that may be provided on an apparatus for delivering a sealant.

Turning to FIG. 14, an exemplary embodiment of a sheath catch assembly 550 is shown that may be provided on an apparatus 510 for sealing a puncture and/or introducer sheath 580. Generally, the apparatus 510 may include a positioning member (not shown) and a cartridge 516, similar to any of the other embodiments herein. As shown, the cartridge 516 includes a housing 523, which may be coupled to a tubular member carrying a sealant and/or a support member (not shown for simplicity). The introducer sheath 580 includes a tubular body including proximal and distal ends 582, 584, and a hub 583 on the proximal end 582, also generally similar to other embodiments herein.

As shown, the sheath hub 583 includes a catch adapter 583a including a pocket 583b therein. The housing 523 of the cartridge 516 includes the sheath catch assembly 550 therein, e.g., within the shroud 23a shown in FIG. 2B, which includes a sheath catch 552 slidable within the housing 523, e.g., between first and second lateral positions. For example, the housing 523 may include a distal passage 523a into which the catch adapter 583a may be received when the cartridge 516 is advanced into the introducer sheath 580, similar to any of the embodiments described elsewhere herein.

With the sheath catch 552 in a first position, the catch adapter 583a may pass through the distal passage 523a and into an opening 553 in the sheath catch 552, e.g., until the pocket 583b on the catch adapter 583a is aligned with the sheath catch 552. Thereafter, if the sheath catch 552 is directed laterally to the second position, the sheath catch 552 may enter the pocket 583b, thereby preventing subsequent axial movement of the introducer sheath 580 relative to the housing 523.

In the embodiment shown in FIG. 14, the sheath catch 552 may be biased to one of the first and second positions, e.g., by a spring 556 or other biasing mechanism. For example, the sheath catch 552 may be biased towards the first position, such that the default position for the sheath catch 552 allows the cartridge 516 to be separated from the introducer sheath 580. To overcome the bias of the spring 556, a hydraulic actuator may be provided that includes a piston 534 slidable within a chamber 558. As shown, the piston 534 may be movable laterally within the chamber to cause the piston 534 to engage the sheath catch 552, e.g., to overcome the bias of the spring 556 and move the sheath catch 552 from the first position to the second position.

In addition, as shown, the chamber 558 may communicate with a fluid line 559 through which fluid may be delivered and/or evacuated, thereby directing the piston 534 between its engaged and disengaged positions. In some embodiments, the fluid line 559 may be coupled to the same inflation line as the positioning element on the positioning member (not shown). For example, with additional reference to FIG. 1A, if the syringe 148 is depressed to deliver fluid through the inflation line 48c to inflate the balloon 46, the fluid may substantially simultaneously be delivered into to the fluid line 559, thereby directing the piston 534 to engage the sheath catch 552 to the second position, thereby coupling the introducer sheath 580 to the housing 523. Thereafter, if the syringe 148 is used to evacuate fluid to collapse the balloon 46, the fluid may also be evacuated from the fluid line 559, thereby disengaging the piston 534 and sheath catch 552, and allowing the cartridge 516 to be separated from the introducer sheath 580.

Thus, the sheath catch assembly 550 may also provide a safety feature that allows immediate separation of the cartridge 516 from the introducer sheath 580 if fluid pressure is lost in the fluid line 559, e.g., if the balloon 46 ruptures or otherwise leaks fluid. Without the fluid pressure in the fluid line 559, the spring 556 may automatically direct the sheath catch 552 to the first position, and disengage the sheath catch 552 from the sheath adapter 583a. In addition, during deflation, the fluid flow rate from the fluid line 599 for the piston 534 may be slower than from the balloon 46 such that the balloon 46 deflates before sheath catch assembly 550 releases, which may ensure that the inflated balloon 46 is not pulled by the spring 556. Further, if the balloon 46 ruptures, the sheath catch assembly 550 may detach so that access to the body lumen is maintained even if the positioning member 14 is withdrawn from the body lumen since the introducer sheath 580 may remain within the puncture.

In some embodiments, other features may be provided on the cartridge, e.g., on the housing, of any of the embodiments herein to secure an introducer sheath relative to the cartridge. For example, within the shroud 23a shown in FIG. 2B, a simplified sheath catch may be provided that automatically engages with features on the hub of an introducer sheath (not shown). For example, a detent may be provided within the shroud 23a, e.g., on a tubular sleeve or other support (not shown) that may be configured to freely enter the hub of the introducer sheath, yet prevent subsequent removal, e.g., similar to embodiments disclosed in U.S. Pat. No. 7,993,367. If such a sheath lock is provided on the tubular member of the cartridge, with the sheath engaged by the sheath lock, a deployment mechanism that retracts the tubular member may also automatically retract the introducer sheath as well.

For example, after an apparatus, such as the apparatus 210 of FIGS. 8A-8C is inserted into an introducer sheath (not shown), the sheath lock may couple the sheath hub to the housing 223 (e.g., within a shroud 23a, similar to that shown in FIG. 2B). With the positioning element 246 expanded within a vessel, the entire apparatus 210 and introducer sheath may then be withdrawn together until the positioning element 246 is positioned against the vessel wall, e.g., similar to the method shown in FIGS. 10A and 10B (except that the cartridge 216 is positioned within the sheath). Thus, in some embodiments, the expanded positioning element 246 is not used to pull the introducer sheath back into the puncture, which may reduce stress on the positioning element 246.

Optionally, the apparatus 210 may include a release feature that allows the cartridge 216 and introducer sheath to be retracted further after the positioning element 246 is positioned against the vessel wall. For example, when the positioning element 246 is positioned against the vessel wall, an actuator of the release feature, e.g., on the housing 223, may be activated, which allows the cartridge 216 and sheath to be retracted relative to the positioning member 214 a predetermined distance, e.g., about 1.5 cm. Thus, the distal end 224 of the tubular member 220 and the sheath may be retracted away from the positioning element 246, which may overcome friction in the puncture around the sheath immediately before deploying the sealant 2. For example, otherwise, tissue surrounding a relatively small profile puncture may impose friction on the introducer sheath resisting retraction, which may cause the apparatus to advance relative to the sheath when the deployment mechanism 260 is activated, which may direct the positioning element 246 and sealant 2 further into the puncture (and potentially into the vessel), rather than only retracting the tubular member 220 and sheath to deploy the sealant 2 outside the vessel.

Optionally, a sheath stabilizer (not shown) may be provided that may be coupled between the housing 223 and the introducer sheath, e.g., to prevent the cartridge 216 from moving distally relative to the sheath.

Turning to FIGS. 15A and 15B, another exemplary embodiment of an apparatus 610 is shown that includes a bleed back assembly 650 on a housing 623 of the cartridge 616. Generally, the apparatus 610 can include a cartridge 616 including a tubular member carrying a sealant and a support member (not shown) coupled to the housing 623. The apparatus 610 may also include a positioning member, similar to other embodiments herein, or the positioning member may be omitted.

The bleed back assembly 650 extends from the housing 623 and may include a sheath catch 652, which may be received within a hub 83 or otherwise coupled to an introducer sheath 80, similar to other embodiments herein. The bleed back assembly 650 also includes a lumen 653 communicating with a bleed back port 654 and aligned to communicate with the lumen 86 of the introducer sheath 80. For example, as best seen in FIG. 15B, during use, the cartridge 616, e.g., the tubular member (not shown), may be advanced into the sheath lumen 86 until the sheath catch 652 enters the sheath hub 83. As shown, the sheath catch 652 may include a tip 652a that extends into and/or opens the valve(s) 83a of the sheath hub 83. In addition, the sheath catch 652 may resiliently or otherwise engage a wall 83b of the hub 83, thereby preventing subsequent separation of the introducer sheath 80 from the housing 623.

During use, the apparatus 610 (with the tubular member distal end disposed adjacent the positioning element, not shown) may be introduced into the introducer sheath 80, similar to other embodiments herein. The relative lengths of the introducer sheath 80 and the positioning member may be predetermined such that the distal end 84 of the introducer sheath 80 is offset from the positioning element by a predetermined distance when the sheath catch 652 engages the sheath hub 83. For example, the distal 84 may be spaced between 0.1 and two millimeters (0.1-2.0 mm) from the positioning element when the sheath catch 652 is engaged.

Due to this distance and the space around the cartridge within the sheath lumen 86, blood may flow through the sheath lumen 86 when the distal end 84 is exposed within the vessel. The pressure within the vessel may cause blood flow through the sheath lumen 86 into the lumen 653 of the sheath catch assembly 650 and out the bleed back port 654. When the apparatus 610 is withdrawn to direct the expanded positioning element against the vessel wall, the positioning element may isolate the puncture, and consequently the sheath lumen 84, from vessel pressure, and so blood flow through the sheath lumen 84 and out the bleed back port 654 will discontinue, providing a visual confirmation that the positioning element is in position against the vessel wall.

In some embodiments, the relative lengths of the introducer sheath 80 and cartridge 616 may be set such that the sheath distal end 84 may contact or be in slight interference with the positioning element when the sheath catch 652 is engaged with the sheath hub 83. In this configuration, blood may not flow into the sheath lumen 86 while the apparatus 610 is introduced into the vessel, e.g., when the positioning element is expanded and retracted within the vessel. If the introducer sheath 80 is subsequently retracted (e.g., along with the tubular member), this configuration may allow the introducer sheath 80 to be reintroduced into the puncture, with the bleed back signal being used to indicate when the introducer sheath 80 is back in contact with the positioning element.

In some embodiments, bleed back may be used to position the introducer sheath in a desired location relative to the arteriotomy and/or vessel wall. For example, as shown in FIGS. 15A and 15B, an introducer sheath 80 may be provided that includes one or more side ports 85 (one shown) on the distal end 84 that communicates with the sheath lumen 86. The side port 85 may be offset a predetermined distance from the distal end 84 of the sheath 80, e.g., 1.5 cm.

An elongate dilator (not shown) may be provided that includes a distal end sized to be introduced into the sheath lumen 86 and a relatively small bleed back lumen that extends from one or more side port in the distal end to a proximal end of the dilator. When the dilator is inserted fully into the sheath lumen 86, the side ports may be aligned with one another such that a fluid path is provided from outside the distal end 84 of the sheath 80 into the dilator to a bleed back port on the proximal end of the dilator.

Thus, when the side ports are disposed within a blood vessel and exposed to blood pressure, blood will enter the side port(s) 85 of the sheath 80, into the side port(s) of the dilator, and travel up the dilator lumen. The blood exiting the bleed back port provides a visual confirmation that the distal end 84 is disposed within the vessel. Once the side port 85 in the sheath 80 is no longer exposed to arterial blood pressure, e.g., when the distal end 84 is withdrawn through the vessel wall into the puncture, the bleed back signal ceases. Thus, a visual confirmation is provided that the sheath extends into the vessel by about the distance that the side port(s) is offset from the distal end 84. Alternatively, a bleed back lumen and port may be provided in the dilator such that, when the dilator is fully inserted into the sheath lumen 86, the port is exposed beyond the sheath distal end 84. The port may be spaced apart from the sheath distal end 84 by a predetermined distance, e.g., about two centimeters, such that, when bleed back stops, the sheath 80 may be advanced the predetermined distance to position the distal end 84 adjacent the vessel wall.

Subsequently, the introducer sheath 80 may be maintained in this position, e.g., when the apparatus 610 is introduced to deliver the sealant. When the positioning element is advanced through the sheath lumen 86, the location of the positioning element relative to the vessel wall and arteriotomy is known based on the known position of the introducer sheath 80. For example, with a side port 85 offset 2 cm from the distal end 84 of the sheath 80, a user may know that the expanded positioning element need only be retracted 2 cm to reach the vessel wall. This embodiment for positioning the sheath 80 may minimize dragging the expanded positioning element through the vessel, which may reduce the risk of rupturing the positioning element on calcium or other material within the vessel and/or false positive tactile positioning on vessel wall due to a vessel restriction or bifurcation.

Figure 17A:
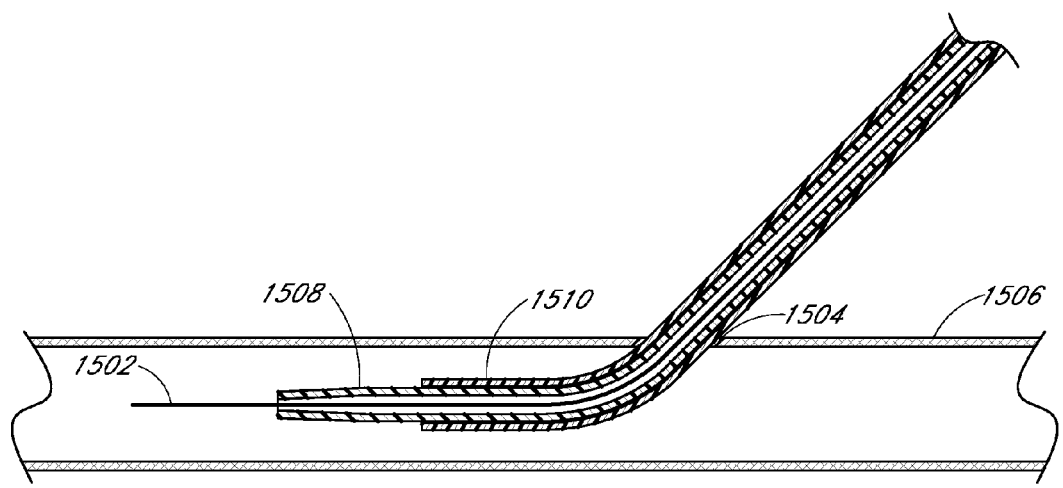
FIGS. 17A-17I illustrate a method of delivering a sealant to an arteriotomy site.

FIGS. 17A-17I describe a method of using the system including any of the sealant delivering apparatuses and dilators described herein. The method can include one or more of the steps described below. A procedural sheath (not shown) can be inserted through a puncture 1504 in a vessel wall 1506 to gain access to a vessel lumen. After the guidewire 1502 extends through the procedural sheath and into the vessel, the procedural sheath can be removed from the tissue tract, leaving the guidewire 1502 in place with the distal tip of the guidewire 1502 positioned within the vessel lumen. The dilator 1508 can then be advanced through the closure system sheath 1510, and the dilator-sheath assembly can be advanced over the guidewire 1502 (FIG. 17A). Any of the mechanisms described herein can be used to determine when the dilator-sheath assembly enters the vessel lumen (e.g., a bleed back port on the dilator and/or sheath).

Figure 17B:
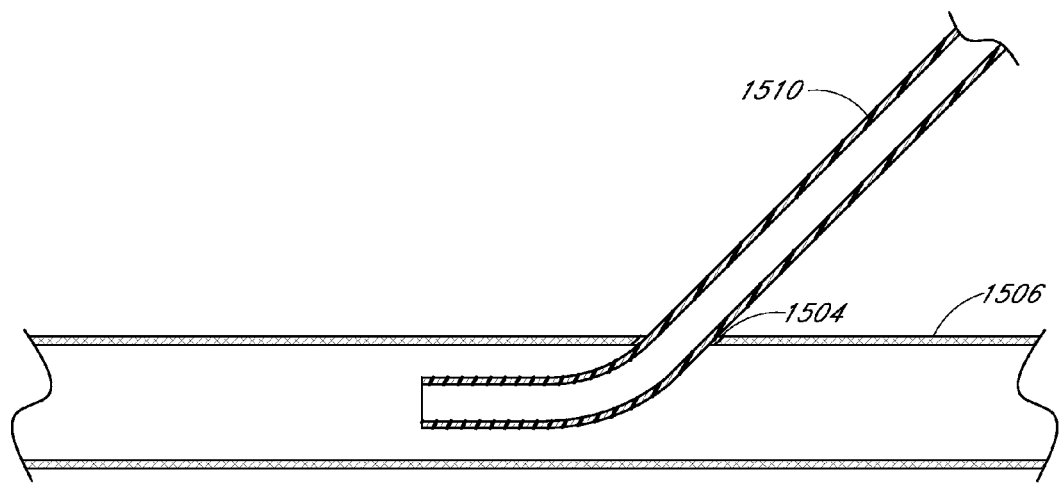
Figure 17C:
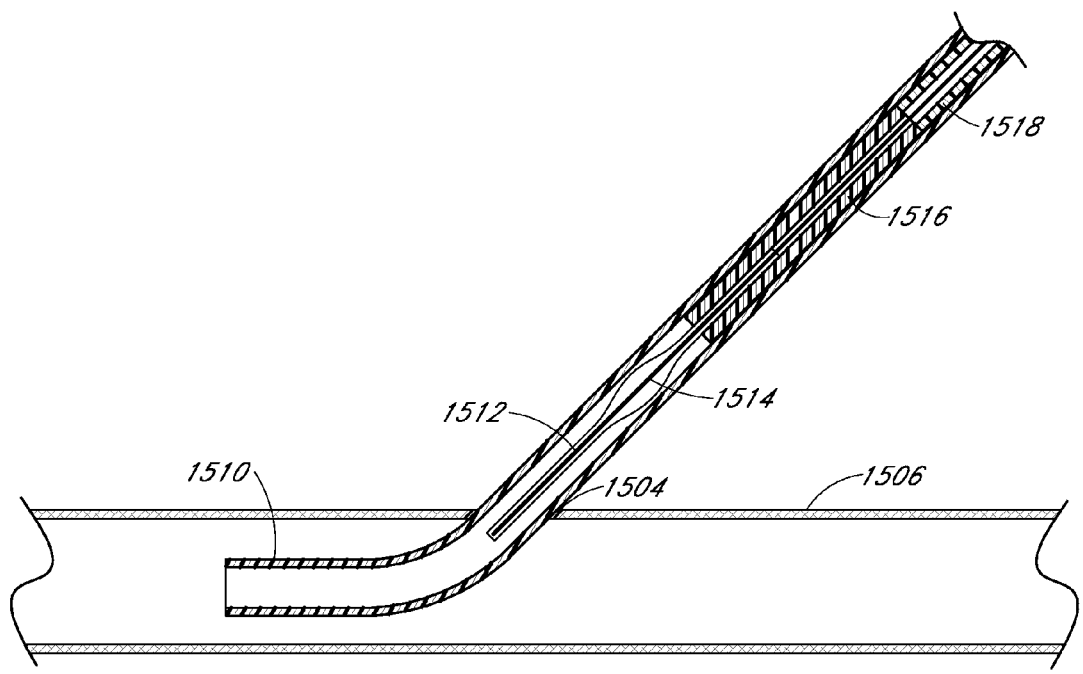
Figure 17D:
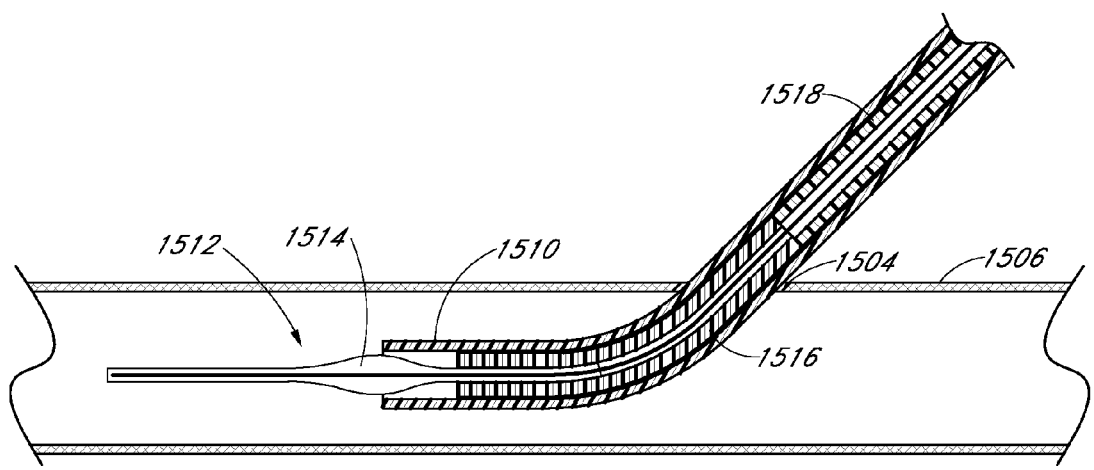
Figure 17E:
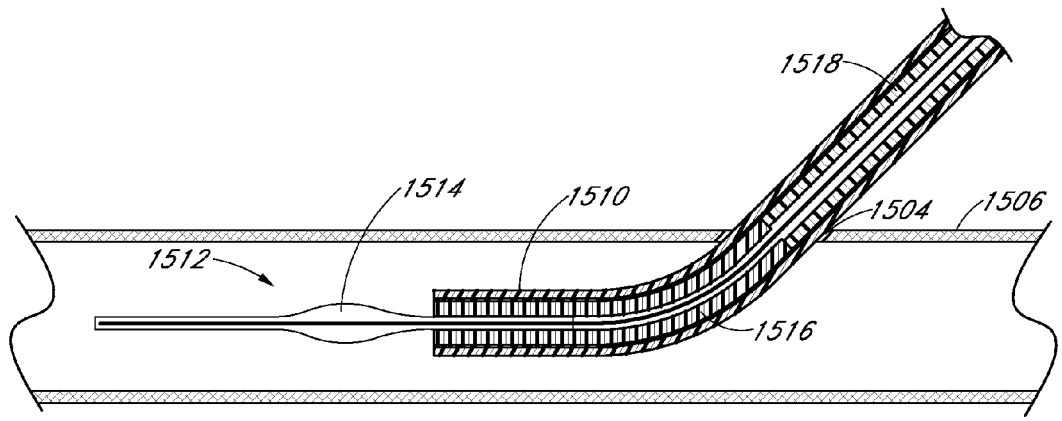
Figure 17F:
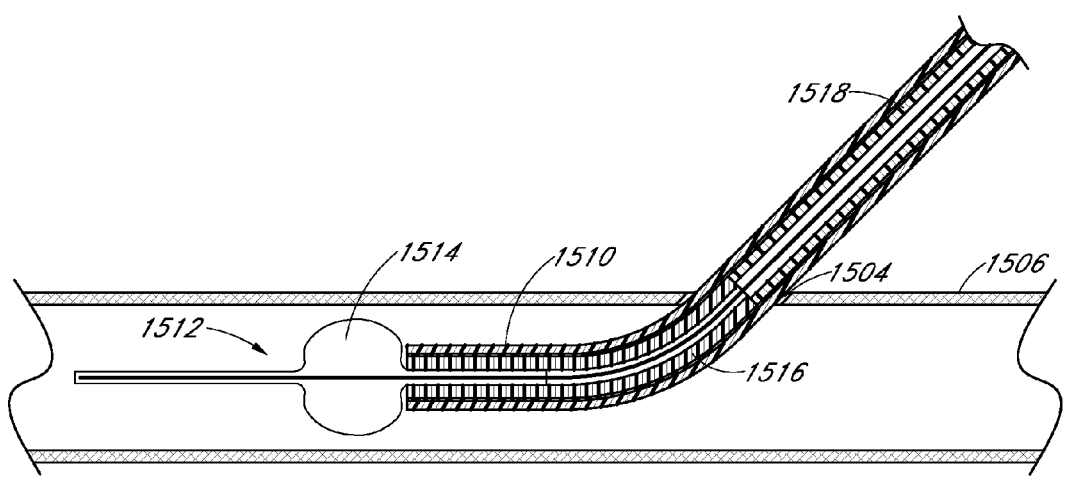

After a distal end of the sheath 1510 extends into the vessel lumen, the dilator 1508 and guidewire 1502 can be proximally retracted and removed leaving the distal end of the sheath 1510 inside the vessel lumen (FIG. 17B). A positioning assembly 1512 can then be introduced into the proximal end of the sheath 1510 and advanced distally through the sheath 1510 (FIGS. 17C-E). As described herein, the positioning assembly 1512 can include a sealant 1516 positioned at a distal portion of the positioning assembly 1512 prior to entering the sheath 1510. After a positioning element 1514 extends out from the distal end of the sheath 1510 and into the vessel lumen, the positioning element 1514 can be expanded within the vessel lumen (FIG. 17F).

Figure 17G:
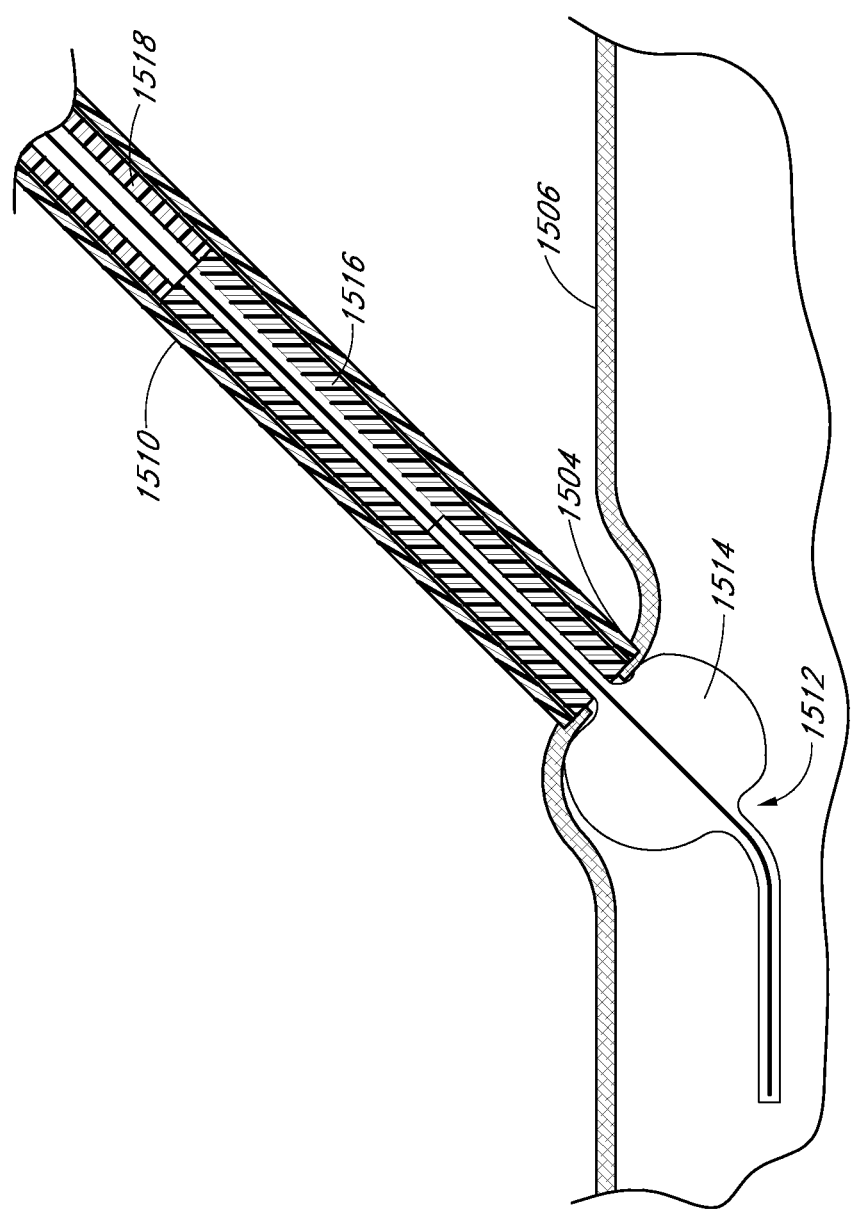
Figure 17H:
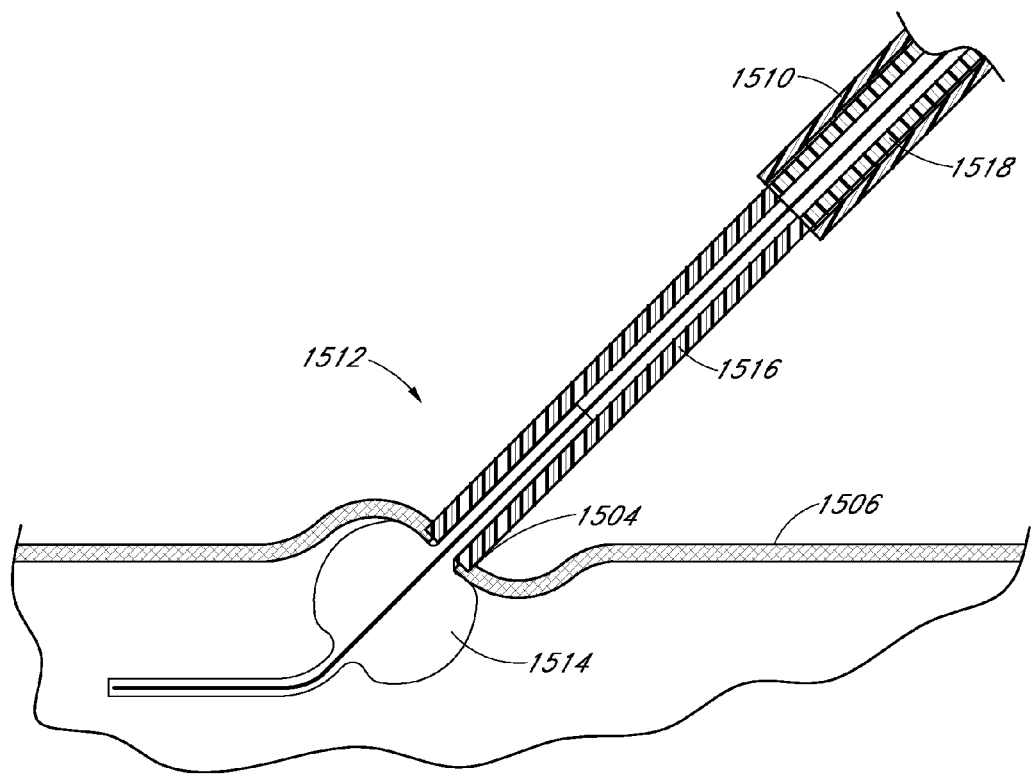
Figure 17I:
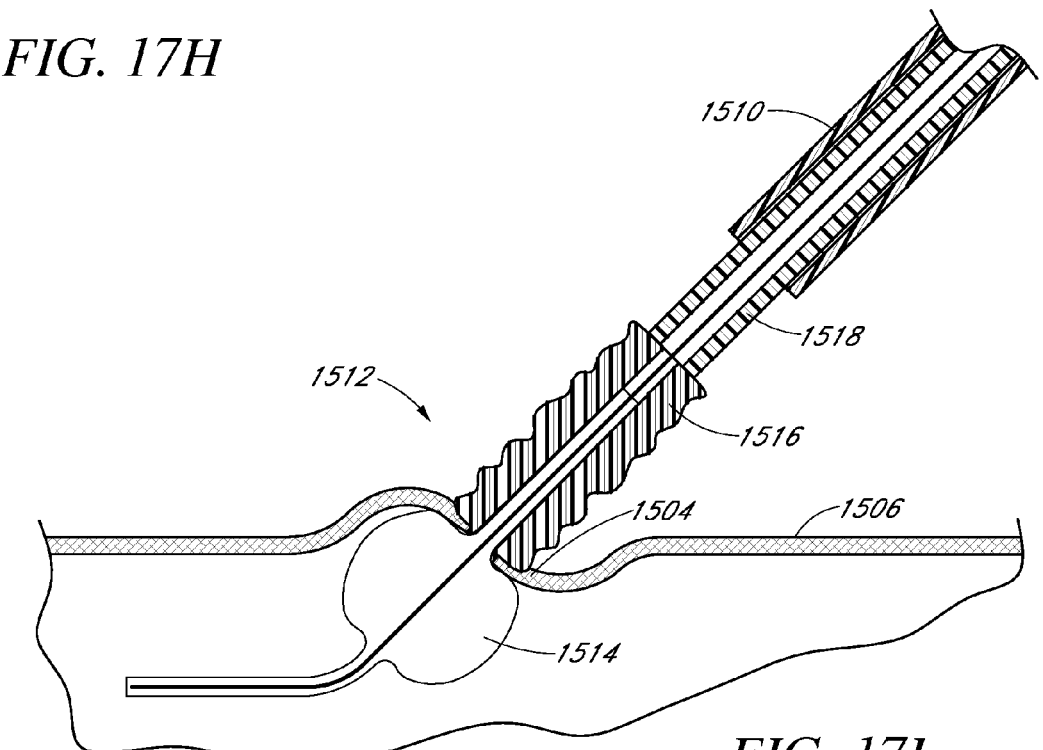

The positioning assembly 1512 can then be withdrawn to seat the positioning element 1514 against the vessel puncture 1504, and the sealant 1516 and sheath 1510 outside the vessel wall 1506 (FIG. 17G). The sheath 1510 can then be partially retracted to expose the sealant 1516 (FIG. 17H). The support member 1518 can then be advanced to tamp the sealant 1516 against the vessel wall 1506 (FIG. 17I). The positioning element 1514 may thereafter be reduced in cross-section (e.g. deflated) and proximally retracted through the sealant 1516. The support member 1518 may be left in position against the sealant during proximal retraction of the positioning element 1514, to maintain the location of the sealant. After removal of the positioning element 1514, the support member 1518 and sheath 1510, if still present within the tissue tract, may be removed from the patient, leaving the sealant 1516 positioned adjacent the vessel wall 1506.

In one implementation of the invention, the positioning element 1514 is an inflatable balloon carried on a distal region of an elongate balloon catheter shaft. The balloon catheter shaft comprises an elongate tubular body having a central lumen extending therethrough to place the inflatable balloon in fluid communication with a source of inflation media which may be coupled to the proximal end of the shaft. A central core wire extends through at least a portion of the central lumen, and through the balloon, to support the distal end of the balloon. The core wire may extend distally beyond the balloon for a length of at least about 2 mm to about 10 mm, and preferably at least about 3 cm to about 5 cm to provide a flexible advance segment.

The inside diameter of the central lumen is greater than the outside diameter of the core wire, to provide an inflation lumen and enable inflation of the balloon.

The sealant 1516 is preferably provided with a central lumen such that it can be pre-mounted on a distal end of the balloon catheter shaft, proximally of the inflatable balloon. The sealant 1516 may be formed as a cylindrical plug, having a central lumen extending therethrough. Alternatively, the sealant 1516 may be provided in a form of a sheet or membrane, which can be wrapped in one or two or three or four or more layers around the catheter shaft.

Referring, for example, to FIGS. 17F and 17G, the sealant is prepositioned on the distal catheter shaft and spaced a short distance from the proximal surface of the inflated balloon. That space may be dimensioned to cooperate with the anticipated wall thickness of the vessel, such as is illustrated in FIG. 17G, so that the inflated balloon can be positioned against the interior wall of the vessel and the sealant will be positioned directly outside of the puncture adjacent the outside wall of the vessel. The space measured in an axial direction between the distal end of the sealant and the proximal surface of the balloon will typically be no greater than about 4 mm, and, in some embodiments, no greater than about 3 mm or 2 mm.

Using this construction, the sealant may be prepositioned on the balloon catheter shaft at the point of manufacture, or, in any event, at the clinical site prior to introduction of the balloon catheter into the patient. The balloon catheter and the sealant are thereafter guided as a single unit by the sheath 1510, from outside of the patient, into the proximal end of the sheath 1510, and guided by the sheath 1510 to the vessel wall. The balloon may thereafter be inflated within the vessel, and the system may be proximally withdrawn as a unit without any internal relative motion between the balloon catheter and the sealant from the distal position illustrated in FIG. 17F to the proximal, seated position in FIG. 17G. Thereafter, proximal retraction of the outer sleeve exposes the sealant.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed is:

1. An apparatus for sealing a puncture through a vessel wall comprising:
    a positioning assembly including an expandable member disposed at a distal portion of the positioning assembly, the expandable member configured to move between an unexpanded state and an expanded state;
    a support member, the positioning assembly configured to move axially within the support member; and
    a handle comprising an outer housing portion and an inner housing portion, the inner housing portion connected to the support member, the outer housing portion configured to selectively engage the inner housing portion,
    wherein the handle comprises a first actuator and a second actuator, the first and second actuators at least partially exposed to the outside of the outer housing portion to permit manipulation by a user,
    wherein the first actuator is an expandable member retraction actuator configured to at least partially retract the expandable member proximally relative to the support member, and
    wherein the second actuator is selected from the group consisting of:
        a support member actuator configured to move the support member distally relative to the outer housing portion; and
        a locking actuator configured to prevent relative movement between the inner housing portion and the outer housing portion until the locking actuator is activated to disengage the inner housing portion.

2. The apparatus of claim 1, further comprising a sheath through which the support member is axially advanceable.

3. The apparatus of claim 2, wherein the handle is configured to engage the sheath such that proximal movement of the outer housing portion moves the sheath proximally relative to the support member.

4. The apparatus of claim 2, wherein the handle further comprises a distal shroud configured to engage the sheath.

5. The apparatus of claim 1, wherein the outer housing portion is configured to move proximally relative to the inner housing portion when the outer housing portion is disengaged from the inner housing portion.

6. The apparatus of claim 1, wherein the inner housing portion is configured to move from a proximal position to a distal position relative to the outer housing portion, and wherein the support member is configured to move toward the expandable member when the inner housing portion is in the distal position.

7. The apparatus of claim 1, wherein the support member is configured to move from a proximal position to a distal position, and wherein the outer housing portion engages the inner housing portion when the support member is in the distal position.

8. The apparatus of claim 1, further comprising a rack and a pinion, the rack and the pinion are configured to move the support member distally relative to the outer housing portion.

9. The apparatus of claim 8, further comprising a locking feature configured to engage the rack, wherein the locking feature is configured to prevent proximal movement of the support member.

10. The apparatus of claim 1, wherein the support member is configured to move from a proximal position to a distal position, and wherein the positioning assembly is configured to move proximally relative to the support member when the support member is in the distal position.

11. The apparatus of claim 1, wherein, when activated, the second support member actuator is configured to engage the outer housing portion to secure the outer housing portion to the inner housing portion.

12. The apparatus of claim 1, wherein the third expandable member retraction actuator is configured to engage the inner housing portion until the support member moves distally.

13. The apparatus of claim 1, wherein the handle further comprises a locking feature configured to selectively prevent the support member from moving relative to the inner housing portion.

14. The apparatus of claim 1, further comprising a sealant disposed at the distal portion of the positioning assembly and proximal to the expandable member.

15. The apparatus of claim 14, further comprising a cartridge carrying the sealant therein.

16. The apparatus of claim 14, wherein the support member is configured to compress the sealant when the support member is moved distally.

17. The apparatus of claim 1, wherein the second actuator is the locking actuator.

18. The apparatus of claim 17, further comprising a third actuator being the support member actuator.

19. The apparatus of claim 1, wherein the expandable member comprises a balloon.

* * * * *

UNITED STATES PATENT AND TRADEMARK OFFICE
CERTIFICATE OF CORRECTION

PATENT NO.        : 8,721,680 B2                    Page 1 of 1
APPLICATION NO.   : 13/839590
DATED             : May 13, 2014
INVENTOR(S)       : Hundertmark et al.

It is certified that error appears in the above-identified patent and that said Letters Patent is hereby corrected as shown below:

IN THE CLAIMS

In claim 11, column 36, line 32: delete "second".

In claim 12, column 36, line 35: delete "third".

Signed and Sealed this
Nineteenth Day of May, 2015

Michelle K. Lee
*Director of the United States Patent and Trademark Office*